(12) United States Patent
Stanton et al.

(10) Patent No.: US 8,461,162 B2
(45) Date of Patent: Jun. 11, 2013

(54) PYRAZOLO[1,5-A]PYRIMIDINE DERIVATIVES

(75) Inventors: Matthew G. Stanton, Medfield, MA (US); Njamkou Noucti, Cambridge, MA (US); David L. Sloman, Boston, MA (US); Jongwon Lim, Lexington, MA (US); Benito Munoz, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 394 days.

(21) Appl. No.: 12/669,843

(22) PCT Filed: Jul. 16, 2008

(86) PCT No.: PCT/US2008/008662
§ 371 (c)(1),
(2), (4) Date: Aug. 23, 2010

(87) PCT Pub. No.: WO2009/014620
PCT Pub. Date: Jan. 29, 2009

(65) Prior Publication Data
US 2010/0305091 A1    Dec. 2, 2010

Related U.S. Application Data

(60) Provisional application No. 60/961,350, filed on Jul. 20, 2007.

(51) Int. Cl.
*A01N 43/90* (2006.01)
*A61K 31/519* (2006.01)
*C07D 487/00* (2006.01)

(52) U.S. Cl.
USPC ..................... 514/259.3; 544/281

(58) Field of Classification Search
None
See application file for complete search history.

(56) References Cited

U.S. PATENT DOCUMENTS

| | | | |
|---|---|---|---|
| 6,235,741 B1 | 5/2001 | Bilodeau et al. |
| 6,245,759 B1 | 6/2001 | Bilodeau et al. |
| 6,380,203 B1 | 4/2002 | Bilodeau et al. |
| 6,544,988 B1 | 4/2003 | Bilodeau et al. |
| 7,262,199 B2 | 8/2007 | Fraley et al. |
| 7,329,662 B2 | 2/2008 | Wichmann et al. |
| 7,550,470 B2 | 6/2009 | Fraley et al. |
| 2006/0094706 A1 | 5/2006 | Paruch et al. |
| 2007/0027156 A1 | 2/2007 | Nakai et al. |
| 2007/0082901 A1 | 4/2007 | Guzi et al. |

FOREIGN PATENT DOCUMENTS

| | | | |
|---|---|---|---|
| WO | 9854093 | | 12/1998 |
| WO | 0053605 | | 9/2000 |
| WO | 2004052315 | | 6/2004 |
| WO | WO2004/052315 | * | 6/2004 |
| WO | 2004052286 | | 8/2006 |
| WO | WO2007/085873 | * | 2/2007 |
| WO | 2007085873 | | 8/2007 |

OTHER PUBLICATIONS

Vippagunta et. al. Advanced Drug Delivery Reviews 48 (2001) 3-26.*
Fraley et al., Biorg. Med. Chem. Lett., 12(2002) 3537-41
Co-pending U.S. Appl. No. 12/223,157 filed Jan. 23, 2007, U.S. National Stage Entry of PCT/GB07/050036, published as WO07/085873.

* cited by examiner

*Primary Examiner* — Jeffrey Murray

(74) *Attorney, Agent, or Firm* — Susan L. Hess; Raynard Yuro; Gerard M Devlin

(57) ABSTRACT

Compounds of the following formula (I) are inhibitors of microtubule affinity regulating kinase, and hence find use in the treatment of neurodegenerative diseases associated with hyperphosphorylation of tau.

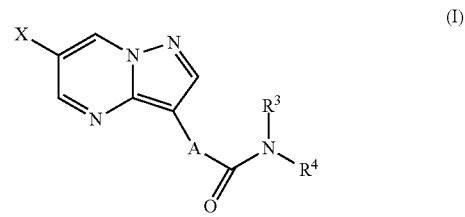

14 Claims, No Drawings

PYRAZOLO[1,5-A]PYRIMIDINE DERIVATIVES

RELATED APPLICATION DATA

This is a National filing under 35 U.S.C. 371 of PCT/US2008/008662, filed Jul. 16, 2008, which claims priority to U.S. Provisional Application No. 60/961,350, filed Jul. 20, 2007.

This invention relates to methods and materials for the treatment or prevention of neurodegenerative diseases such as Alzheimer's disease. In particular, there is disclosed a particular class of pyrazolo[1,5-a]pyrimidine derivatives which selectively inhibit microtubule affinity regulating kinase (MARK).

Alzheimer's disease (AD) is the most common cause of dementia in the elderly and is characterised by a decline in cognitive function, that progresses slowly and results in symptoms such as memory loss and disorientation. Death occurs, on average, 9 years after diagnosis. The incidence of AD increases with age, so that while about 5% of people over the age of 70 are sufferers, this figure increases to 20% of those over 80 years old.

Existing treatments exclusively target the primary symptoms of AD. Diseased neurons may release insufficient or excessive amounts of particular neurotransmitters, and so current drugs are aimed at increasing neurotransmitter levels or at reducing the stimulation of nerve cells by neurotransmitters. Although these drugs provide some improvement in the symptoms of AD, they fail to address the underlying cause of the disease.

The classic clinical and neuropathological features of AD consist of senile or neuritic plaques and tangled bundles of fibers (neurofibrillary tangles) [Verdile, G., et al, Pharm. Res. 50:397-409 (2004)]. In addition, there is a severe loss of neurons in the hippocampus and the cerebral cortex. Neuritic plaques are extracellular lesions, consisting mainly of deposits of β-amyloid peptide (Aβ), surrounded by dystrophic (swollen, damaged and degenerating) neurites and glial cells activated by inflammatory processes. In contrast, neurofibrillary tangles (NFTs) are intracellular clusters composed of a hyperphosphorylated form of the protein tau, which are found extensively in the brain (e.g. mainly in cortex and hippocampus in AD). Tau is a soluble cytoplasmic protein which has a role in microtubule stabilisation. Excessive phosphorylation of this protein renders it insoluble and leads to its aggregation into paired helical filaments, which in turn form NFTs.

The amyloid cascade hypothesis proposes that abnormal accumulation of Aβ peptides, particularly Aβ42, initiates a cascade of events leading to the classical symptoms of AD and ultimately, to the death of the patient. There is strong evidence [e.g. Rapoport, M., et al (2002) Proc. Natl. Acad. Sci. USA 99:6364-6369] that dysregulation of tau function is a key step in the cascade of Alzheimer's disease pathology leading ultimately to neuronal death. Furthermore, tau mutations and NFTs are found in other dementias in which Aβ pathology is absent, such as frontotemporal dementia, Pick's disease and parkinsonism linked to chromosome 17 (FTDP-17) [Mizutani, T. (1999) Rinsho Shikeigaku 39: 1262-1263]. Also, in AD the frequency of NFTs correlates to the degree of dementia better than that of senile plaques [Arriagada, P. V., et al (1992) Neurology 42:631-639], while significant numbers of amyloid plaques are often found in the brains of non-demented elderly people, suggesting that amyloid pathology on its own is not sufficient to cause dementia. For these reasons, normalisation of tau function (in particular prevention of hyperphosphorylation) is seen as a desirable therapeutic goal for the treatment of AD and other dementing conditions.

Tau is a 352-441 amino acid protein encoded by the Mapt (Microtubule-associated protein tau) gene which is widely expressed in the central nervous system (CNS) with localisation primarily in axons [Binder et al *J. Cell Biol.* 1985, 101(4), 1371-1378]. The major function of tau is regulation of the stability of microtubules (MTs), intracellular structural components comprised of tubulin dimers which are integral in regulating many essential cellular processes such as axonal transport and elongation as well as generation of cell polarity and shape. Tau binding to tubulin is a key factor in determining the rates of polymerisation/depolymerisation (termed dynamic instability) of MTs, and tau is therefore key to the regulation of many essential cellular processes [see, for example, Butner, K. A., Kirschner, M. W. (1991) J. Cell. Biol. 115: 717-730].

Tau is a basic protein with numerous serine and threonine residues, many of which are susceptible to phosphorylation. While normal tau has two to three phosphorylated amino acid residues, hyperphosphorylated tau found in AD and other tauopathies typically has eight or nine phosphorylated residues. A variety of kinases promote phosphorylation of these sites, including proline-directed kinases such as glycogen synthase kinase 3β (GSK3β) and cyclin dependent kinase 5 (cdk5), and non-proline-directed kinases such as protein kinase A (PKA) and calmodulin (CaM) kinase II, which phosphorylate tau at Lys-(Ile/Cys)-Gly-Ser sequences, also known as KXGS motifs. One KXGS motif is found in each of the MT binding repeats. Phosphorylation at these sites is important for the regulation of tau-MT binding and while the degree of phosphorylation is normally low, it has been shown to be increased in brain tissue from AD patients. Phosphorylation of one particular residue within the KXGS motifs, Ser-262 has been shown to be elevated in tau protein extracted from the NFTs in AD [Hasegawa, M. et al (1992) J. Biol. Chem. 267:17047-17054] and phosphorylation at this site also appears to dramatically reduce MT binding [Biernat, J. et al. (1993) Neuron 11: 153-163].

Nishimura et al. [Cell 116: 671-682 (2004)] demonstrated that overexpression of the kinase PAR-1 in *Drosophila* led to enhanced tau-mediated toxicity and an increase in the phosphorylation of tau on Ser-262, Ser-356, and other amino acid residues, including sites phosphorylated by GSK3β and Cdk5. Their findings suggest that PAR-1 kinase acts as a master kinase during the process of tau hyperphosphorylation, with the phosphorylation of the Ser-262 and Ser-356 sites being a prerequisite for the subsequent phosphorylation at downstream sites by other kinases.

The mammalian ortholog of PAR-1 is microtubule affinity-regulating kinase (MARK). There are four MARK isoforms and these form part of the AMP-dependent protein kinase (AMPK) family. Like PAR-1, MARK is thought to phosphorylate tau, perhaps in response to an external insult, such as the disruption of $Ca^{2+}$ homeostasis caused by Aβ, priming it for further phosphorylation events. It is not clear whether the phosphorylation of tau by MARK leads directly to its detachment from MTs or the subsequent phosphorylation events cause detachment. The resulting unbound, hyperphosphorylated tau is delocalised to the somatodendritic compartment and is then cleaved by caspases to form fragments prone to aggregation [Drewes, G. (2004). Trends Biochem. Sci 29:548-555; Gamblin, T. C., et al, (2003) Proc. Natl. Acad. Sci. U.S.A. 100:10032-10037]. These aggregates can grow into filaments, which are potentially toxic, eventually forming the NFTs found in AD.

For these reasons, it is proposed that MARK inhibitors will enable the prevention or amelioration of neurodegeneration in AD and other tauopathies.

In WO 98/54093, WO 00/53605, WO 2004/052286, WO 2004/052315 and in Fraley et al, *Biorg. Med. Chem. Lett.*, 12 (2002) 3537-41, various 3,6-disubstituted pyrazolo[1,5-a]pyrimidines derivatives are disclosed as inhibitors of tyrosine kinases (e.g. KDR kinase), implicated in angiogenesis and other cell proliferative processes, but there is no disclosure of utility as MARK inhibitors or in the treatment or prevention of tauopathies, and no disclosure of the compounds of this invention.

According to the invention, there is provided a compound according to formula I:

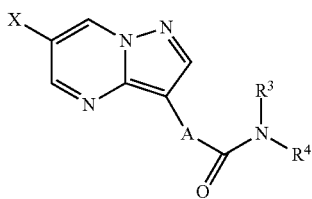

I or a pharmaceutically acceptable salt or hydrate thereof; wherein:

A represents a mono- or bicyclic aromatic ring system of up to 10 ring atoms, of which 0-3 are heteroatoms independently selected from O, N and S, which bears 0-3 substituents independently selected from halogen, CN, $C_{1-4}$alkyl, $CF_3$ and $C_{1-4}$alkoxy;

X represents a monocyclic or bicyclic ring system comprising up to 10 ring atoms, of which 1-3 are selected from N, O and S and the remainder are C, said ring system bearing 0-3 substituents independently selected from halogen, CN, $R^1$-L, $R^1$O-L, $R^1R^2$N-L and $R^1$CONR$^2$;

L represents a bond or a linking group selected from CO, $(CO)_m(CH_2)_n$, $(CO)_m(CH_2)_nO$, $(CO)_m(CH_2)_nNR^2$ and $(CO)_m(CH_2)_nS$;

m is 0 or 1;

n is 0, 1, 2, 3 or 4;

$R^1$ is selected from:

H;

$C_{1-6}$alkyl which is optionally substituted with up to 3 halogen atoms or with OH, CN, $C_{3-6}$cycloalkyl, $C_{1-4}$alkoxy, $C_{1-4}$alkoxycarbonyl, amino, $C_{1-4}$alkylamino or di($C_{1-4}$alkyl)amino; and phenyl or $C_{3-6}$cycloalkyl, either of which is optionally substituted with up to 3 halogen atoms or with OH, CN, $CF_3$, $C_{1-4}$alkoxy, $C_{1-4}$alkoxycarbonyl, amino, $C_{1-4}$alkylamino or di($C_{1-4}$alkyl)amino;

$R^2$ represents H or $C_{1-4}$alkyl;

or $R^1$ and $R^2$ attached to the same nitrogen atom may complete a heterocycle of up to 7 ring atoms which is optionally substituted with up to 3 halogen atoms or with OH, CN, $CF_3$, $C_{1-4}$alkyl, $C_{1-4}$alkoxy, $C_{1-4}$alkoxycarbonyl, amino, $C_{1-4}$alkylamino or di($C_{1-4}$alkyl)amino;

$R^3$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^4$ is selected from:

(i) H;

(ii) $C_{1-8}$alkyl or $C_{2-8}$alkenyl, either of which optionally bears up to 3 substituents independently selected from halogen, OH, CN, $CF_3$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$; and (iii) $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^7$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms;

or $R^3$ and $R^4$ together may complete a mono- or bicyclic heterocyclic system of up to 10 ring atoms which optionally bears up to 3 substituents independently selected from halogen, OH, oxo, CN, $CF_3$, $R^7$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$;

$R^6$ represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^6$ represents phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^6$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino; and $R^7$ has the same definition as $R^6$ except that $R^7$ is not H.

The invention further provides a method for treatment or prevention of a neurodegenerative disease associated with hyperphosphorylation of tau in a human patient, said method comprising administering to that patient an effective amount of a compound of formula I as defined above, or a pharmaceutically acceptable salt or hydrate thereof.

Neurodegenerative diseases associated with hyperphosphorylation of tau include AD, frontotemporal dementia, Pick's disease and parkinsonism linked to chromosome 17 (FTDP-17).

In a further aspect, the invention provides a method for reducing the production of hyperphosphorylated tau in a human patient, said method comprising administering to said patient an effective amount of a compound of formula I as defined above or a pharmaceutically acceptable salt or hydrate thereof.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The term "halogen" as used herein includes fluorine, chlorine, bromine and iodine.

The expression "$C_{3-x}$cycloalkyl" as used herein, where x is an integer greater than 3, refers to nonaromatic hydrocarbon ring systems containing from 3 to x ring atoms. Said systems may be monocyclic or bicyclic if the magnitude of x allows it. Examples include cyclopropyl, cyclobutyl, cyclopentyl, cyclohexyl, cycloheptyl, bicycloheptyl and decalinyl.

Unless indicated otherwise, the term "bicyclic" includes bridged bicyclic and spiro-linked ring systems as well as fused ring systems. However, a bicyclic system in which one or both rings are aromatic is of necessity a fused ring system.

The term "heterocycle" or "heterocyclic" refers to a ring in which 1, 2 or 3 of the ring atoms are independently selected from O, N and S, or to tetrazole. Said ring may be fully saturated or may be unsaturated to any degree, including aromatic. "Heteroaryl" refers to the subset of heterocyclic rings that are aromatic.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, trifluoroacetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

When the compounds useful in the invention have one or more asymmetric centres, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

When a compound useful in the invention is capable of existing in tautomeric keto and enol forms, both of said forms are considered to be within the scope of the invention.

A nitrogen atom forming part of a heteroaryl ring may be in the form of the N-oxide. A sulphur atom forming part of a nonaromatic heterocycle may be in the form of the S-oxide or S,S-dioxide.

A heteroaryl group may be attached to the remainder of the molecule via a ring carbon or a ring nitrogen, provided that this is consistent with preservation of aromaticity.

In formula I, A represents a mono- or bicyclic aromatic ring system of up to 10 ring atoms, of which 0-3 are heteroatoms independently selected from O, N and S, which bears 0-3 substituents independently selected from halogen, CN, $C_{1-4}$alkyl, $CF_3$ and $C_{1-4}$alkoxy. Examples of bicyclic ring systems within the definition of A include naphthalene, quinoline, isoquinoline, benzofuran, benzothiophene, indole, indazole, benzothiazole, benzoxazole and benzimidazole. When A represents a bicyclic system, the moiety $CONR^3R^4$ and the pyrazolopyrimidine core may be attached to the same constituent ring of A, or to separate constituent rings of A.

In a particular embodiment A is monocyclic and hence represents phenyl or 5- or 6-membered heteroaryl. Examples of 6-membered heteroaryl embodiments of A include pyridyl, pyrimidinyl, pyridazinyl and pyrazinyl. Examples of 5-membered heteroaryl embodiments of A include thienyl, furyl, thiazolyl, oxazolyl, isothiazolyl and isoxazolyl. In a particular embodiment A represents phenyl, thienyl or thiazolyl, in particular phenyl or thienyl. When A represents phenyl, the moiety $CONR^3R^4$ is preferably attached at the 3- or 4-position of the phenyl ring. When A represents thienyl or thiazolyl, the moiety $CONR^3R^4$ is preferably attached at the 2-position of the thiophene or thiazole ring, with the pyrazolopyrimidine core attached at the 4-position.

Up to 3 of the free ring positions on A optionally bear a substituent independently selected from halogen, CN, $C_{1-4}$alkyl, $CF_3$ and $C_{1-4}$alkoxy, but typically not more than 2 such substituents are present on A, and preferably 0 or 1 such substituents are present on A. A preferred substituent is $C_{1-4}$alkyl, e.g. methyl. Another preferred substituent is Cl.

In formula I, X represents a monocyclic or bicyclic ring system comprising up to 10 ring atoms, of which 1-3 are heteroatoms selected from N, O and S and the remainder are C. In the case of a bicyclic system comprising 2 or 3 heteroatoms, said heteroatoms may be confined to one of the rings or distributed over both of the rings. In the case of a bicyclic system, preferably at least one of the rings is aromatic, for example the ring which is bonded to the pyrazolopyrimidine system of formula I. In the case of a monocyclic system, the ring typically comprises 5 or 6 ring atoms and may be aromatic or nonaromatic, and in a particular embodiment such a ring is either aromatic or partially unsaturated.

Examples of aromatic monocyclic systems represented by X include pyridine, pyrazole, imidazole, pyrrole, thiophene and furan.

Examples of nonaromatic monocyclic systems represented by X include dihydropyridine and tetrahydropyridine.

Examples of bicyclic systems represented by X include indole, benzofuran, quinoline, isoquinoline, 1H-pyrrolo[2,3-b]pyridine, 5,6-dihydro-4H-pyrrolo[1,2-b]pyrazole and 2,3-dihydro-1H-benzimidazole.

Ring systems represented by X optionally bear up to 3 substituents independently selected from halogen, CN, $R^1$-L, $R^1$O-L, $R^1R^2$N-L and $R^1CONR^2$, where $R^1$, $R^2L$ are as defined previously. Particular identities of L include a bond, $CH_2$, $CH_2CH_2$, $CH_2CH_2CH_2$, $CH_2CH_2O$, $CH_2CH_2CH_2O$, $CH_2CH_2NH$, $CH_2CH_2CH_2NH$ and CO.

Examples of suitable substituents include $R^1$, $R^1CH_2$, $R^1O$, $R^1CO$, $R^1OCH_2CH_2NH$, $R^1R^2N$, $R^1R^2NCH_2CH_2$, $R^1R^2NCH_2CH_2CH_2$, and $R^1R^2NCH_2CH_2CH_2O$, where $R^1$ and $R^2$ are as defined previously. Suitable identities for $R^1$ include H, $C_{1-6}$alkyl (such as methyl, ethyl, propyl and butyl), $C_{3-6}$cycloalkyl$C_{1-6}$alkyl (such as cyclopropylmethyl), hydroxy$C_{1-6}$alkyl, (such as 2-hydroxy-2-methylpropyl), $C_{1-4}$alkoxy$C_{1-6}$alkyl (such as 2-methoxyethyl) and phenyl. Suitable identities for $R^2$ include H and methyl, especially H. Alternatively, $R^1$ and $R^2$ attached to the same nitrogen atom may complete a heterocycle of up to 7 ring atoms which is optionally substituted with up to 3 halogen atoms or with OH, CN, $CF_3$, $C_{1-4}$alkyl, $C_{1-4}$alkoxy, $C_{1-4}$alkoxycarbonyl, amino, $C_{1-4}$alkylamino or di($C_{1-4}$alkyl)amino. Suitable heterocycles include azetidine, pyrrolidine, piperidine, piperazine and morpholine. In a particular embodiment said heterocycle is unsubstituted or bears up to 2 fluorine substituents.

It will be apparent to those skilled in the art that a hydroxyl substituent on an unsaturated ring may be capable of tautomerising to a ketone. In such circumstances, both tautomers are to be considered equivalent. Thus, for example, 2-hydroxypyridine is considered equivalent to 2-oxo-1,2-dihydropyridine.

In a particular embodiment, X represents 2-oxo-1,2-dihydropyridin-4-yl which bears a substituent $R^1R^2N(CH_2)_p$ on the 1-position (i.e. the nitrogen atom of the dihydropyridine ring), where p is 2 or 3 and $R^1$ and $R^2$ are as defined previously. Within this embodiment, specific identities for $R^1R^2N$ include dimethylamino, pyrrolidin-1-yl, 3-fluoropyrrolidin- 1-yl, 3,3-difluoropyrrolidin-1-yl, piperidin-1-yl, 3-fluoropiperidin-1-yl, 3,3-difluoropiperidin-1-yl, 4,4,-difluoropiperidin-1-yl and morpholin-4-yl.

In an alternative embodiment, X represents pyridine which is optionally substituted as defined previously, in particular 3-pyridine which is unsubstituted or substituted in the 6-position. Within this embodiment preferred substituents include $NH_2$, dimethylamino, piperazin-1-yl, 4-methylpiperazin-1-yl, 2-(morpholin-4-yl)ethylamino, cyclopropylmethoxy, acetylamino, 3-(dimethylamino)propoxy, methoxy, 2-hydroxy-2-methylpropylamino, morpholin-4-yl and 2-methoxyethylamino.

In another embodiment X represents 5-membered heteroaryl which is optionally substituted as defined previously, for example optionally-substituted furan, thiophene, pyrrole, imidazole or pyrazole, and in particular optionally-substituted imidazole or pyrazole. Particular substituents include $C_{1-6}$alkyl (especially methyl), phenyl$C_{1-4}$alkyl (such as benzyl), and $C_{2-6}$acyl (such as acetyl). Within this embodiment, suitable identities for X include 1-methyl-1H-pyrazol-5-yl, 1-methyl-1H-pyrazol-4-yl, 1-(3-hydroxy-3-methylbutyl)-1H-pyrazol-4-yl, 1-[2-(morpholin-4-yl)ethyl]-1H-pyrazol-4-yl, 1-[3-(morpholin-4-yl)propyl]-1H-pyrazol-4-yl, 1-methyl-1H-imidazol-4-yl, 1-benzyl-1H-pyrazol-4-yl, 1H-pyrrol-2-yl, 1H-pyrazol-3-yl, 3-thienyl, 3-furyl, 2-furyl, 5-acetyl-2-thienyl and 1H-pyrazol-4-yl.

Further examples of groups represented by X include 5,6-dihydro-4H-pyrrolo[1,2-b]pyrazol-3-yl, quinolin-6-yl, quinolin-3-yl, isoquinolin-4-yl, 1-methyl-1H-indol-5-yl, 1H-indol-5-yl, 1H-indol-6-yl, 1-benzofuran-5-yl, 1-H-pyrrolo[2,3-b]pyridine-5-yl and 2-oxo-2,3-dihydro-1H-benzimidazol-5-yl.

$R^3$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino. In particular, $R^3$ represents H, $C_{1-4}$alkyl (especially methyl) or substituted $C_{1-4}$alkyl (such as dimethylaminoethyl or 2,2,2-trifluoroethyl). In a particular embodiment, $R^3$ is H.

In one embodiment $R^4$ is H.

In an alternative embodiment $R^4$ represents $C_{1-8}$alkyl or $C_{2-8}$alkenyl, either of which optionally bears up to 3 substituents independently selected from halogen, OH, CN, $CF_3$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$ where $R^6$ and $R^7$ are as previously defined. Within this embodiment $R^4$ very suitably represents $C_{1-6}$alkyl which is optionally substituted as defined previously, and in particular with 0, 1 or 2 groups independently selected from $CF_3$, OH, $NH_2$, methoxy, ethoxy and dimethylamino, as in, for example, ethyl, isopropyl, 1,2-dimethylpropyl, 1-ethylpropyl, 2-methylpropyl, 2,2,2-trifluoroethyl, 3,3,3-trifluoropropyl, 2-methyl-1-(trifluoromethyl)propyl, 2-hydroxy-2-methylpropyl, 2-amino-2-methylpropyl, 2-hydroxy-1-methylethyl, 2-methoxyethyl, 2-hydroxyethyl, 2-methoxy-1-methylethyl, 2-hydroxy-3,3,3-trifluoropropyl, 2-hydroxy-2-methyl-1-(trifluoromethyl)propyl, 2-(dimethylamino)ethyl, 2-ethoxyethyl, or 2,3-dihydroxypropyl.

In another embodiment $R^4$ represents $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^7$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms, and where $R^6$ and $R^7$ are as defined previously.

Within this embodiment, examples of suitable cycloalkyl groups include cyclopropyl, cyclobutyl, cyclopentyl, cyclohexyl, optionally substituted as defined previously, and in particular with 0, 1 or 2 fluorine atoms and a group selected from F, OH, $NH_2$, methylamino, morpholin-4-yl and methanesulfonylamino, as in, for example, 2-hydroxycyclohexyl, 4-hydroxycyclohexyl, 2-aminocyclohexyl, 3-aminocyclohexyl, 2-(methylamino)cyclohexyl, 2-(methanesulfonylamino)cyclohexyl, 2-hydroxycyclopentyl, 2-(morpholin-4-yl)cyclopentyl, 3,3,-difluorocyclopentyl, 2-amino-6,6-difluorocyclohexyl, 2-amino-3,3-difluorocyclohexyl, and 2,2-difluoro-6-hydroxycyclohexyl.

Within this embodiment, examples of suitable cycloalkylalkyl groups include cyclopropylmethyl, cyclopropylethyl, cyclopentylmethyl, cyclohexylmethyl and cycloheptylmethyl, optionally substituted as defined previously, and in particular with 0, 1 or 2 groups independently selected from OH, $C_{1-4}$alkyl, di($C_{1-4}$alkyl)amino, piperidin-1-yl, pyrrolidin-1-yl, and morpholin-4-yl, as in, for example, 1-cyclopropylethyl, (1-morpholin-4-ylcycloheptyl)methyl, (1-morpholin-4-ylcyclopentyl)methyl, (1-dimethylaminocyclohexyl)methyl, (1-morpholin-4-ylcyclohexyl)methyl, (1-piperidin-1-ylcyclopentyl)methyl, (2-hydroxy-2-methylcyclohexyl)methyl and (1-hydroxycyclohexyl)methyl.

Within this embodiment suitable identities for groups represented by "Het" or Het$C_{1-4}$alkyl include those in which Het is a tetrahydrothiophene, tetrahydrofuran, tetrahydropyran, azetidine, pyrrolidine, piperidine, octahydrocyclopenta[c]pyrrole, octahydrocyclopenta[b]pyrrole or 1-azabicyclo[2.2.2]octane ring, optionally substituted as defined previously, and in particular with 0, 1 or 2 groups independently selected from halogen, OH, oxo, amino, $C_{1-4}$alkyl and $CF_3$, as in, for example, (1,1-dioxidotetrahydro-3-thienyl)methyl, tetrahydrofuran-2-ylmethyl, 1,1-dioxidotetrahydro-3-thienyl, tetrahydro-3-thienyl, 4-hydroxy-1,1-dioxidotetrahydro-3-thienyl, piperidin-3-yl, 1-methylpiperidin-3-yl, 1-methylpiperidin-4-yl, octahydrocyclopenta[c]pyrrol-5-yl, octahydrocyclopenta[c]pyrrol-4-yl, octahydrocyclopenta[b]pyrrol-4-yl, 1-methylazetidin-3-yl, pyrrolidin-3-yl, 1-methylpyrrolidin-3-yl, 1-methyl-2-oxopyrrolidin-3-yl, 1-isopropylpyrrolidin-3-yl, 1-azabicyclo[2.2.2]oct-3-yl, tetrahydropyran-3-yl, tetrahydropyran-4-yl, tetrahydrofuran-3-yl and tetrahydrofuran-2-yl. Further suitable examples include 3-amino-1,1-dioxidotetrahydro-2H-thiopyran-4-yl and 4-amino-1,1-dioxidotetrahydro-2H-thiopyran-3-yl.

Within this embodiment suitable identities for groups represented by "aryl" or aryl$C_{1-4}$alkyl include those in which "aryl" is a phenyl, pyridine, thiophene, pyrazole, triazole, thiazole or indazole, ring, optionally substituted as defined previously, and in particular with up to 3 (preferably 0, 1 or 2) groups independently selected from halogen, OH, $C_{1-6}$alkyl, $CF_3$, $C_{1-4}$alkoxy, $C_{1-4}$alkylthio, cyano$C_{1-4}$alkyl, amino, di($C_{1-4}$alkyl)amino and phenyl, as in, for example, 5-fluoro-2-pyridyl, 6-amino-2-pyridyl, 3-pyridyl, 6-methoxy-3-pyridyl, 6-methyl-3-pyridyl, 4-pentylphenyl, 3-fluorophenyl, 2-fluorophenyl, 4-bromophenyl, 2-fluoro-4-methylphenyl, 4-chlorophenyl, 4-methylphenyl, 4-methoxyphenyl, 4-cyanomethylphenyl, 4-chloro-3-methylphenyl, 4-hydroxyphenyl, 3-chloro-4-hydroxyphenyl, 4-bromo-2-fluorophenyl, 4-(dimethylamino)phenyl, 4-(trifluoromethyl)phenyl, 5-methylthio-1H-1,2,4-triazol-3-yl, thiazol-2-yl, 5-methylthiazol-2-yl, 4-methylthiazol-2-yl, 1H-indazol-5-yl, 4-amino-1-phenyl-1H-pyrazol-3-yl, 2,2,2-trifluoro-1-(5-fluoropyridin-2-yl)ethyl, 2,2,2-trifluoro-1-(6-methylpyridin-2-yl)ethyl, 2,2,2-trifluoro-1-(pyridin-2-yl)ethyl, 3-thienylmethyl, thiazol-2-ylmethyl, 2-(2-furyl)ethyl, 2,5-difluorobenzyl and 2-amino-3,3,3-trifluoro-1-phenylpropyl.

In a further embodiment, $R^3$ and $R^4$ together complete a mono- or bicyclic heterocyclic system of up to 10 ring atoms which optionally bears up to 3 substituents independently selected from halogen, OH, oxo, CN, $CF_3$, $R^7$, $OR^6$, $SR^7$, $SO_2R^7$, $SO_2N(R^6)_2$, $COR^E$, $CO_2R^6$, $CON(R^6)_2$, $N(R^6)_2$, $NR^6COR^7$ and $NR^6SO_2R^7$ where $R^6$ and $R^7$ are previously defined. Within this embodiment, examples of ring systems completed by R³ and R⁴ include azetidine, pyrrolidine, piperidine, octahydropyrrolo[3,4-b]pyrrole, 1,2,4,5,6,6a-hexahydropyrrolo[3,4-b]pyrrole, 2,6-diazaspiro[3,3]heptane and 3-azabicyclo[3.1.0]hexane, optionally substituted as defined previously, and in particular with up to 3 (preferably 0, 1 or 2) groups independently selected from halogen, OH, $C_{1-6}$alkyl, $CF_3$, hydroxy$C_{1-4}$alkyl, $C_{1-4}$alkoxy$C_{1-4}$alkyl, fluoro$C_{1-4}$alkyl, amino, $C_{1-4}$alkylamino and di($C_{1-4}$alkyl)amino, as in, for example, 3-aminoazetidine, 3,3-difluoroazetidine, 2-hydroxymethylpyrrolidine, 2-methoxymethylpyrrolidine, 3-(methylamino)pyrrolidine, 3-(dimethylamino)pyrrolidine, 3-fluoropyrrolidine, 3-fluoromethylpyrrolidine, 3-(trifluoromethyl)pyrrolidine, 3-hydroxypyrrolidine, 3,3,-difluoropyrrolidine, 3,4-difluoropyrrolidine, 3-aminopiperidine, 3-fluoropiperidine, 4-fluoropiperidine, 4,4-difluoropiperidine, octahydropyrrolo[3,4-b]pyrrol-5-yl, 1-methyl-1,2,4,5,6,6a-hexahydropyrrolo[3,4-b]pyrrol-5-yl, 2,6-diazaspiro[3,3]heptane and 6-hydroxymethyl-3-azabicyclo[3.1.0]hexane.

A particular identity for R⁴ is:

(i)

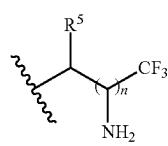

where n is 0 or 1 and R⁵ represents H, $C_{1-6}$alkyl, phenyl or pyridyl, said phenyl or pyridyl optionally bearing a substituent selected from halogen, $CF_3$, $C_{1-4}$alkyl and $C_{1-4}$alkoxy. Particular identities of R⁵ include H, isopropyl, phenyl, 2-pyridyl, 5-fluoro-2-pyridyl and 6-methyl-2-pyridyl. When n is 1, R⁵ is very suitably phenyl.

Another particular identity for R⁴ is:

(ii)

where m is 0 or 1, V represents H, OH or $NH_2$ and W represents $CH_2$, $CF_2$ or $SO_2$. Very suitably, m is 1, V is $NH_2$ and W is $CF_2$.

A first subset of the compounds of the invention consists of the compounds of formula II:

II and the pharmaceutically acceptable salts or hydrates thereof; wherein:
Z1 represents S or O;
Z2 represents N or CR⁹;

R⁸ and R⁹ are independently selected from H, halogen, CN, $C_{1-4}$alkyl, $CF_3$ and $C_{1-4}$alkoxy;
and X, R³ and R⁴ have the same meanings and particular identities as defined previously.

Very suitably, R⁸ and R⁹ are independently H or $C_{1-4}$alkyl such as methyl.

Very suitably, Z1 is S, Z2 is CR⁹ (preferably CH) and R⁸ is H, methyl or Cl; or Z1 is S, Z2 is N and R⁸ is H, methyl or Cl.

Within this subset, X very suitably represents 1-methylpyrazol-4-yl. Also within this subset, R³ is very suitably H while R⁴ has the formula (I) or (ii) indicated above.

A second subset of the compounds of the invention consists of the compounds of formula III:

III and the pharmaceutically acceptable salts or hydrates thereof; wherein:
R⁸ and R⁹ are independently selected from H, halogen, CN, $C_{1-4}$alkyl, $CF_3$ and $C_{1-4}$alkoxy;
and X, R³ and R⁴ have the same meanings and particular identities as defined previously.

In a particular embodiment the moiety $CONR^3R^4$ is attached at the 3- or 4-position of the phenyl ring.

Preferably at least one R⁸ and R⁹ is H, and very suitably both of R⁸ and R⁹ are H.

Specific examples of compounds in accordance with the invention are provided in the Examples hereinafter.

Compounds of formula I may be prepared by Suzuki coupling of compounds (I) with boronic acid derivatives (2a):

(1)

(2)

(a) Y = NR³R⁴
(b) Y = OR⁶ where R represents H or $C_{1-6}$alkyl, or the two RO groups complete a cyclic boronate such as the pinacolate, and A, X, R³ and R⁴ have the same meanings as before. The reaction takes place under normal Suzuki conditions, e.g. in aqueous dioxan at about 100° C. in the presence of a base such as sodium carbonate and $Pd(PPh_3)_4$ as catalyst. Most suitably, the two RO groups represent pinacolate. In a variant of this route, coupling is carried out using an aryl carboxylate ester (2b) wherein R⁶ represents $C_{1-4}$alkyl, such as methyl or ethyl, and the amide is subsequently formed via hydrolysis of the ester and coupling with R³R⁴NH under standard amide coupling conditions.

Compounds (1) are available from Suzuki coupling of dibromide (3a) with X—B(OR)₂:

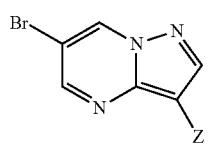

(a) Z = Br
(b) Z = I where X and R have the same meanings as before. In this context, R is very suitably H. The reaction takes place under normal Suzuki conditions as described above.

Alternatively, compounds of formula I may be obtained by reversing the order in which the Suzuki couplings are carried out, e.g. by reacting bromoiodide (3b) with (2a) or (2b) under Suzuki conditions, followed by coupling with X—B(OR)₂ and introduction of the amide group if not already present.

It will be apparent to those skilled in the art that individual compounds in accordance with formula I may be converted into other compounds in accordance with formula I using standard synthetic techniques. For example, compounds in which X is a fluoro-substituted aromatic moiety may be treated with primary or secondary amines in DMF in the presence of alkali at elevated temperatures to provide the corresponding amino-substituted derivatives. Similarly, compounds in which X comprises a dihydro- or tetrahydropyridine ring or similar may be N-alkylated using standard methods. Furthermore, substituents on the ring represented by A may be introduced or interconverted by standard methods. For example, a thiophene ring represented by A may be chlorinated by treatment with thionyl chloride, e.g. at 80° C. Such transformations may also be carried out on intermediates in the synthesis of compounds of formula I.

Where they are not themselves commercially available, the starting materials and reagents described above may be obtained from commercially available precursors by means of well known synthetic procedures and/or the methods disclosed in the Examples section herein.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The compounds of formula I are suitably administered to patients in the form a pharmaceutical composition comprising the active ingredient (i.e. the compound of formula I or pharmaceutically acceptable salt or hydrate thereof) and a pharmaceutically acceptable carrier, and said pharmaceutical compositions constitute a further aspect of the invention.

Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

In one embodiment of the invention, the compound of formula I is administered to a patient suffering from AD, FTDP-17, Pick's disease or frontotemporal dementia, in particular AD.

In an alternative embodiment of the invention, the compound of formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42).

A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compound of formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which modulate the secretion of Aβ (including γ-secretase inhibitors, γ-secretase modulators and β-secretase inhibitors), compounds which inhibit the aggregation of Aβ, and antibodies which selectively bind to Aβ. Such additional compounds further include growth hormone secretagogues, e.g. as described in WO 2004/080459.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature*, 423 (2003), 435-9.

Alternatively, the amyloid modifier may be a compound which modulates the action of γ-secretase so as to selectively attenuate the production of Aβ(1-42). Compounds reported to show this effect include certain non-steroidal antiinflammatory drugs (NSAIDs) and their analogues such as R-flurbiprofen (also known as tarenflurbil or Flurizan™) (see WO 01/78721 and US 2002/0128319 and Weggen et al *Nature*, 414 (2001) 212-16; Morihara et al, *J. Neurochem.*, 83 (2002), 1009-12; and Takahashi et al, *J. Biol. Chem.*, 278 (2003), 18644-70), and compounds which modulate the activity of PPARα and/or PPARδ (WO 02/100836). Further examples of γ-secretase modulators are disclosed in WO 2005/054193, WO 2005/013985, WO 2005/108362, WO 2006/008558, WO 2006/043064, WO 2007/054739, WO 2007/110667, WO 2007/116228, WO 2007/125364 and WO 2008/030391.

Alternatively, the amyloid modifier may be a compound which inhibits the aggregation of Aβ or otherwise attenuates is neurotoxicicity. Suitable examples include chelating agents such as clioquinol (Gouras and Beal, *Neuron*, 30 (2001), 641-2) and the compounds disclosed in WO 99/16741, in particular that known as DP-109 (Kalendarev et al, *J. Pharm. Biomed. Anal.*, 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466. Suitable antibodies also include those specific to Aβ-derived diffusible ligands (ADDLS), as disclosed in WO 2004/031400.

As used herein, the expression "in combination with" requires that therapeutically effective amounts of both the compound of formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of formula I.

EXAMPLES

MARK 3 Assay

MARK3 activity was assayed in vitro using a Cdc25C biotinylated peptide substrate (Cell Signalling Technologies). The phosphopeptide product was quantitated using a Homogenous Time-Resolved Fluorescence (HTRF) assay system (Park et al., 1999, *Anal. Biochem.* 269:94-104). The reaction mixture contained 50 mM HEPES/Tris-HCl, pH 7.4; 10 mM NaCl, 5 mM $MgCl_2$, 0.2 mM $NaVO_4$, 5 mM β-glycerol phosphate, 0.1% Tween-20, 2 mM dithiothreitol, 0.1% BSA, 10 μM ATP, 1 μM peptide substrate, and 10 nM recombinant MARK3 enzyme (University of Dundee) in a final volume of 12 μl. The buffer additionally contained protease inhibitor cocktail (Roche EDTA-free, 1 tab per 50 ml). The kinase reaction was incubated for 2 hours at 25° C., and then terminated with 3 μl Stop/Detection Buffer (50 mM HEPES, pH 7.0, 16.6 mM EDTA, 0.5M KF, 0.1% Tween-20, 0.1% BSA, 2 μg/ml $SLX^{ent}$ 665 (CISBIO), and 2 μg/ml $Eu^{3+}$ cryptate label antibody (CISBIO)). The reaction was allowed to equilibrate overnight at 0° C., and relative fluorescent units were read on an HTRF enabled plate reader (e.g. TECAN GENios Pro).

Inhibitor compounds were assayed in the reaction described above to determine compound IC50s. Aliquots of compound dissolved in DMSO were added to the reaction wells in a third-log dilution series covering a range of 1 nM to 10 μM. Relative phospho substrate formation, read as HTRF fluorescence units, was measured over the range of compound concentrations and a titration curve generated.

The compounds described below gave $IC_{50}$ values of 1 μM or less, typically 500 nM or less, and in preferred cases 50 nM less, in the above assay. The following table provides $IC_{50}$ values in the above assay for representative examples:

| Example | $IC_{50}$ (nM) |
|---------|----------------|
| 219     | 127            |
| 205     | 60             |
| 202     | <0.3           |
| 184     | 607            |
| 50      | 35             |
| 49      | 4              |
| 8       | 158            | pTau(S262) Cell Biochemical and Functional Assay

The cell biochemical potency of the below described MARK inhibitors was evaluated by measuring their ability to block the phosphorylation of Tau at S262 in primary cell culture of rat cortical neurons induced by the action of Okadaic acid.

Reagents:
  Neurobasal (Invitrogen, cat. 21103-049)
  B27 (Invitrogen, cat. 17504-044)
  L-Glutamine (Invitrogen, cat. 25030-081)
  Penicillin-Streptomycin (Invitrogen, cat. 15140)
  Papain, sterile lyophilized (Worthington, cat. NC9212788)
  10 mL 1M Hepes added for 10× solution
  Tissue Culture plates:
    384 well: BD FALCON BD BIOCOAT Poly-D-Lysine Black/Clear Microtest, Tissue-Culture Treated Polystyrene (cat. 354663)
  E18 Primary Rat Cortical Cells: BrainBits, cat. cx2
  Stock Media (NB): Neurobasal+B-27 (1:50)+0.5 mM L-Glutamine+1% Pen/Strep
Preparation of Isolated Neurons
  1. Store tissue at 4° C. (1-2 days) until ready to use.
  2. When ready to plate, make up 2 mL of enzymatic solution in Hibernate-Ca containing 1× papain. Filter sterile solution with 0.2 μm filter.

3. Transfer 2 mL of medium from tissue tube into 15 mL falcon tube while not disturbing tissue. Save media.
4. Add 2 mL enzymatic media (2) to tissue. Incubate for 30' at 37° C.
5. Remove enzymatic solution while not disturbing tissue. Add back 1 mL of media from (3).
6. Using pipettor with sterile plastic tip, triturate ~10 times until most of the cells are dispersed.
7. Let undispersed pieces settle by gravity 1 minute.
8. Transfer dispersed cells (supernatant) into 15 mL falcon tube containing 1 mL media from (3). Gently mix cells by swirling.
9. Spin cells at 1,100 rpm for 1 minute. Remove supernatant.
10. Flick tube to loosen cell pellet. Resuspend cells in 5 mL of NB.
11. Transfer to new 50 mL falcon tube using 40 µm cell strainer. Rinse 15 mL falcon tube with 5 mL media, add to strainer.
12. Count cells using hemacytometer.
13. Dilute cells to 7,000 cells/100 µL/well in NB.
14. Incubate cells at 37° C. with 5% $CO_2$.
    a. 4 DIV: Replace ½ volume (50 µL) NB per well.
    b. 6 DIV: Neurite Assay.

Tissue Culture/Compound Treatment

Primary rat cortical neurons plated @ 6Kcells/well in 384-well black/clear bottom Poly D-Lysine coated BD Falcon Biocoat plates.

Media: Neurobasal+1×B27+2 mM L-Glutamine (+10% FBS) at time of plating

Cells maintained at 37° C. and 5% $CO_2$ for *6 days in culture, w/½ media change every 3-4 days.

Compound Treatment:

Prepare first plate: 200× compound in 100% DMSO with subsequent 3 fold serial dilution Prepare intermediate plate: 1:40 dilution of 200× compound in media (2.5% DMSO)

Add 5× compound to cell in media at 1:5 dilution (0.5% final DMSO)

Incubate for 30 min. at 37° C.

Okadaic Acid (OA) Treatment:

Dilute OA stock (240 uM in 100% DMSO) to 6× final concentration in media (0.5% DMSO)

Add 6× OA to cells at 1:6 dilution (200 nM final).

Incubate for 1.5 hrs. at 37° C.

Fix and Immunostaining

Fix: 1% PFA, diluted in PBS

Wash 1× with PBS, residual 30 ul/well.

Add 30 ul/well warmed 2% PFA and incubate 30 min. at RT (1% PFA final)

Wash 3× with PBS, 30 µl/well residual

Permeabilize & Block.

Add 30 ul/well PBS+0.2% Triton X-100+10% normal goat serum (0.1% Triton & 5% NGS final).

Incubate 1 hr at RT or O/N at 4° C.

Wash 3× with PBS, 30 ul/well residual

Primary antibody: add 30 ul/well 2× final concentration antibody diluted in PBS

Mouse anti-tau-3R

Rabbit anti-tau-pS[262]

Incubate 0/N at 4° C.

Wash 4× with PBS, 30 µl/well residual

Secondary antibody & nuclear staining: add 30 ul/well 2× final concentration stain diluted in PBS AlexaFluor goat anti mouse 488

AlexaFluor goat anti rabbit 594

Hoechst

Incubate in dark 1 hr. at RT

Wash 4× with PBS 30 ul/well residual, protect from light

Acquire images in INCell Analyzer 1000 & Opera.

The compounds described below gave $IC_{50}$ values of 10 µM or less, typically 1000 nM or less, and in preferred cases 250 nM less, in the above assay measuring inhibition of phosphorylation of Tau at S262.

Synthetic Schemes

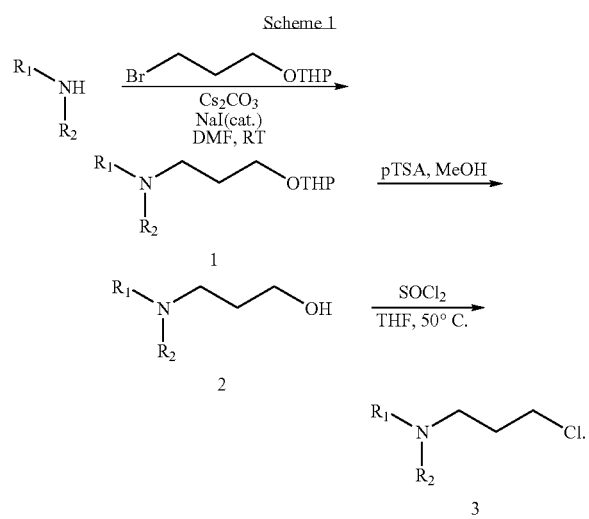

Electrophiles employed in the final step in scheme 2 were either purchased or prepared according the route outlined in scheme 1. Amines were alkylated with THP-protected 3-bromo-1-propanol to generate aminopropanols of type 1. Deprotection of the alcohol and conversion to the alkyl chloride by treatment with thionyl chloride generated electrophiles 3.

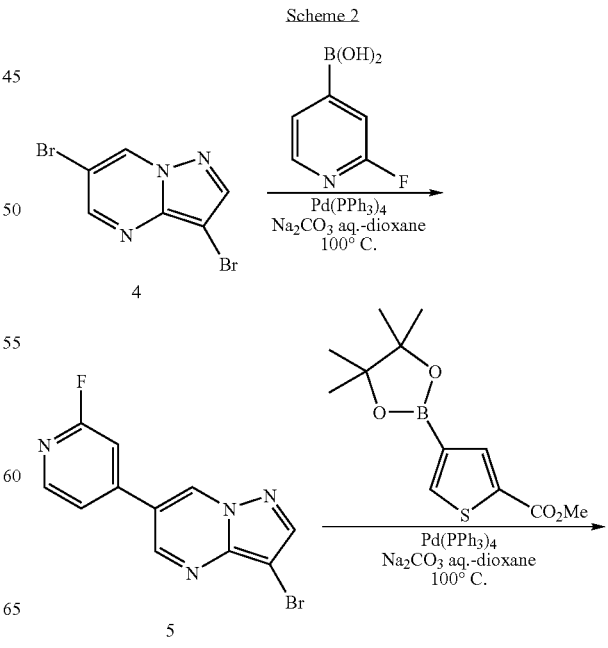

Scheme 3

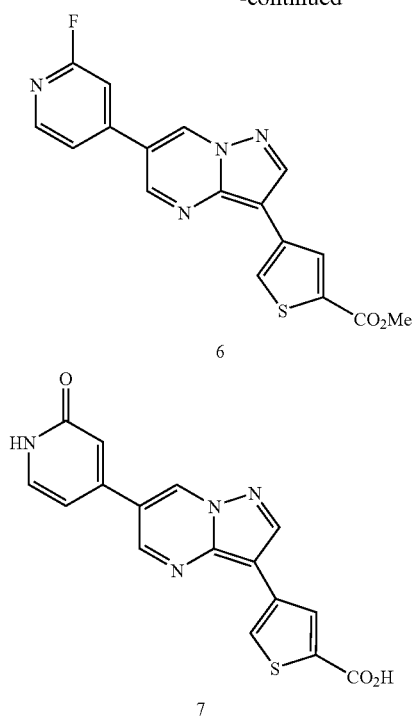

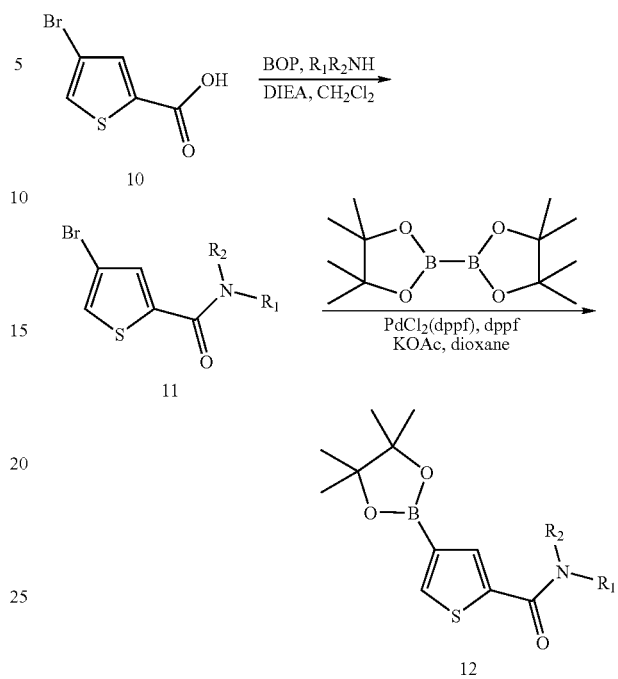

Boronic esters 12 were prepared according to the procedure outlined in scheme 3. Standard coupling of commercially available carboxylic acid 10 with amines generated amides 11. Palladium catalyzed formation of the boronic ester with pinacoldiborane gave esters 12.

Scheme 4

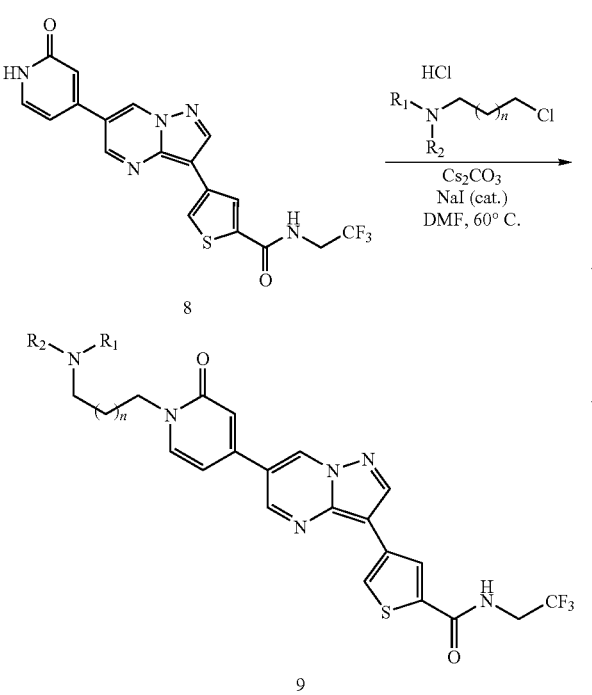

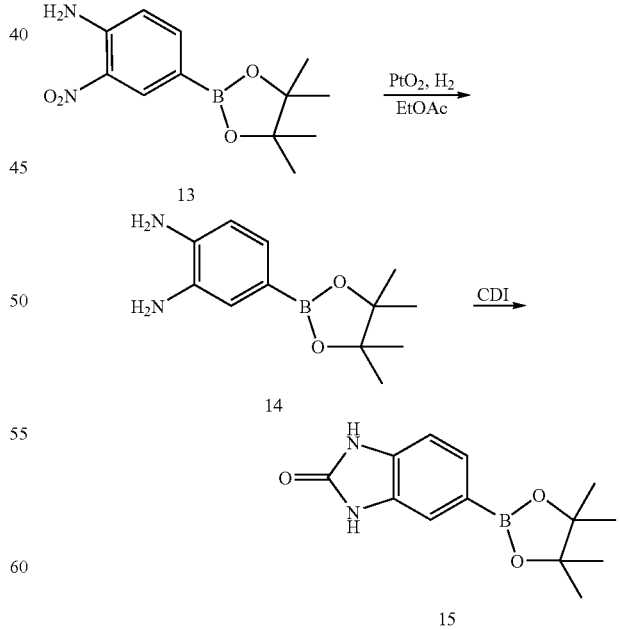

Preparation of N-alkylpyridinones of type 9 began with a regioselective Suzuki coupling of dibromopyrazolopyrimidine 4 with 2-fluoropyridine-4-boronic acid. A second Suzuki coupling was employed to install the thiophencarboxylic ester (6). Hydrolysis of the methyl ester and fluoropyridine with aqueous hydrochloric acid generated pyridinone 7. The amide (8) was formed under standard coupling conditions followed by N-alkylation of the pyridinone to give target molecules 9.

The preparation of boronic ester 15 was completed by hydrogenation of the commercially available nitro-boronic ester 13 and formation of the cyclic urea with CDI (scheme 4).

Scheme 5

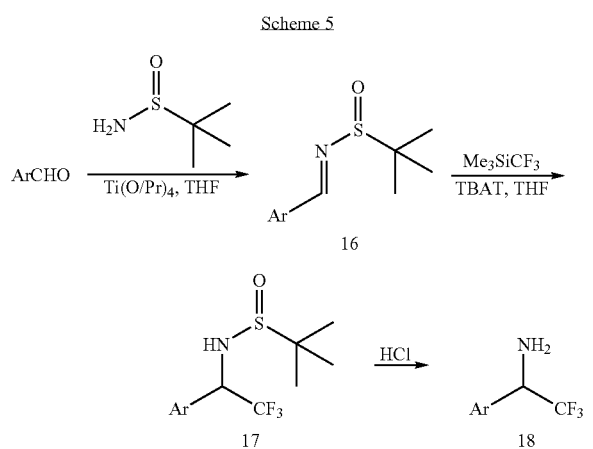

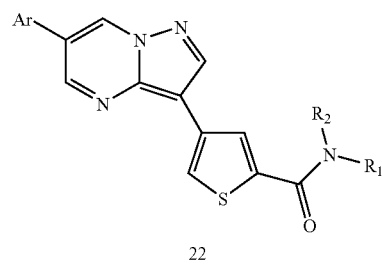

Preparation of substituted trifluoroethylamines was conducted according to scheme 5. Aromatic aldehydes were condensed with t-butyl sulfinamine and then treated with trimethylsilyltrifluoromethane and TBAT to generate the elaborated trifluoroethyl sulfinamine 17. Deprotection with hydrogen chloride gave desired products 18.

Molecules of type 22 were prepared according to Scheme 6. Suzuki coupling of 4 aryl boronic acids/esters gave regioselective coupling product 19. A second Suzuki coupling with the thiophene boronic ester gave 20. The ester was hydrolyzed with aqueous hydrochloric acid and the amide 22 formed under standard coupling conditions.

Scheme 6

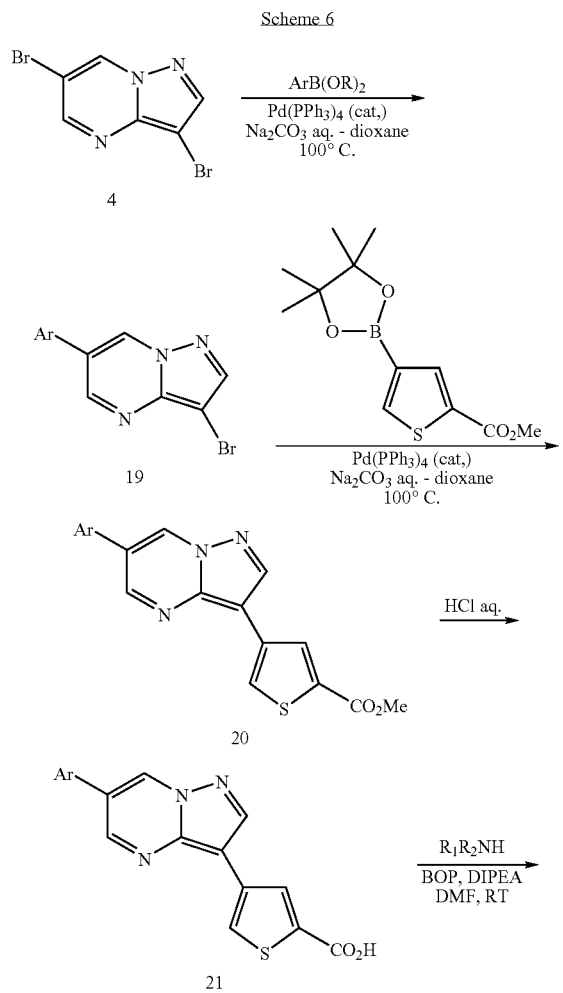

Scheme 7

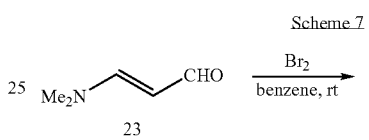

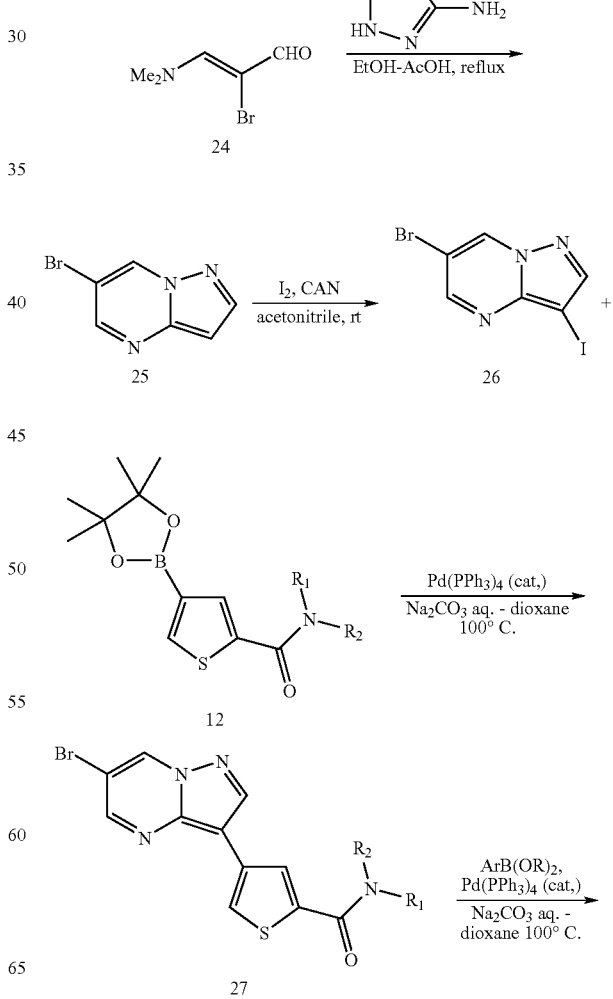

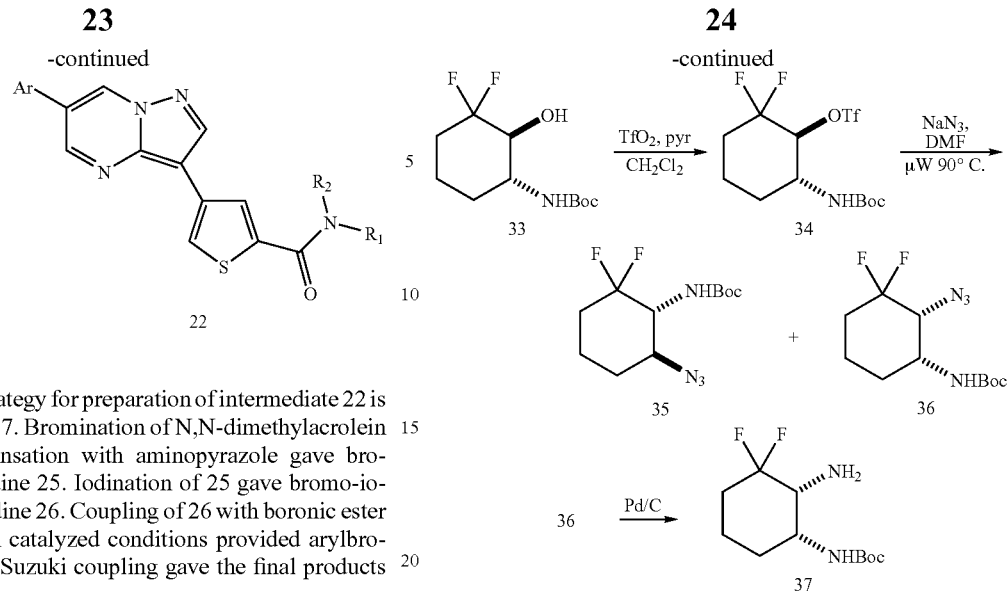

An alternative strategy for preparation of intermediate 22 is depicted in Scheme 7. Bromination of N,N-dimethylacrolein followed by condensation with aminopyrazole gave bromopyrazolopyrimidine 25. Iodination of 25 gave bromo-iodopyrazolo-pyrimidine 26. Coupling of 26 with boronic ester 12 under palladium catalyzed conditions provided arylbromide 27. A second Suzuki coupling gave the final products 22.

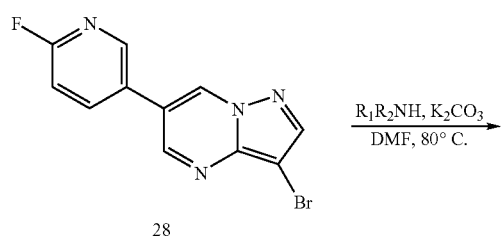

Preparation of aminopyridine intermediates 29 was accomplished using fluoropyridine analogue 28 under thermal displacement conditions.

Commercially available 7-oxabicyclo[4.1.0]heptan-2-one was reacted with deoxofluor to obtain 3,3-difluorinated product 30. Epoxide activation with trimethylaluminum and reaction with a known chiral amine provided amino alcohol 31. The free amine 32 was revealed via hydrogenation and then reprotected as the tert-butyl carbamate 33. The alcohol was activated towards displacement by conversion to triflate 34. Nucleophilic displacement by sodium azide provided 36 which was subsequently reduced to yield amine 37.

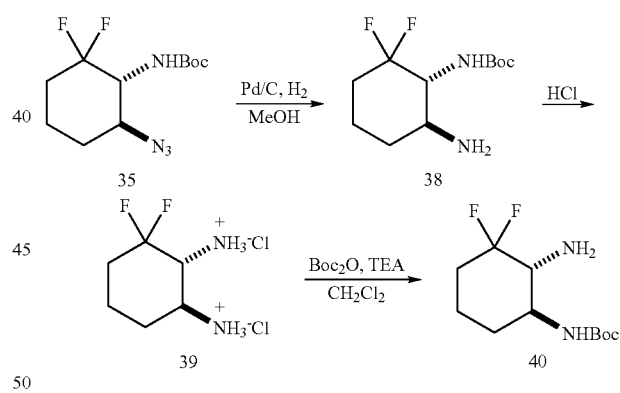

Intermediate 35 was reduced to the corresponding diamine 38. Deprotection of 38 under acidic conditions produced the bis-HCl salt 39. Selective monoprotection of 39 yielded Boc-protected diamine 40.

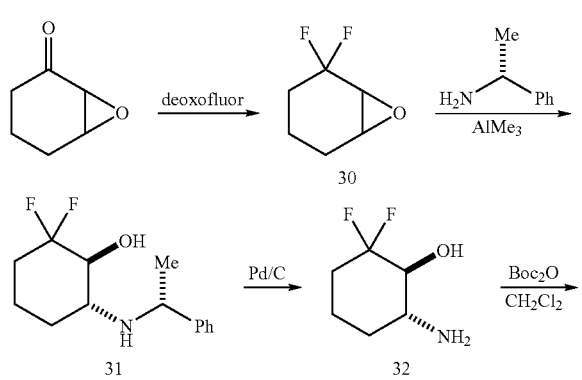

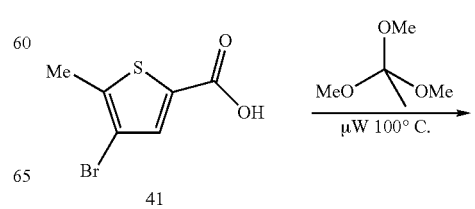

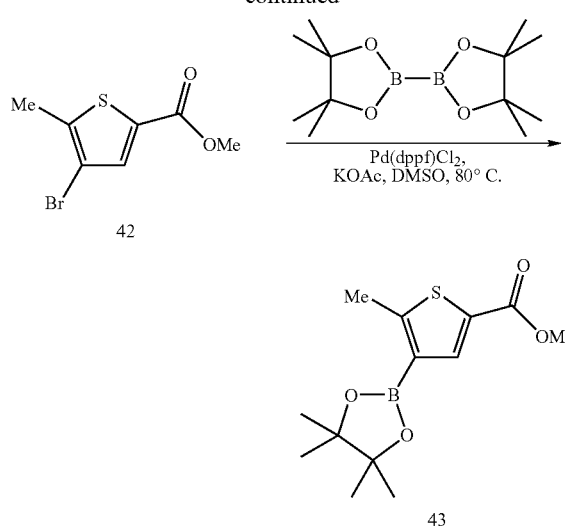

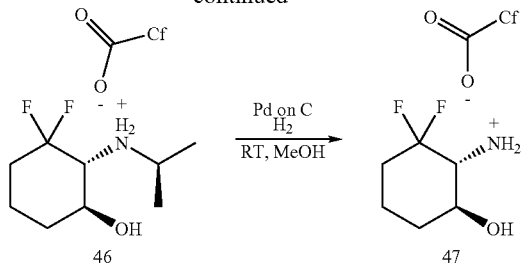

Obtained as an intermediate from scheme 9, compound 31 was mesylated under mild conditions. Aziridine 45 was formed by heating a THF solution of compound 44 and triethylamine to 100 C in a sealed microwave vial. Aziridine 45 was opened under acidic conditions to yield the new difluoro aminoalcohol 46. The benzyl group was then removed under standard hydrogenation conditions to give compound 47.

Commercially available 4-bromo-5-methyl-2-thiophenecarboxylic acid 41 (1.03 g, 4.66 mmol) and trimethyl orthoacetate (1.53 ml, 13.98 mmol) were heated at 40 min at 100° C. in a microwave reactor to yield ethyl ester 42. Boronic ester 43 was generated via a palladium-mediated coupling with bispinacolatodiboron.

Scheme 13

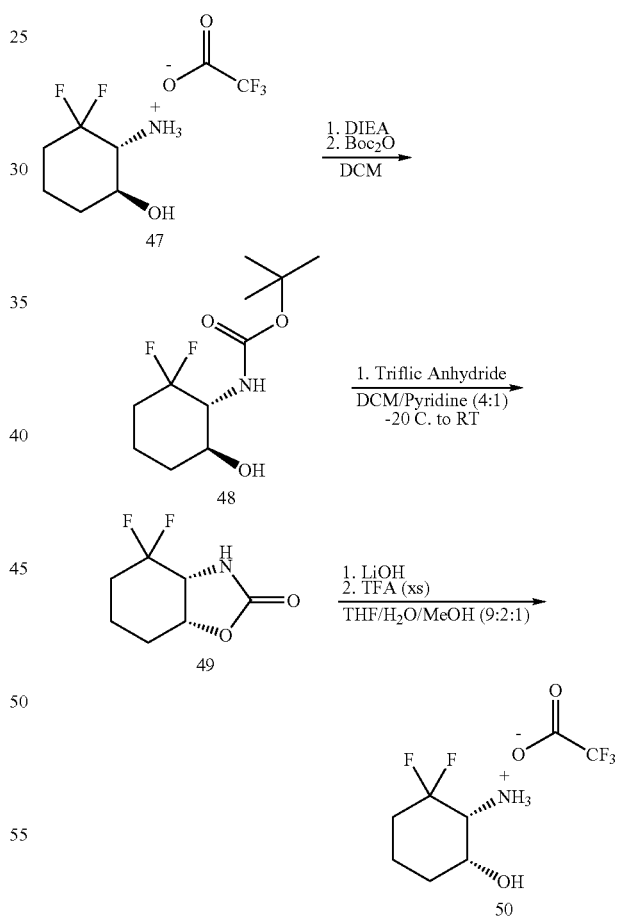

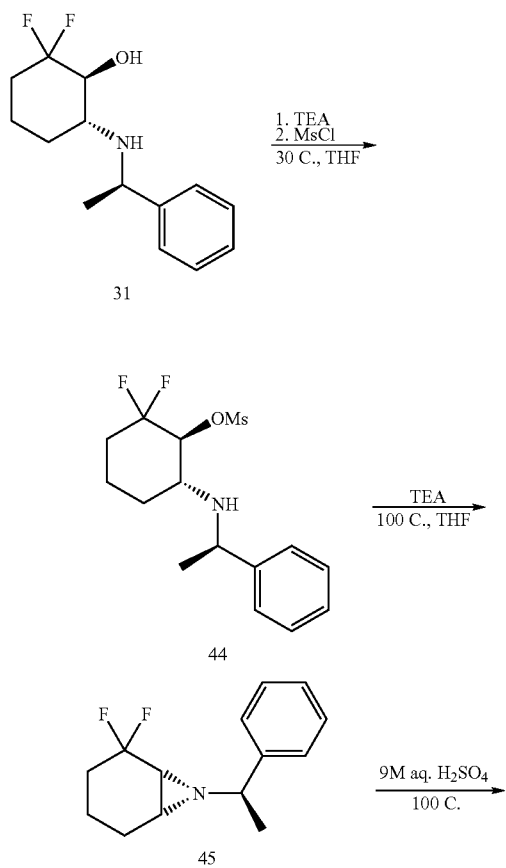

Compound 47 was Boc protected at room temperature to give compound 48. Triflic anhydride was added to a solution of 48 in a four to one mixture of DCM and pyridine at −20 C. Carbamate 49 was generated after an aqueous work-up at room temperature. Opening the carbamate with lithium hydroxide in a trisolvent mixture of THF, Water, and methanol at 50 C generated the cis-difluoro aminoalcohol 50.

Scheme 14.

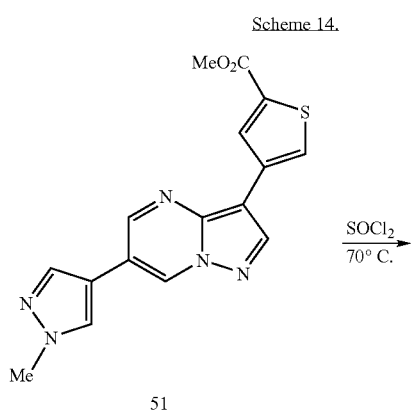

1-Chlorination of thiophene 51 to afford 52 was accomplished by refluxing in neat thionyl chloride for 8 hrs.

Example 1

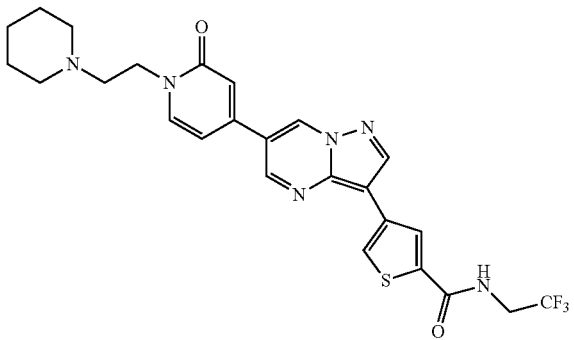 [SMILES: O=C(NCC(F)(F)F)c1cc(-c2cnn3cc(-c4ccn(CCN5CCCCC5)c(=O)c4)cnc23)cs1]

4-{6-[2-oxo-1-(2-piperidin-1-ylethyl)-1,2-dihydropyridin-4-yl]pyrazolo[1,5-a]pyrimidin-3-yl}-N-(2,2,2-trifluoroethyl)thiophene-2-carboxamide (Scheme 2)

Step A: Suzuki Coupling 3,6-Dibromopyrazolo[1,5-a]pyrimidine (3.80 g, 13.7 mmol) was mixed with 2-fluoropyridin-4-yl-4-boronic acid (2.51 g, 17.80 mmol). Dioxane (100 mL) and 1M $Na_2CO_3$ (27.4 mL) were added. The mixture was evacuated and flushed with nitrogen under stirring, then $Pd(Ph_3P)_4$ (0.81 g, 0.70 mmol) was added in a counter flow of nitrogen. The reaction mixture was refluxed under stirring for 16 h, cooled, and poured into a 5-fold excess of water. The product was extracted thrice with $CHCl_3$. The organic layer was washed with brine, dried with $MgSO_4$, filtered, and evaporated. The residue was purified by column chromatography (silica gel, $CHCl_3$/MeOH, 10:1). Yield 3-bromo-6-(2-fluoropyridin-4-yl)pyrazolo[1,5-c]pyrimidine: 2.16 g (54%).

Step B: Suzuki Coupling

Methyl 4-(4,4,5,5-tetramethyl-1,3,2-dioxaborolan-2-yl)thiophene-2-carboxylate (2.160 g, 5.24 mmol) was added to 3-bromo-6-(2-fluoropyridin-4-yl)pyrazolo[1,5-c]pyrimidine (1.18 g, 4.03 mmol). Dioxane (80 mL) and 1M $Na_2CO_3$ (8.0 mL) were added. The mixture was evacuated and flushed with nitrogen under stirring, then $Pd(Ph_3P)_4$ (0.33 g, 0.28 mmol) was added in a counter flow of nitrogen. The reaction mixture was refluxed under stirring for 16 h, cooled, and poured into a 5-fold excess of water. The product was extracted thrice with $CHCl_3$. The organic layer was washed with water, brine, dried with $MgSO_4$, filtered, and evaporated. Yield of crude product methyl 4-[6-(2-fluoropyridin-4-yl)pyrazolo[1,5-a]pyrimidin-3-yl]thiophene-2-carboxylate: 1.460 g.

Step C: Hydrolysis

The hydrolysis of methyl 4-[6-(2-fluoropyridin-4-yl)pyrazolo[1,5-c]pyrimidin-3-yl]thiophene-2-carboxylate was carried out in 9M HCl (25 mL) under reflux for 12 h. The water was distilled off, and the residue was subjected to coevaporation with acetonitrile and dried in a vacuum oven at 59° C. Yield of acid (hydrochloride): 1.11 g (70% for 2 steps).

Step D: Coupling

4-[6-(2-oxo-1,2-dihydropyridin-4-yl)pyrazolo[1,5-c]pyrimidin-3-yl]thiophene-2-carboxylic acid (1.10 g, 2.95 mmol) was dissolved in DMF (30 mL). BOP (1.09 g, 2.46 mmol) was added, and the reaction mixture was stirred for 20 min. DIPEA (2.60 mL, 14.75 mmol) and 2,2,2-trifluoroethylamine (0.52 g, 5.89 mmol) were added. The reaction mixture was stirred overnight at room temperature. The DMF was distilled off. The residue was washed on a filter with water, 5% $NaHCO_3$, and ether and dried in a vacuum oven at 59° C. Yield of amide: 0.810 g (65%).

Step E: Alkylation

A mixture of 4-[6-(2-oxo-1,2-dihydropyridin-4-yl)pyrazolo[1,5-a]pyrimidin-3-yl]-N-(2,2,2-trifluoroethyl)thiophene-2-carboxamide (0.140 g, 0.334 mmol), 1-(2-chloroethyl)piperidine hydrochloride (0.092 g, 0.5 mmol), $Cs_2CO_3$ (0.435 g, 1.34 mmol), and NaI (0.010 g, 0.067 mmol) was evacuated and flushed with argon. DMF (15 mL) was added. The mixture was stirred for 16 h at 65-70° C. and evaporated. The residue was washed on a filter with water, ether, and purified on HPLC. Yield of 4-{6-[2-oxo-1-(2-piperidin-1-ylethyl)-1,2-dihydropyridin-4-yl]pyrazolo[1,5-a]pyrimidin-3-yl}-N-(2,2,2-trifluoro ethyl)thiophene-2-carboxamide (bis-TFA salt): 0.022 g. $^1$H NMR (400 MHz, DMSO-$d_6$): 1.57-1.77 (4H, m), 1.82-1.92 (2H, m), 2.90-3.02 (2H, m), 3.40-3.50 m), 4.05-4.15 (2H, m), 4.33 (2H, dd, J=6.85 Hz, J=6.85 Hz), 6.98 (1H, dd, J=7.1 Hz, J=2.2 Hz), 7.13 (1H, d, J=2.2 Hz), 7.89 (1H, d, J=7.1 Hz), 8.25 (1H, d, J=1.2 Hz), 8.50 (1H, d, J=1.2 Hz), 8.73 (1H, s), 9.11 (1H, d,

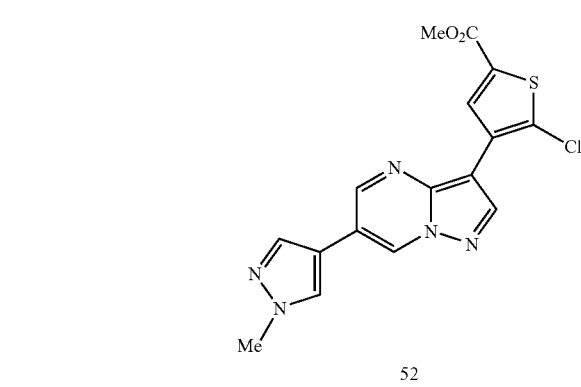

J=2.2 Hz), 9.17 (1H, br s), 9.23 (1H, dd, J=6.35 Hz, J=6.35 Hz), 9.70 (1H, J=2.2 Hz). LC-MS APCI: m/z 531.1 [M+H]$^+$.

Example 2

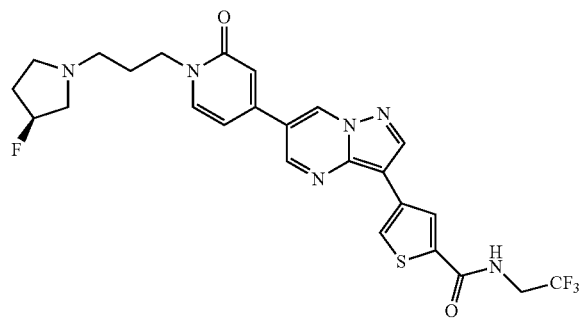 [SMILES: O=C(NCC(F)(F)F)c1cc(-c2cnn3cc(-c4ccn(CCCN5CC[C@H](F)C5)c(=O)c4)cnc23)cs1]

4-[6-(1-{3-[(3S)-3-fluoropyrrolidin-1-yl]propyl}-2-oxo-1,2-dihydropyridin-4-yl)pyrazolo[1,5-a]pyrimidin-3-yl]-N-(2,2,2-trifluoroethyl)thiophene-2-carboxamide (Schemes 1 and 2)

Step A: Displacement/Deprotection

Mixture containing 0.126 g (1.0 mmol) of (3S)-3-fluoropyrrolidine and 0.335 g (1.5 mmol) of 2-(3-bromopropoxy)-tetrahydro-2H-pyran was dissolved in 5 mL of DMF, and 414 mg (3.0 mmol) K$_2$CO$_3$ was added. The reaction mixture was stirred for 16 hours at room temperature, poured into a 5-fold excess of water. Product was extracted with EtOAc (2×15 mL), dried over Na$_2$CO$_3$, evaporated in vacuum. Residue (~0.30 g) and 0.295 g (1.550 mmol) PTSA was dissolved in 20 mL of MeOH, stirred for 16 hours at room temperature, evaporated in vacuo, dissolved in 20 ml, of 20% aq. K$_2$CO$_3$. Product was extracted with EtOAc, the organic layer was concentrated in vacuo and purified by column chromatography (silica gel, CHCl$_3$/MeOH+NH$_3$, 20:1). Yield: 0.143 g (crude product).

Step B: Chloride Formation 0.143 g (1.2 mmol) of thionyl chloride was added to a solution (ice bath) of 0.143 g (1.0 mmol) of 3-[(3S)-3-fluoropyrrolidin-1-yl]propan-1-ol. The reaction mixture was stirred for 2 h at 50° C. and concentrated in vacuo to give 0.103 g (50%, 3 steps) of (3S)-1-(3-chloropropyl)-3-fluoropyrrolidine.

The remainder of the synthesis was conducted in a manner analogous to Example 1 using the above prepared (3S)-1-(3-chloropropyl)-3-fluoropyrrolidine in the final step. $^1$H NMR (400 MHz, DMSO-d$_6$): 2.05-2.45 (6H, m), 3.05-3.30 (4H, m), 3.55-3.75 (2H, m), 4.02 (2H, dd, J=6.85 Hz, J=6.85 Hz), 4.05-4.16 (2H, m), 6.92 (1H, dd, J=7.1 Hz, J=2.2 Hz), 7.07 (1H, d, J=2.2 Hz), 7.87 (1H, d, J=7.1 Hz), 8.25 (1H, d, J=1.2 Hz), 8.50 (1H, d, J=1.2 Hz), 8.72 (1H, s), 9.09 (1H, d, J=2.2 Hz), 9.24 (1H, dd, J=6.35 Hz, J=6.35 Hz), 9.68 (1H, J=2.2 Hz), 9.85-10.22 (1H, very br s). LC-MS APCI: m/z 549.0 [M+H]$^+$.

The following examples were prepared in an analogous manner to that described in Examples 1 and 2.

| Name | Example# | Structure | LCMS M + H = |
|---|---|---|---|
| 4-(6-{1-[3-(dimethylamino)propyl]-2-oxo-1,2-dihydropyridin-4-yl}pyrazolo[1,5-a]pyrimidin-3-yl)-N-(2,2,2-trifluoroethyl)thiophene-2-carboxamide | 3 | 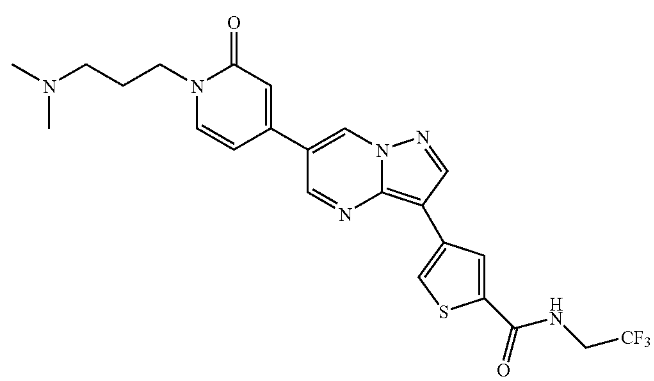 [SMILES: CN(C)CCCn1ccc(-c2cnc3c(-c4csc(C(=O)NCC(F)(F)F)c4)cnn3c2)cc1=O] | 505 |
| 4-{6-[2-oxo-1-(3-piperidin-1-ylpropyl)-1,2-dihydropyridin-4-yl]pyrazolo[1,5-a]pyrimidin-3-yl}-N-(2,2,2-trifluoroethyl)thiophene-2-carboxamide | 4 | 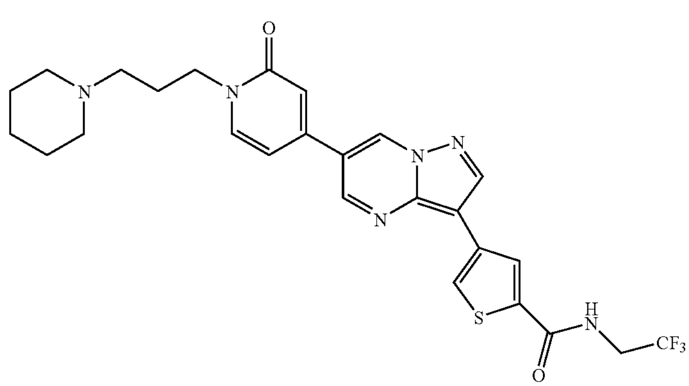 [SMILES: O=C(NCC(F)(F)F)c1cc(-c2cnn3cc(-c4ccn(CCCN5CCCCC5)c(=O)c4)cnc23)cs1] | 545 |

| Name | Example# | Structure | LCMS M + H = |
|---|---|---|---|
| 4-(6-{1-[2-(dimethylamino)ethyl]-2-oxo-1,2-dihydropyridin-4-yl}pyrazolo[1,5-a]pyrimidin-3-yl)-N-(2,2,2-trifluoroethyl)thiophene-2-carboxamide | 5 | 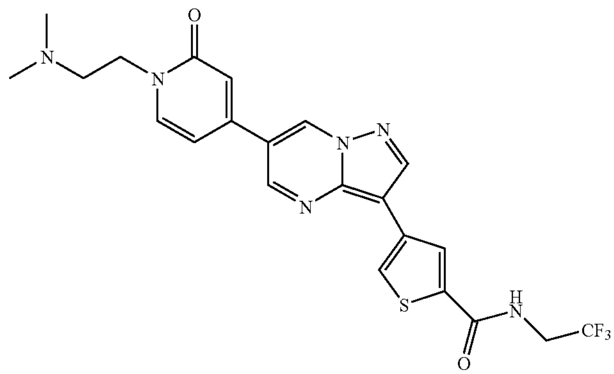 [SMILES: CN(C)CCn1ccc(-c2cnc3c(-c4csc(C(=O)NCC(F)(F)F)c4)cnn3c2)cc1=O] | 491 |
| 4-(6-{1-[3-(3-fluoropiperidin-1-yl)propyl]-2-oxo-1,2-dihydropyridin-4-yl}pyrazolo[1,5-a]pyrimidin-3-yl)-N-(2,2,2-trifluoroethyl)thiophene-2-carboxamide | 6 | 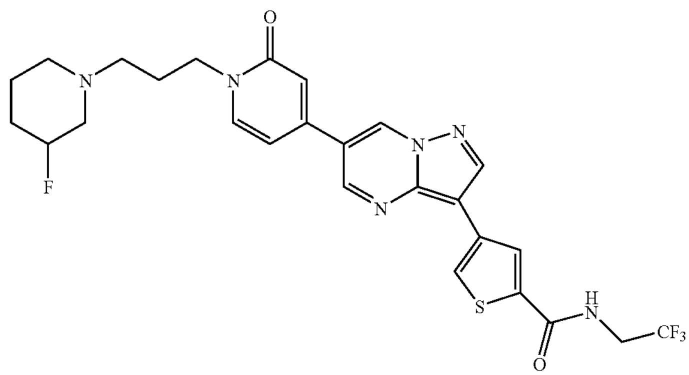 [SMILES: O=C(NCC(F)(F)F)c1cc(-c2cnn3cc(-c4ccn(CCCN5CCCC(F)C5)c(=O)c4)cnc23)cs1] | 563 |
| 4-(6-{1-[3-(3,3-difluoropiperidin-1-yl)propyl]-2-oxo-1,2-dihydropyridin-4-yl}pyrazolo[1,5-a]pyrimidin-3-yl)-N-(2,2,2-trifluoroethyl)thiophene-2-carboxamide | 7 | 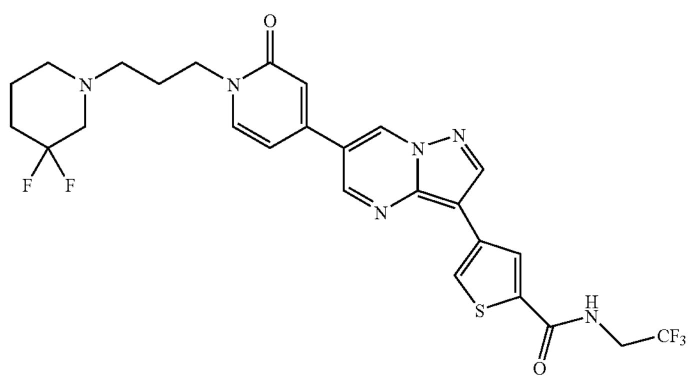 [SMILES: O=C(NCC(F)(F)F)c1cc(-c2cnn3cc(-c4ccn(CCCN5CCCC(F)(F)C5)c(=O)c4)cnc23)cs1] | 581 |
| 4-(6-{1-[3-(3,3-difluoropyrrolidin-1-yl)propyl]-2-oxo-1,2-dihydropyridin-4-yl}pyrazolo[1,5-a]pyrimidin-3-yl)-N-(2,2,2-trifluoroethyl)thiophene-2-carboxamide | 8 | 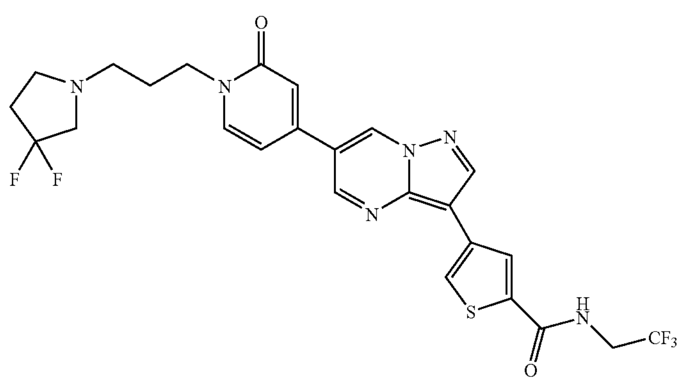 [SMILES: O=C(NCC(F)(F)F)c1cc(-c2cnn3cc(-c4ccn(CCCN5CCC(F)(F)C5)c(=O)c4)cnc23)cs1] | 567 |

| Name | Example# | Structure | LCMS M + H = |
|---|---|---|---|
| 4-[6-(1-{3-[(3R)-3-fluoropyrrolidin-1-yl]propyl}-2-oxo-1,2-dihydropyridin-4-yl)pyrazolo[1,5-a]pyrimidin-3-yl]-N-(2,2,2-trifluoroethyl)thiophene-2-carboxamide | 9 | 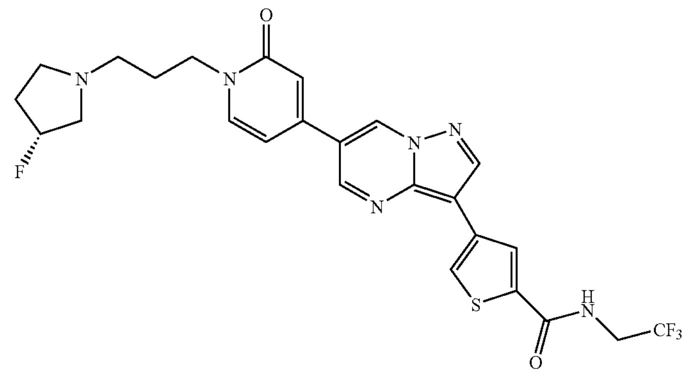 [SMILES: O=C(NCC(F)(F)F)c1cc(-c2cnn3cc(-c4ccn(CCCN5CC[C@@H](F)C5)c(=O)c4)cnc23)cs1] | 549 |
| 4-{6-[2-oxo-1-(3-pyrrolidin-1-ylpropyl)-1,2-dihydropyridin-4-yl]pyrazolo[1,5-a]pyrimidin-3-yl}-N-(2,2,2-trifluoroethyl)thiophene-2-carboxamide | 10 | 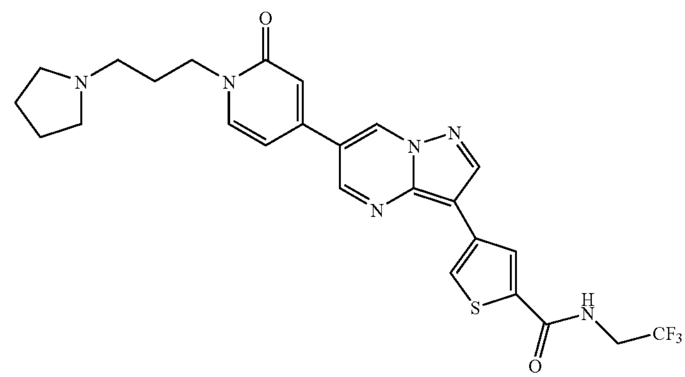 [SMILES: O=C(NCC(F)(F)F)c1cc(-c2cnn3cc(-c4ccn(CCCN5CCCC5)c(=O)c4)cnc23)cs1] | 531 |
| 4-{6-[1-(3-morpholin-4-ylpropyl)-2-oxo-1,2-dihydropyridin-4-yl]pyrazolo[1,5-a]pyrimidin-3-yl}-N-(2,2,2-trifluoroethyl)thiophene-2-carboxamide | 11 | 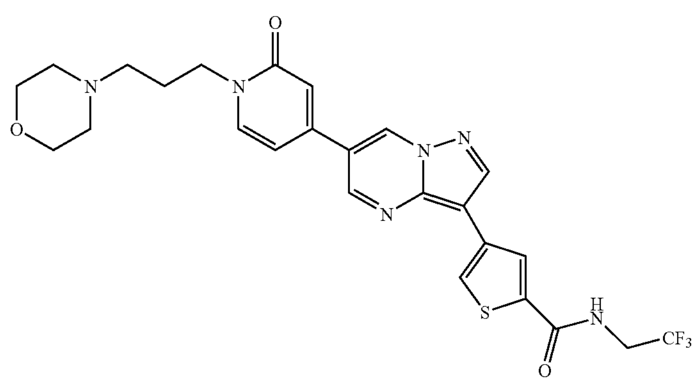 [SMILES: O=C(NCC(F)(F)F)c1cc(-c2cnn3cc(-c4ccn(CCCN5CCOCC5)c(=O)c4)cnc23)cs1] | 547 |
| 4-(6-{1-[3-(4,4-difluoropiperidin-1-yl)propyl]-2-oxo-1,2-dihydropyridin-4-yl}pyrazolo[1,5-a]pyrimidin-3-yl)-N-(2,2,2-trifluoroethyl)thiophene-2-carboxamide | 12 | 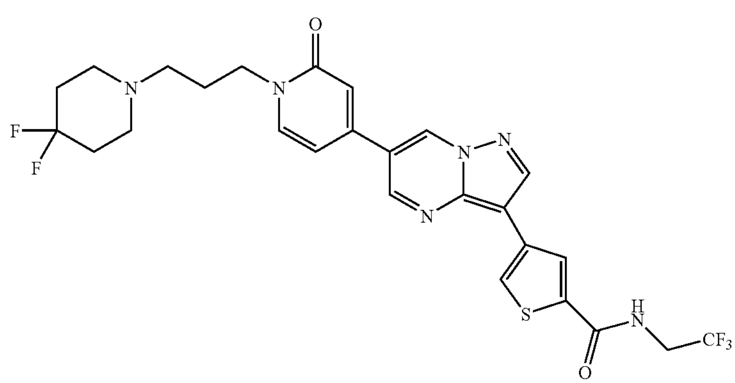 [SMILES: O=C(NCC(F)(F)F)c1cc(-c2cnn3cc(-c4ccn(CCCN5CCC(F)(F)CC5)c(=O)c4)cnc23)cs1] | 581 |

Example 13

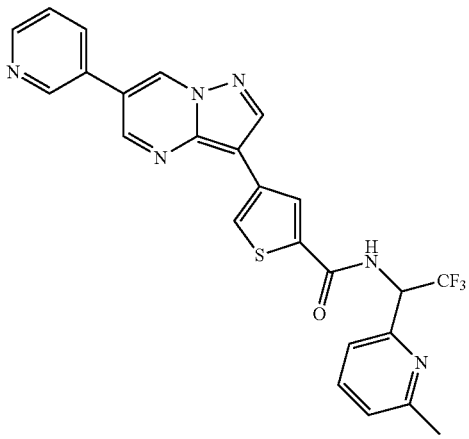 [SMILES: Cc1cccc(C(NC(=O)c2cc(-c3cnn4cc(-c5cccnc5)cnc34)cs2)C(F)(F)F)n1]

4-(6-pyridin-3-ylpyrazolo[1,5-a]pyrimidin-3-yl)-N-
[2,2,2-trifluoro-1-(6-methylpyridin-2-yl)ethyl]
thiophene-2-carboxamide (Schemes 5 and 6)

Step A: Condensation

To a solution of 2-methylpropane-2-sulfinamide (0.18 g, 1.49 mmol) in methylene chloride (3 mL) was added copper sulfate (0.24 g, 1.49 mmol) followed by 6-methylpyridine-2-carbaldehyde (0.2 g, 1.63 mmol). The reaction was stirred at ambient temperature for 16 hours, then filtered through a pad of celite (washing with methylene chloride) and evaporated in vacuo to give crude 2-methyl-N-[(1E)-(6-methylpyridin-2-yl)methylene]propane-2-sulfinamide. LC-MS EIMS: m/z 225.1 [M+H]$^+$.

Step B: Trifluoromethyl Addition

A solution of 2-methyl-N-[(1E)-(6-methylpyridin-2-yl)methylene]propane-2-sulfinamide (0.33 g, 1.48 mmol) in THF (6 mL) was added to a dry flask containing TBAT (0.88 g, 1.63 mmol) and the solution was cooled to −78° C. under a nitrogen atmosphere. To this was added trimethyl(trifluoromethyl)silane (0.26 mL, 1.78 mmol) and the reaction was warmed to −20° C. for 2 hours. The reaction was quenched with ammonium chloride solution and partitioned between water and ethyl acetate. The organic layer was dried over sodium sulfate, filtered and evaporated in vacuo. Purification by flash chromatography (5-40% ethyl acetate/hexane) gave 2-methyl-N-[2,2,2-trifluoro-1-(6-methylpyridin-2-yl)ethyl]propane-2-sulfinamide. LC-MS EIMS: m/z 295.1 [M+H]$^+$.

Step C: Deprotection

A solution of 2-methyl-N-[2,2,2-trifluoro-1-(6-methylpyridin-2-yl)ethyl]propane-2-sulfinamide (0.2 g, 0.68 mmol) in methanol (1.4 mL) was treated with (0.5 mL of a 4M solution, 2.0 mmol) and the reaction was heated to 38° C. for 16 hours. The reaction was cooled to room temperature and partitioned between water/ethyl acetate. The organics were dried over sodium sulfate, filtered and evaporated in vacuo. Purification by reverse phase chromatography gave 2,2,2-trifluoro-1-(6-methylpyridin-2-yl)ethanamine. LC-MS EIMS: m/z 191.1 [M+H]$^+$.

Step D: Suzuki Coupling

A solution of 3-pyridyl boronic acid (1.33 g, 10.8 mmol) and 3,6-dibromopyrazolo[1,5-a]pyrimidine (3.0 g, 10.8 mmol) in DMF (300 mL) and 1M aqueous sodium bicarbonate (22 mL, 22 mmol) was degassed with nitrogen and treated with palladium tetrakistriphenylphosphine (0.63 g, 0.54 mmol) and heated to 85° C. for 16 hours. The reaction was cooled to room temperature and partitioned between water/methylene chloride. The organics were washed with water and brine, dried over sodium sulfate, filtered and evaporated in vacuo. Purification by flash chromatography (1-5% methanol/methylene chloride) gave 3-bromo-6-pyridin-3-ylpyrazolo[1,5-a]pyrimidine. LC-MS EIMS: m/z 275.0 [M+H]$^+$.

Step E: Suzuki Coupling

A solution of methyl 4-(4,4,5,5-tetramethyl-1,3,2-dioxaborolan-2-yl)thiophene-2-carboxylate (1.09 g, 4.1 mmol) and 3-bromo-6-pyridin-3-ylpyrazolo[1,5-a]pyrimidine (1.1 g, 4.1 mmol) in dioxane (20 mL) and 1M aqueous sodium bicarbonate (12.2 mL, 12.2 mmol) was degassed with nitrogen and treated with palladium tetrakistriphenylphosphine (0.24 g, 0.20 mmol) and heated to 85° C. for 16 hours. The reaction was cooled to room temperature and partitioned between water/methylene chloride. The organics were washed with water and brine, dried over sodium sulfate, filtered and evaporated in vacuo. Purification by flash chromatography (1-5% methanol/methylene chloride) gave methyl 4-(6-pyridin-3-ylpyrazolo[1,5-c]pyrimidin-3-yl)thiophene-2-carboxylate. LC-MS SIMS: m/z 337.1 [M+H]$^+$.

Step F: Saponification

A solution of methyl 4-(6-pyridin-3-ylpyrazolo[1,5-a]pyrimidin-3-yl)thiophene-2-carboxylate (0.19 g, 0.57 mmol) in 9M hydrochloric acid (5.7 mL, 51 mmol) was heated to 100° C. for 16 hours. The reaction was then evaporated in vacuo and azeotroped with acetonitrile to give 4-(6-pyridin-3-ylpyrazolo[1,5-c]pyrimidin-3-yl)thiophene-2-carboxylic acid as it's crude HCl salt. LC-MS EIMS: m/z 323.0 [M+H]$^+$.

Step G: Amide Coupling

A solution of 4-(6-pyridin-3-ylpyrazolo[1,5-a]pyrimidin-3-yl)thiophene-2-carboxylic acid hydrochloride (20 mg, 0.06 mmol), 2,2,2-trifluoro-1-(6-methylpyridin-2-yl)ethanamine (step C, 12 mg, 0.06 mmol), BOP (41 mg, 0.09 mmol) and N,N-diisopropylethylamine (16 □L, 0.09 mmol) in DMF (0.6 mL) was stirred at 40° C. for 4 hours. The reaction was partitioned between water and ethyl acetate. The organics were dried over sodium sulfate, filtered and evaporated in vacuo. Purification by reverse phase LC gave 4-(6-pyridin-3-ylpyrazolo[1,5-a]pyrimidin-3-yl)-N-[2,2,2-trifluoro-1-(6-methylpyridin-2-yl)ethyl]thiophene-2-carboxamide. $^1$H NMR (600 MHz, CDCl$_3$): δ 9.42 (bs, 1H), 9.11 (s, 1H), 9.00 (d, J=2.4 Hz, 1H), 8.84 (d, J=5.3 Hz, 1H), 8.81 (d, J=2.3 Hz, 1H), 8.55 (s, 2H), 8.34 (d, J=8.3 Hz, 1H), 8.17 (s, 1H), 7.99 (t, J=8.5 Hz, 1H), 7.85 (dd, J=7.9, 5.3 Hz, 1H), 7.58 (d, J=7.4 Hz, 1H), 7.48 (m, 1H), 6.13 (m, 1H), 3.48 (s, 3H). LC-MS EIMS: m/z 495.1 [M+H]$^+$.

The following examples were prepared in an analogous manner to that described in Example 13, using the appropriate aldehyde in Step A and the appropriate boronic acid in Step D.

| Name | Example# | Structure | LCMS M + H = |
|---|---|---|---|
| N-[(1R)-2-methyl-1-(trifluoromethyl)propyl]-4-(6-pyridin-4-ylpyrazolo[1,5-a]pyrimidin-3-yl)thiophene-2-carboxamide | 14 | 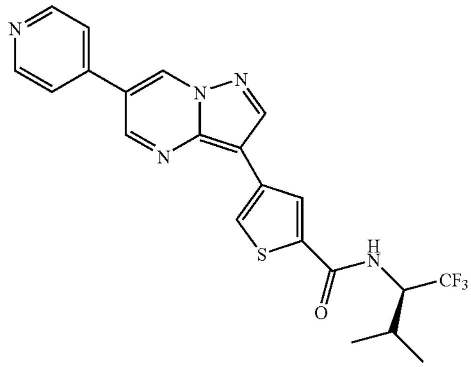 [SMILES: CC(C)[C@@H](NC(=O)c1cc(-c2cnn3cc(-c4ccncc4)cnc23)cs1)C(F)(F)F] | 446 |
| N-[(1R)-2-methyl-1-(trifluoromethyl)propyl]-4-(6-pyridin-3-ylpyrazolo[1,5-a]pyrimidin-3-yl)thiophene-2-carboxamide | 15 | 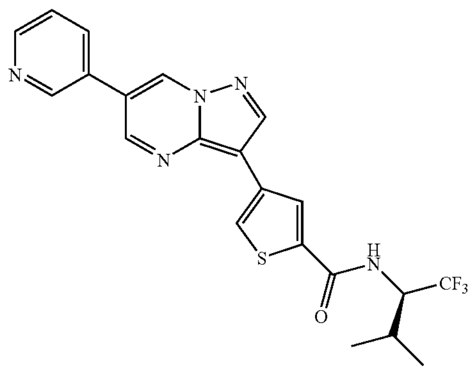 [SMILES: CC(C)[C@@H](NC(=O)c1cc(-c2cnn3cc(-c4cccnc4)cnc23)cs1)C(F)(F)F] | 446 |
| N-[(1R)-2-methyl-1-(trifluoromethyl)propyl]-4-(6-pyridin-2-ylpyrazolo[1,5-a]pyrimidin-3-yl)thiophene-2-carboxamide | 16 | 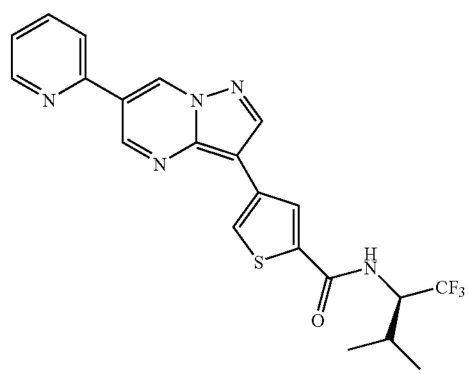 [SMILES: CC(C)[C@@H](NC(=O)c1cc(-c2cnn3cc(-c4ccccn4)cnc23)cs1)C(F)(F)F] | 446 |

Example 17

4-(6-quinolin-6-ylpyrazolo[1,5-a]pyrimidin-3-yl)-N-(2,2,2-trifluoro-1-pyridin-2-ylethyl)thiophene-2-carboxamide (Schemes 3 and 7)

Step A: Amide Coupling

A mixture of 4-bromo-2-thiophenecarboxylic acid (1 eq) and BOP (1.2 eq) in DMF (10 mL) was stirred over a period of 15 min. Diisopropylethylamine (3 eq) and the corresponding amine 2,2,2-trifluoro-1-pyridin-2-ylethanamine (1.2 eq) were added. The mixture was stirred overnight at room temperature. The DMF was distilled off. The residue was subjected to coevaporation with xylene, washed with water, 5% NaHCO$_3$, brine, and dried. 4-Bromo-N-(2,2,2-trifluoro-1-pyridin-2-ylethyl)thiophene-2-carboxamide was obtained by column chromatography (dichloromethane-hexane, 10:1).

Step B: Pinacolediborane Coupling

A flask with a solution of the 4-bromo-N-(2,2,2-trifluoro-1-pyridin-2-ylethyl)thiophene-2-carboxamide (1 eq), bis-pinacolediborane (1.3 eq), Pd(dppf)Cl$_2$ (0.03 eq), dppf (0.03 eq), and KOAc (3 eq) in 10 mL of dioxane was degassed three times. The reaction mixture was stirred over a period of 30 h at 90-100° C. The mixture was evaporated, and the residue was dissolved in chloroform. The solution was filtered through Celite, washed with 10% NaHCO$_3$, and then with water. The organic layer was separated and evaporated to give 4-(4,4,5,5-tetramethyl-1,3,2-dioxaborolan-2-yl)-N-(2,2,2-trifluoro-1-pyridin-2-ylethyl)thiophene-2-carboxamide.

Step C: Bromination

3-Dimethylaminoacrolein (1.98 g, 20 mmol) was dissolved in benzene (20 mL). Br$_2$ (1.07 mL, 21 mmol) was added dropwise slowly at 15° C. The obtained curds-like mass was stirred for 16 h. The solid phase was filtered off, washed on the filter with benzene, and transferred into a beaker. A 20% solution of K$_2$CO$_3$ and benzene were added.

The organic layer was separated. The aqueous one was washed twice more with benzene. The combined organic phases were washed with brine and concentrated to give (2Z)-2-bromo-3-(dimethylamino)acrylaldehyde.

Step D: Condensation

3-Aminopyrazole (0.75 g, 9.04 mmol) was mixed with (2Z)-2-bromo-3-(dimethylamino)acrylaldehyde obtained at the previous step (1.85 g, 10.4 mmol). Absolute ethanol (20 mL) and glacial acetic acid (2 mL) were added. The reaction mixture was stirred under reflux for 16 h and evaporated to dryness. The residue was washed on a filter with cold ethanol/hexane mixture (3:1) and dried in a vacuum oven at 30° C. to give 6-bromopyrazolo[1,5-a]pyrimidine.

Step E: Iodination

A mixture of compound 6-bromopyrazolo[1,5-a]pyrimidine (1 eq), ceric ammonium nitrate (0.6 eq), and $I_2$ (0.6 eq) in acetonitrile (10 mL) was stirred over a period of 24 h at room temperature. The formed precipitate was filtered off, washed with acetonitrile, and recrystallized from acetonitrile. The filtrate was evaporated, and the product was extracted with dichloromethane. The latter was evaporated, and the residue was recrystallized from acetonitrile to give 6-bromo-3-iodopyrazolo[1,5-a]pyrimidine.

Step F: Suzuki Coupling 6-bromo-3-iodopyrazolo[1,5-a]pyrimidine (1 eq) was mixed with 4-(4,4,5,5-tetramethyl-1,3,2-dioxaborolan-2-yl)-N-(2,2,2-trifluoro-1-pyridin-2-ylethyl)thiophene-2-carboxamide (1 eq, step B). Dioxane (10 mL) and 1M $Na_2CO_3$ (2 eq) were added. The mixture was evacuated and flushed with nitrogen under stirring, then Pd(Ph$_3$P)$_4$ (0.05 eq) was added in a flow of nitrogen. The temperature was brought to 90° C. The reaction mixture was stirred at this temperature overnight and concentrated. The residue was poured into a 5-fold excess of water. The mixture was extracted with chloroform. The organic layer was washed with brine, dried with MgSO$_4$, and concentrated. The residue was purified by column chromatography (dichloromethane-methanol, 100:1) to give 4-(6-bromopyrazolo[1,5-a]pyrimidin-3-yl)-N-(2,2,2-trifluoro-1-pyridin-2-ylethyl)thiophene-2-carboxamide.

Step G: Suzuki Coupling 4-(6-bromopyrazolo[1,5-a]pyrimidin-3-yl)-N-(2,2,2-trifluoro-1-pyridin-2-ylethyl)thiophene-2-carboxamide (1 eq) was mixed with quinolin-6-ylboronic acid (1.3 eq). Dioxane (10 mL) and 1M $Na_2CO_3$ (2 eq) were added. The mixture was evacuated and flushed with nitrogen under stirring, then a solution Pd(Ph$_3$P)$_4$ (0.05 eq) in dioxane was added under inert gas. The temperature was brought to 100° C. The reaction mixture was stirred at this temperature overnight. The reaction mixtures were filtered through Celite, and the latter was washed with methanol. Purification by reverse phase LC gave 4-(6-quinolin-6-ylpyrazolo[1,5-c]pyrimidin-3-yl)-N-(2,2,2-trifluoro-1-pyridin-2-ylethyl)thiophene-2-carboxamide. $^1$H NMR (400 MHz, DMSO-d$_6$): 6.11-6.22 (1H, m), 7.47-7.52 (1H, m), 7.67 (1H, dd, J=8.3 Hz, J=4.4 Hz), 7.81 (1H, d, J=7.8 Hz), 7.93-7.98 (1H, m), 8.19 (1H, d, J=8.8 Hz), 8.32 (1H, d, J=1.2 Hz), 8.34 (1H, dd, J=8.8 Hz, J=1.95 Hz), 8.48-8.53 (1H, m), 8.59 (1H, d, J=1.95 Hz), 8.67-8.70 (1H, m), 8.72 (1H, s), 8.76 (1H, d, J=1.2 Hz), 9.00 (1H, dd, J=4.4 Hz, J=1.7 Hz), 9.26 (1H, d, J=2.2 Hz), 9.54 (1H, d, J=9.3 Hz), 9.71 (1H, d, J=2.2 Hz). LC-MS APCI: m/z 531.0 [M+H]$^+$.

The following examples were prepared in an analogous manner to that described in Example 17, using the appropriate amine in Step A and the appropriate boronic acid in Step G.

| Name | Example# | Structure | LCMS M + H = |
|---|---|---|---|
| 4-(6-pyridin-3-ylpyrazolo[1,5-a]pyrimidin-3-yl)-N-(2,2,2-trifluoroethyl)thiophene-2-carboxamide | 18 | 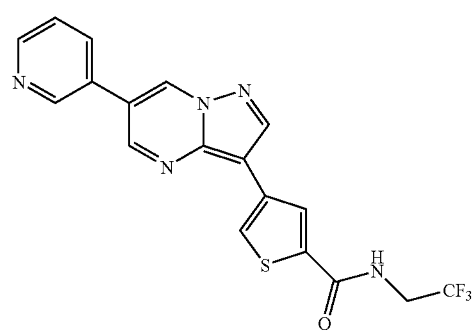 [SMILES: O=C(NCC(F)(F)F)c1cc(-c2cnn3cc(-c4cccnc4)cnc23)cs1] | 404 |
| 4-[6-(1-methyl-1H-indol-5-yl)pyrazolo[1,5-a]pyrimidin-3-yl]-N-(2,2,2-trifluoroethyl)thiophene-2-carboxamide | 19 | 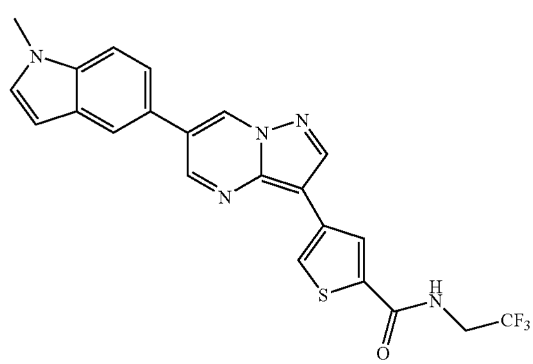 [SMILES: Cn1ccc2cc(-c3cnc4c(-c5csc(C(=O)NCC(F)(F)F)c5)cnn4c3)ccc21] | 456 |

| Name | Example# | Structure | LCMS M + H = |
|---|---|---|---|
| 4-[6-(1-methyl-1H-pyrazol-5-yl)pyrazolo[1,5-a]pyrimidin-3-yl]-N-(2,2,2-trifluoroethyl)thiophene-2-carboxamide | 20 | 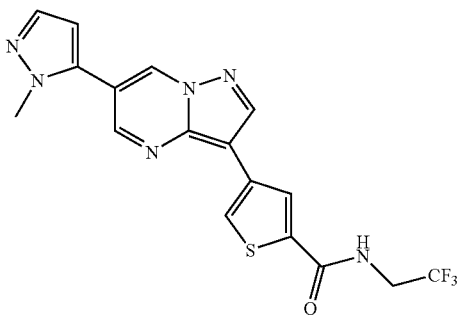 [SMILES: Cn1nccc1-c1cnc2c(-c3csc(C(=O)NCC(F)(F)F)c3)cnn2c1] | 407 |
| 4-[6-(1-methyl-1H-imidazol-4-yl)pyrazolo[1,5-a]pyrimidin-3-yl]-N-(2,2,2-trifluoroethyl)thiophene-2-carboxamide | 21 | 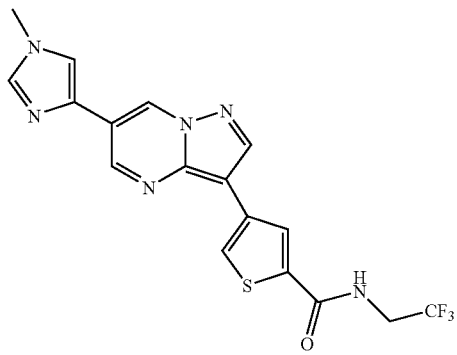 [SMILES: Cn1cnc(-c2cnc3c(-c4csc(C(=O)NCC(F)(F)F)c4)cnn3c2)c1] | 407 |
| 4-[6-(1-benzofuran-5-yl)pyrazolo[1,5-a]pyrimidin-3-yl]-N-(2,2,2-trifluoroethyl)thiophene-2-carboxamide | 22 | 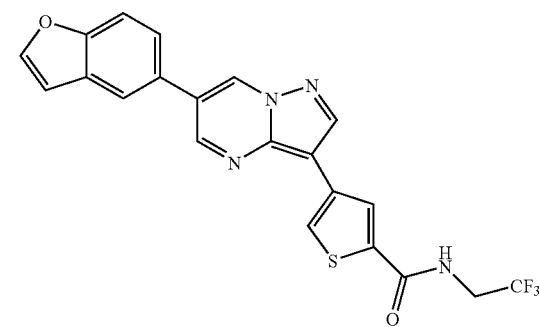 [SMILES: O=C(NCC(F)(F)F)c1cc(-c2cnn3cc(-c4ccc5occc5c4)cnc23)cs1] | 443 |
| 4-[6-(1H-indol-5-yl)pyrazolo[1,5-a]pyrimidin-3-yl]-N-(2,2,2-trifluoroethyl)thiophene-2-carboxamide | 23 | 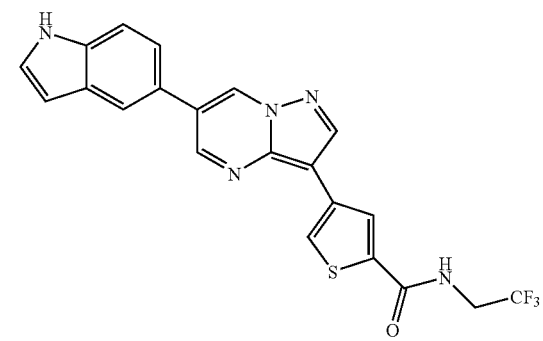 [SMILES: O=C(NCC(F)(F)F)c1cc(-c2cnn3cc(-c4ccc5[nH]ccc5c4)cnc23)cs1] | 442 |

| Name | Example# | Structure | LCMS M + H = |
|---|---|---|---|
| 4-[6-(1-methyl-1H-pyrazol-4-yl)pyrazolo[1,5-a]pyrimidin-3-yl]-N-(2,2,2-trifluoroethyl)thiophene-2-carboxamide | 24 | 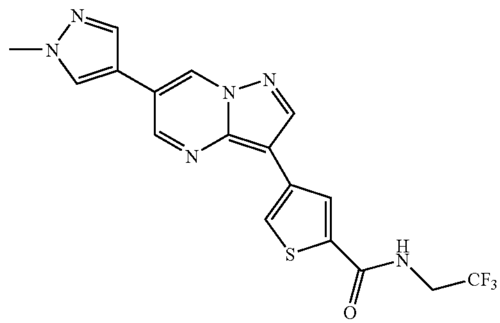 [SMILES: Cn1cc(-c2cnc3c(-c4csc(C(=O)NCC(F)(F)F)c4)cnn3c2)cn1] | 407 |
| 4-[6-(1-benzyl-1H-pyrazol-4-yl)pyrazolo[1,5-a]pyrimidin-3-yl]-N-(2,2,2-trifluoroethyl)thiophene-2-carboxamide | 25 | 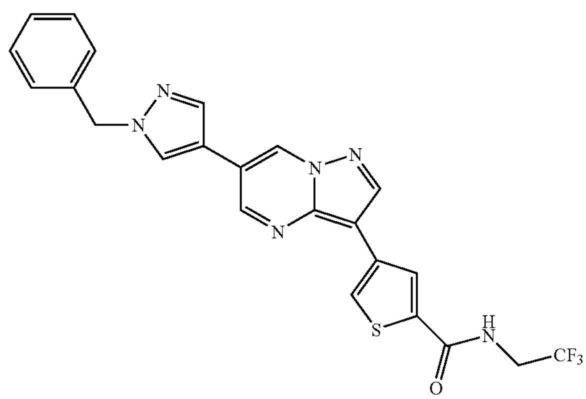 [SMILES: O=C(NCC(F)(F)F)c1cc(-c2cnn3cc(-c4cnn(Cc5ccccc5)c4)cnc23)cs1] | 483 |
| 4-{6-[6-(dimethylamino)pyridin-3-yl]pyrazolo[1,5-a]pyrimidin-3-yl}-N-(2,2,2-trifluoroethyl)thiophene-2-carboxamide | 26 | 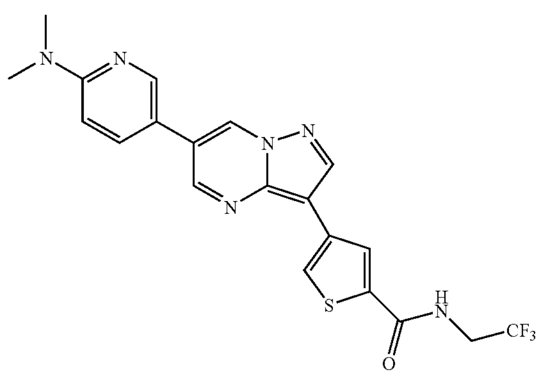 [SMILES: CN(C)c1ccc(-c2cnc3c(-c4csc(C(=O)NCC(F)(F)F)c4)cnn3c2)cn1] | 447 |
| 4-[6-(6-aminopyridin-3-yl)pyrazolo[1,5-a]pyrimidin-3-yl]-N-(2,2,2-trifluoroethyl)thiophene-2-carboxamide | 27 | 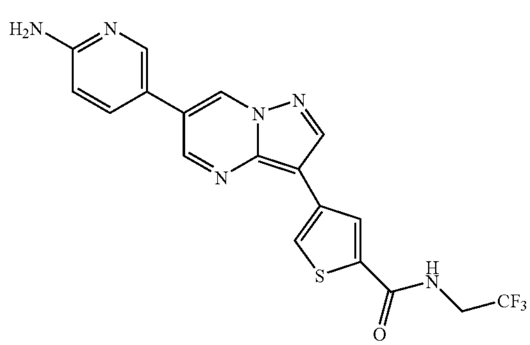 [SMILES: Nc1ccc(-c2cnc3c(-c4csc(C(=O)NCC(F)(F)F)c4)cnn3c2)cn1] | 419 |

-continued

| Name | Example# | Structure | LCMS M + H = |
|---|---|---|---|
| 4-[6-(1H-indol-6-yl)pyrazolo[1,5-a]pyrimidin-3-yl]-N-(2,2,2-trifluoroethyl)thiophene-2-carboxamide | 28 | 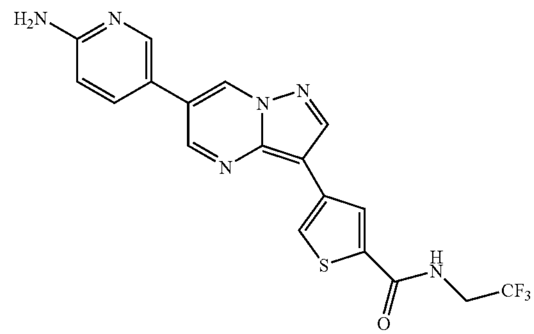 [SMILES: Nc1ccc(-c2cnc3c(-c4csc(C(=O)NCC(F)(F)F)c4)cnn3c2)cn1] | 442 |
| 4-[6-(6-piperazin-1-ylpyridin-3-yl)pyrazolo[1,5-a]pyrimidin-3-yl]-N-(2,2,2-trifluoroethyl)thiophene-2-carboxamide | 29 | 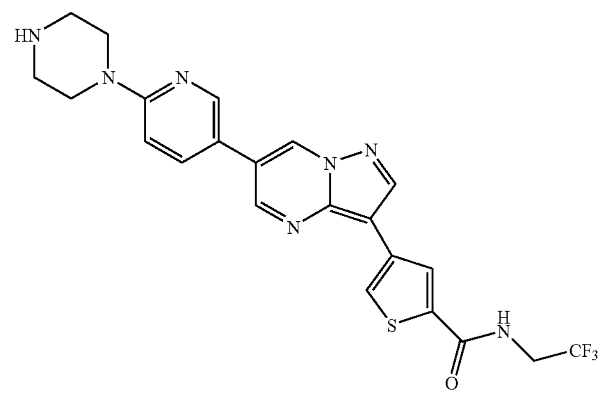 [SMILES: O=C(NCC(F)(F)F)c1cc(-c2cnn3cc(-c4ccc(N5CCNCC5)nc4)cnc23)cs1] | 488 |
| 4-(6-isoquinolin-4-ylpyrazolo[1,5-a]pyrimidin-3-yl)-N-(2,2,2-trifluoroethyl)thiophene-2-carboxamide | 30 | 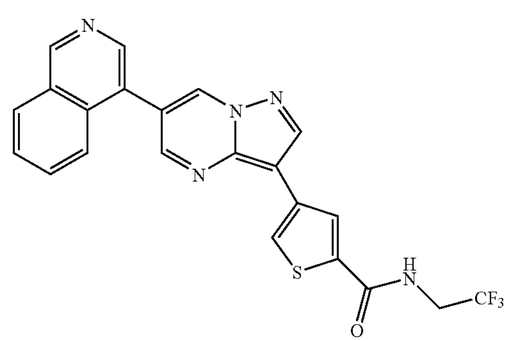 [SMILES: O=C(NCC(F)(F)F)c1cc(-c2cnn3cc(-c4cncc5ccccc45)cnc23)cs1] | 454 |
| 4-(6-quinolin-3-ylpyrazolo[1,5-a]pyrimidin-3-yl)-N-(2,2,2-trifluoroethyl)thiophene-2-carboxamide | 31 | 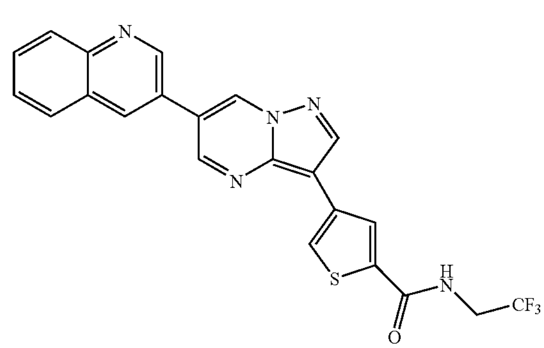 [SMILES: O=C(NCC(F)(F)F)c1cc(-c2cnn3cc(-c4cnc5ccccc5c4)cnc23)cs1] | 454 |

| Name | Example# | Structure | LCMS M + H = |
|---|---|---|---|
| 4-[6-(1H-pyrrolo[2,3-b]pyridin-5-yl)pyrazolo[1,5-a]pyrimidin-3-yl]-N-(2,2,2-trifluoroethyl)thiophene-2-carboxamide | 32 | 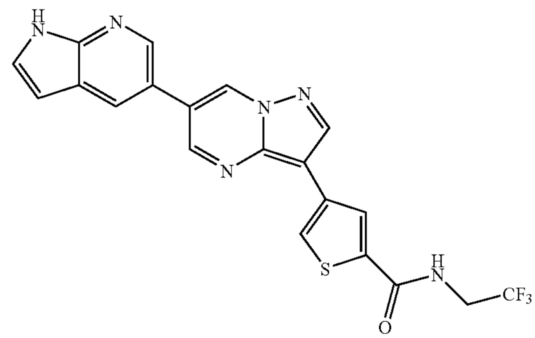 [SMILES: O=C(NCC(F)(F)F)c1cc(-c2cnn3cc(-c4cnc5[nH]ccc5c4)cnc23)cs1] | 443 |
| 4-(6-{6-[(2-morpholin-4-ylethyl)amino]pyridin-3-yl}pyrazolo[1,5-a]pyrimidin-3-yl)-N-(2,2,2-trifluoroethyl)thiophene-2-carboxamide | 33 | 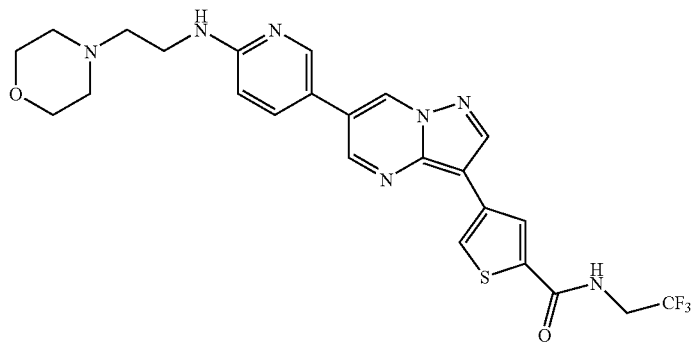 [SMILES: O=C(NCC(F)(F)F)c1cc(-c2cnn3cc(-c4ccc(NCCN5CCOCC5)nc4)cnc23)cs1] | 532 |
| 4-{6-[6-(cyclopropylmethoxy)pyridin-3-yl]pyrazolo[1,5-a]pyrimidin-3-yl}-N-(2,2,2-trifluoroethyl)thiophene-2-carboxamide | 34 | 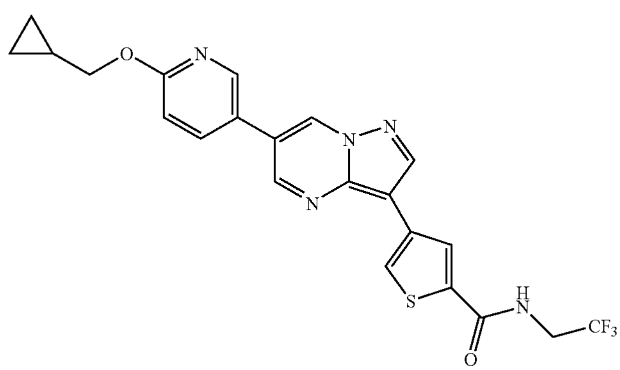 [SMILES: O=C(NCC(F)(F)F)c1cc(-c2cnn3cc(-c4ccc(OCC5CC5)nc4)cnc23)cs1] | 474 |
| 4-{6-[6-(acetylamino)pyridin-3-yl]pyrazolo[1,5-a]pyrimidin-3-yl}-N-(2,2,2-trifluoroethyl)thiophene-2-carboxamide | 35 | 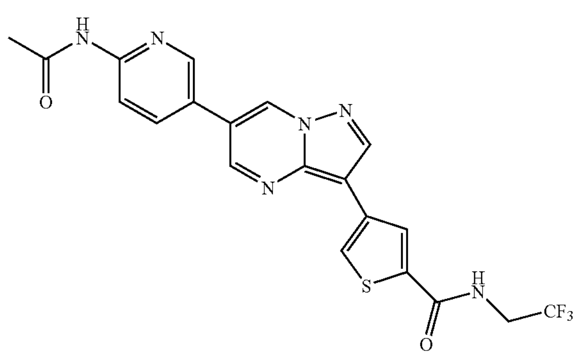 [SMILES: CC(=O)Nc1ccc(-c2cnc3c(-c4csc(C(=O)NCC(F)(F)F)c4)cnn3c2)cn1] | 461 |

-continued

| Name | Example# | Structure | LCMS M + H = |
|---|---|---|---|
| 4-[6-(1H-pyrrol-2-yl)pyrazolo[1,5-a]pyrimidin-3-yl]-N-(2,2,2-trifluoroethyl)thiophene-2-carboxamide | 36 | 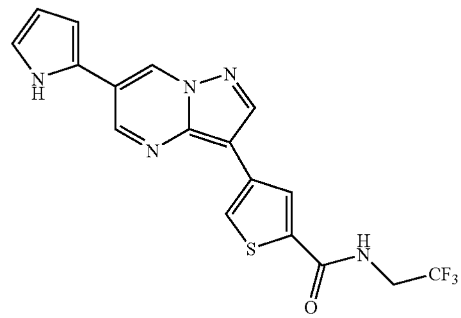 [SMILES: O=C(NCC(F)(F)F)c1cc(-c2cnn3cc(-c4ccc[nH]4)cnc23)cs1] | 392 |
| 4-[6-(1H-pyrazol-3-yl)pyrazolo[1,5-a]pyrimidin-3-yl]-N-(2,2,2-trifluoro-1-pyridin-2-ylethyl)thiophene-2-carboxamide | 37 | 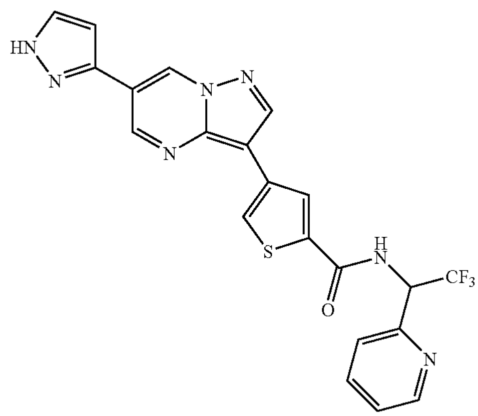 [SMILES: O=C(NC(c1ccccn1)C(F)(F)F)c1cc(-c2cnn3cc(-c4cc[nH]n4)cnc23)cs1] | 470 |
| 4-[6-(3-thienyl)pyrazolo[1,5-a]pyrimidin-3-yl]-N-(2,2,2-trifluoro-1-pyridin-2-ylethyl)thiophene-2-carboxamide | 38 | 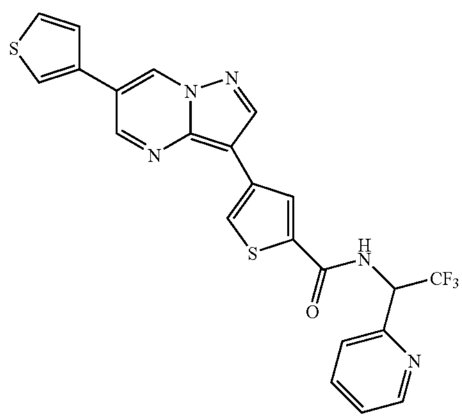 [SMILES: O=C(NC(c1ccccn1)C(F)(F)F)c1cc(-c2cnn3cc(-c4ccsc4)cnc23)cs1] | 486 |
| 4-(6-{6-[3-(dimethylamino)propoxy]pyridin-3-yl}pyrazolo[1,5-a]pyrimidin-3-yl)-N-(2,2,2-trifluoroethyl)thiophene-2-carboxamide | 39 | 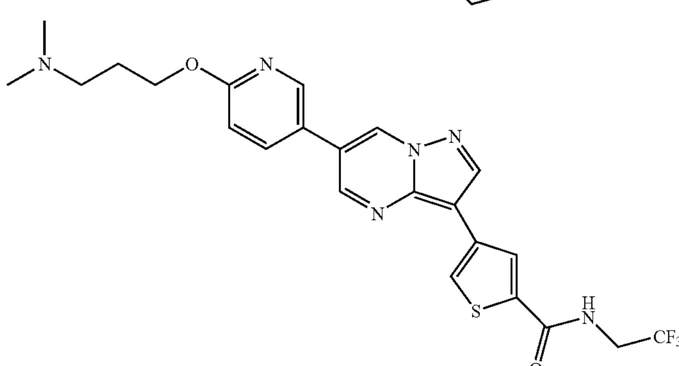 | 505 |

-continued

| Name | Example# | Structure | LCMS M + H = |
|---|---|---|---|
| 4-[6-(1-methyl-1H-imidazol-4-yl)pyrazolo[1,5-a]pyrimidin-3-yl]-N-[(1R)-2-methyl-1-(trifluoromethyl)propyl]thiophene-2-carboxamide | 40 | 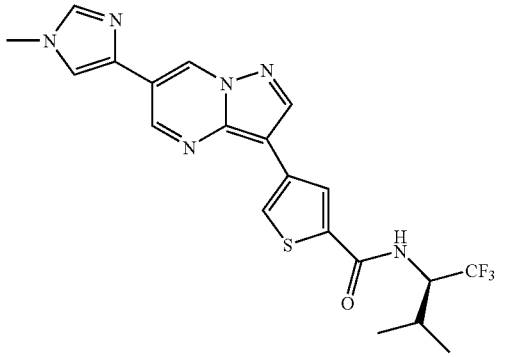 [SMILES: CC(C)[C@@H](NC(=O)c1cc(-c2cnn3cc(-c4cn(C)cn4)cnc23)cs1)C(F)(F)F] | 449 |
| 4-[6-(1,2,3,6-tetrahydropyridin-4-yl)pyrazolo[1,5-a]pyrimidin-3-yl]-N-(2,2,2-trifluoroethyl)thiophene-2-carboxamide | 41 | 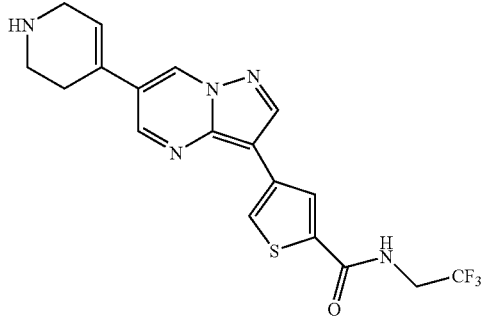 [SMILES: O=C(NCC(F)(F)F)c1cc(-c2cnn3cc(C4=CCNCC4)cnc23)cs1] | 408 |
| 4-[6-(3-furyl)pyrazolo[1,5-a]pyrimidin-3-yl]-N-(2,2,2-trifluoro-1-pyridin-2-ylethyl)thiophene-2-carboxamide | 42 | 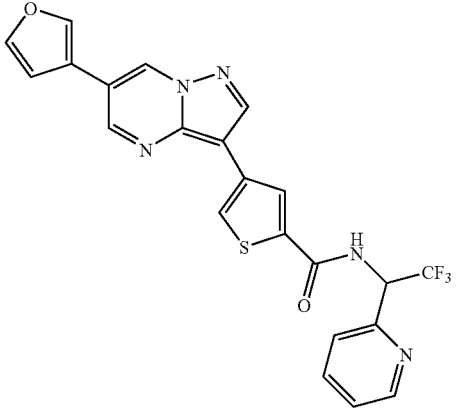 [SMILES: O=C(NC(c1ccccn1)C(F)(F)F)c1cc(-c2cnn3cc(-c4ccoc4)cnc23)cs1] | 470 |
| 4-[6-(2-furyl)pyrazolo[1,5-a]pyrimidin-3-yl]-N-(2,2,2-trifluoro-1-pyridin-2-ylethyl)thiophene-2-carboxamide | 43 | 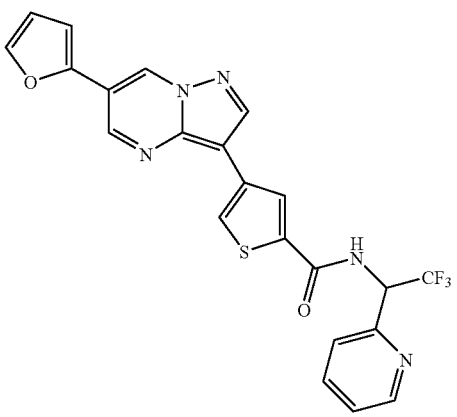 [SMILES: O=C(NC(c1ccccn1)C(F)(F)F)c1cc(-c2cnn3cc(-c4ccco4)cnc23)cs1] | 470 |

| Name | Example# | Structure | LCMS M + H = |
|---|---|---|---|
| 4-[6-(5-acetyl-2-thienyl)pyrazolo[1,5-a]pyrimidin-3-yl]-N-(2,2,2-trifluoro-1-pyridin-2-ylethyl)thiophene-2-carboxamide | 44 | 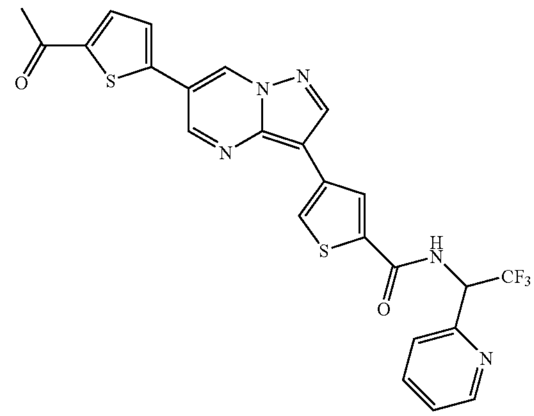 [SMILES: CC(=O)c1ccc(-c2cnc3c(-c4csc(C(=O)NC(c5ccccn5)C(F)(F)F)c4)cnn3c2)s1] | 528 |
| 4-[6-(6-methoxypyridin-3-yl)pyrazolo[1,5-a]pyrimidin-3-yl]-N-(2,2,2-trifluoroethyl)thiophene-2-carboxamide | 45 | 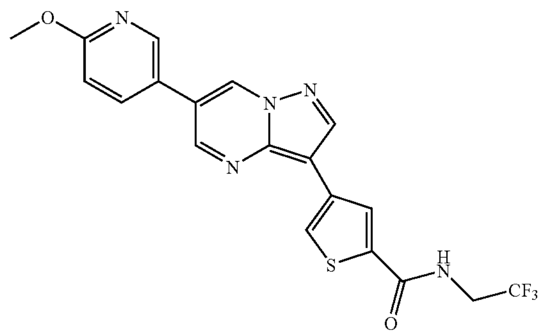 [SMILES: COc1ccc(-c2cnc3c(-c4csc(C(=O)NCC(F)(F)F)c4)cnn3c2)cn1] | 434 |
| 4-[6-(1-methyl-1H-pyrazol-4-yl)pyrazolo[1,5-a]pyrimidin-3-yl]-N-[(1R)-2-methyl-1-(trifluoromethyl)propyl]thiophene-2-carboxamide | 46 | 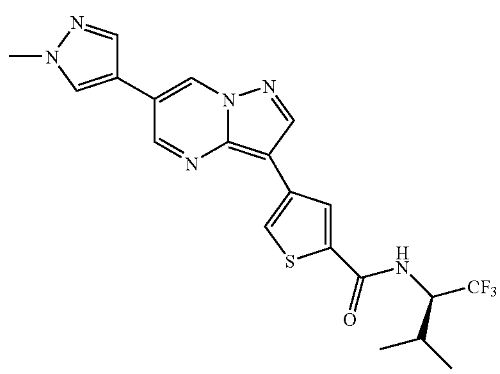 [SMILES: CC(C)[C@@H](NC(=O)c1cc(-c2cnn3cc(-c4cnn(C)c4)cnc23)cs1)C(F)(F)F] | 449 |
| N-[(1R)-2-methyl-1-(trifluoromethyl)propyl]-4-[6-(1H-pyrazol-4-yl)pyrazolo[1,5-a]pyrimidin-3-yl]thiophene-2-carboxamide | 47 | 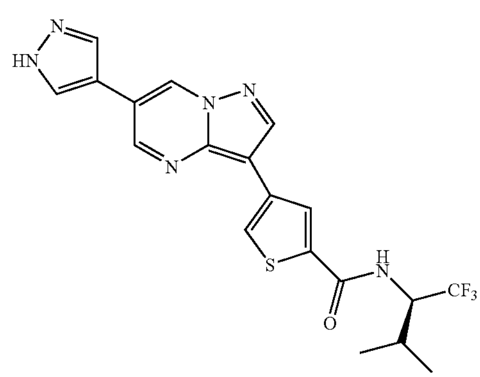 [SMILES: CC(C)[C@@H](NC(=O)c1cc(-c2cnn3cc(-c4cn[nH]c4)cnc23)cs1)C(F)(F)F] | 435 |

Example 48

4-[6-(2-oxo-2,3-dihydro-1H-benzimidazol-5-yl)pyrazolo[1,5-a]pyrimidin-3-yl]-N-(2,2,2-trifluoroethyl)thiophene-2-carboxamide (Schemes 4 and 7)

Example 49

4-(6-{6-[(2-hydroxy-2-methylpropyl)amino]pyridin-3-yl}pyrazolo[1,5-a]pyrimidin-3-yl)-N-[(1R)-2-methyl-1-(trifluoromethyl)propyl]thiophene-2-carboxamide (Schemes 6, 7 and 8)

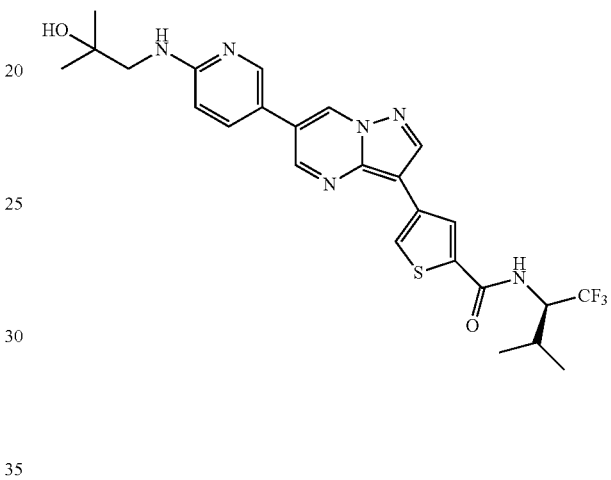

A solution of 2-nitro-5-(4,4,5,5-tetramethyl-1,3,2-dioxaborolan-2-yl)aniline (2.35 g, 8.9 mmol) in ethyl acetate (100 mL) was treated with platinum(IV) oxide (0.2 g) and stirred vigorously under a hydrogen atmosphere for 30 minutes. The reaction mixture was degassed with nitrogen and filtered through celite washing with ethyl acetate. This solution was then treated with CDI (1.8 g, 11.1 mmol) and stirred overnight at ambient temperature. The solution was diluted with methylene chloride (100 mL) and the precipate was filtered and washed with cold methanol. The solids were dried in vacuo to yield 5-(4,4,5,5-tetramethyl-1,3,2-dioxaborolan-2-yl)-1,3-dihydro-2H-benzimidazol-2-one as a white solid.

4-[6-(2-oxo-2,3-dihydro-1H-benzimidazol-5-yl)pyrazolo[1,5-a]pyrimidin-3-yl]-N-(2,2,2-trifluoroethyl)thiophene-2-carboxamide was then prepared as in step G of example 17. LC-MS EIMS: m/z 458.9 [M+H]$^+$.

Step A: Suzuki Coupling 3-bromo-6-(6-fluoropyridin-3-yl)pyrazolo[1,5-a]pyrimidine was prepared as in step D of example 13 using (6-fluoropyridin-3-yl)boronic acid.

Step B: Nucleophilic Displacement

A solution of 3-bromo-6-(6-fluoropyridin-3-yl)pyrazolo[1,5-a]pyrimidine (0.1 g, 0.34 mmol), 1-amino-2-methylpropan-2-ol (0.06 g, 0.68 mmol) and potassium carbonate (0.9 g, 0.68 mmol) in DMF (3 mL) was heated to 80° C. for 72 hours. The reaction was directly purified by reverse phase LC to give 1-{[5-(3-bromopyrazolo[1,5-a]pyrimidin-6-yl)pyridin-2-yl]amino}-2-methylpropan-2-ol. LC-MS EIMS: m/z 364.0 [M+H]$^+$.

Step C: Suzuki Coupling 4-(6-{6-[(2-hydroxy-2-methylpropy)amino]pyridin-3-yl}pyrazolo[1,5-a]pyrimidin-3-yl)-N-[(1R)-2-methyl-1-(trifluoromethyl)propyl]thiophene-2-carboxamide was prepared as in step G of example 17 using N-[(1R)-2-methyl-1-(trifluoromethyl)propyl]-4-(4,4,5,5-tetramethyl-1,3,2-dioxaborolan-2-yl)thiophene-2-carboxamide (prepared according to steps A and B, example 17 using (2R)-1,1,1-trifluoro-3-methylbutan-2-amine). LC-MS EIMS: m/z 533.1 [M+H]$^+$.

The following examples were prepared in an analogous manner to that described in Example 49.

| Name | Example | Structure | LCMS M + H = |
|---|---|---|---|
| 4-[6-(6-morpholin-4-ylpyridin-3-yl)pyrazolo[1,5-a]pyrimidin-3-yl]-N-(2,2,2-trifluoroethyl)thiophene-2-carboxamide | 50 | 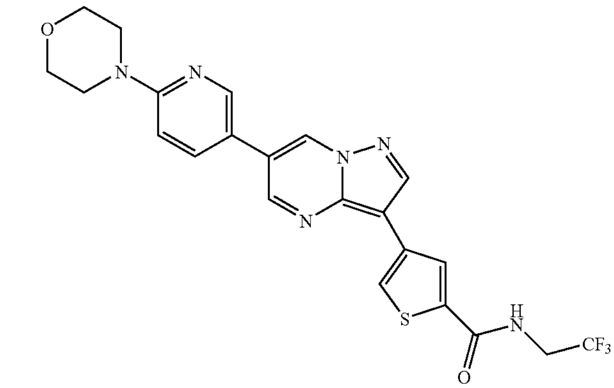 [SMILES: O=C(NCC(F)(F)F)c1cc(-c2cnn3cc(-c4ccc(N5CCOCC5)nc4)cnc23)cs1] | 489 |
| 4-(6-{6-[(2-methoxyethyl)amino]pyridin-3-yl}pyrazolo[1,5-a]pyrimidin-3-yl)-N-[(1R)-2-methyl-1-(trifluoromethyl)propyl]thiophene-2-carboxamide | 51 | 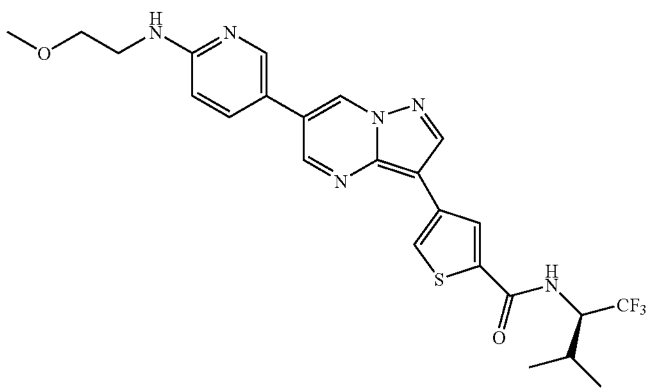 [SMILES: COCCNc1ccc(-c2cnc3c(-c4csc(C(=O)N[C@H](C(C)C)C(F)(F)F)c4)cnn3c2)cn1] | 519 |

Using analogous methods, the following further examples were prepared:

| Name | Example | Structure | LCMS M + H = |
|---|---|---|---|
| 4-(6-pyridin-3-ylpyrazolo[1,5-a]pyrimidin-3-yl)-N-[2,2,2-trifluoro-1-(5-fluoropyridin-2-yl)ethyl]thiophene-2-carboxamide | 52 | 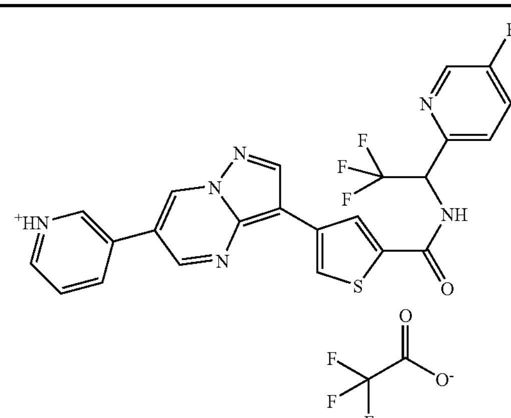 | 499 |

-continued

| Name | Example | Structure | LCMS M + H = |
|---|---|---|---|
| N-[(1R)-2-methyl-1-(trifluoromethyl)propyl]-4-[6-(6-morpholin-4-ylpyridin-3-yl)pyrazolo[1,5-a]pyrimidin-3-yl]thiophene-2-carboxamide | 53 | 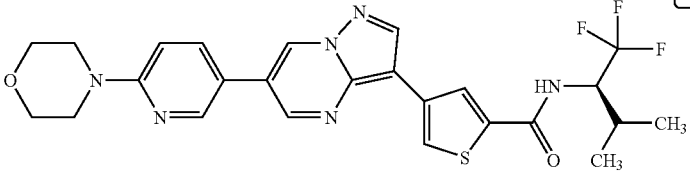 | 531 |
| 6-(1-methyl-1H-pyrazol-4-yl)-3-(5-{[2-(trifluoromethyl)pyrrolidin-1-yl]carbonyl}-3-thienyl)pyrazolo[1,5-a]pyrimidine | 54 | 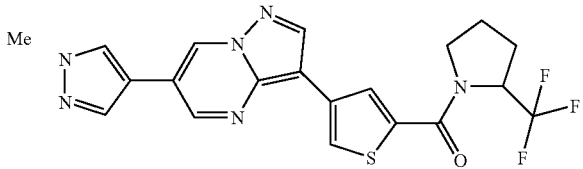 [SMILES: "Me" ; O=C(c1cc(-c2cnn3cc(-c4cn[nH]c4)cnc23)cs1)N1CCCC1C(F)(F)F] | 447 |
| 6-(1-methyl-1H-pyrazol-4-yl)-3-(5-{[(2S)-2-(trifluoromethyl)pyrrolidin-1-yl]carbonyl}-3-thienyl)pyrazolo[1,5-a]pyrimidine | 55 | 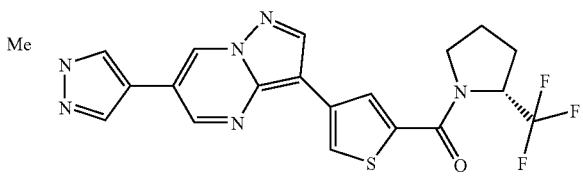 | 447 |
| 4-[6-(1H-pyrazol-4-yl)pyrazolo[1,5-a]pyrimidin-3-yl]-N-(2,2,2-trifluoroethyl)thiophene-2-carboxamide | 56 | 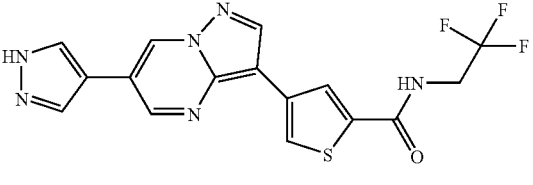 [SMILES: O=C(NCC(F)(F)F)c1cc(-c2cnn3cc(-c4cn[nH]c4)cnc23)cs1] | 393 |
| N-(2-hydroxy-2-methylpropyl)-4-[6-(1-methyl-1H-pyrazol-4-yl)pyrazolo[1,5-a]pyrimidin-3-yl]thiophene-2-carboxamide | 57 | 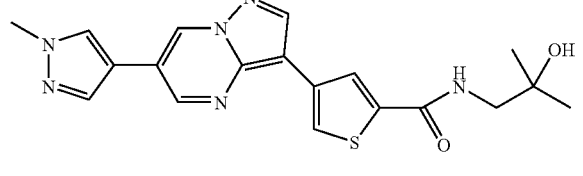 | 397 |
| N-(4-pentylphenyl)-4-(6-pyridin-3-ylpyrazolo[1,5-a]pyrimidin-3-yl)thiophene-2-carboxamide | 58 | 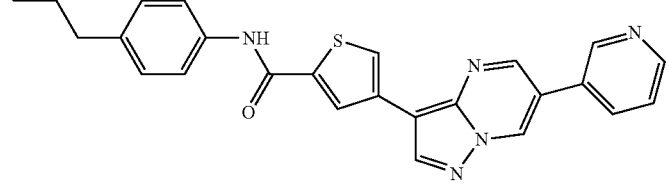 | 468 |
| N-(4-bromophenyl)-4-(6-pyridin-3-ylpyrazolo[1,5-a]pyrimidin-3-yl)thiophene-2-carboxamide | 59 | 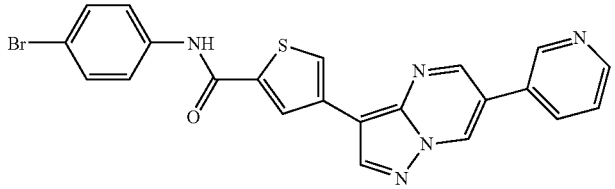 | 476 |

-continued

| Name | Example | Structure | LCMS M + H = |
|---|---|---|---|
| N-(2-fluoro-4-methylphenyl)-4-(6-pyridin-3-ylpyrazolo[1,5-a]pyrimidin-3-yl)thiophene-2-carboxamide | 60 | 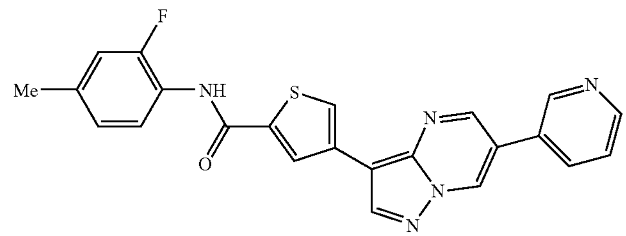 [SMILES: Cc1ccc(NC(=O)c2cc(-c3cnn4cc(-c5cccnc5)cnc34)cs2)c(F)c1] | 430 |
| N-(4-chlorophenyl)-4-(6-pyridin-3-ylpyrazolo[1,5-a]pyrimidin-3-yl)thiophene-2-carboxamide | 61 | 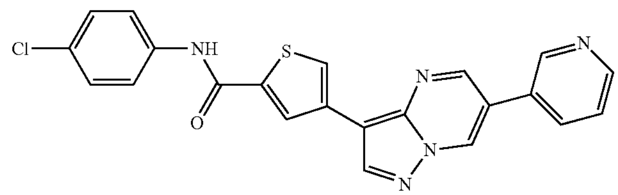 [SMILES: O=C(Nc1ccc(Cl)cc1)c1cc(-c2cnn3cc(-c4cccnc4)cnc23)cs1] | 432 |
| N-(4-methylphenyl)-4-(6-pyridin-3-ylpyrazolo[1,5-a]pyrimidin-3-yl)thiophene-2-carboxamide | 62 | 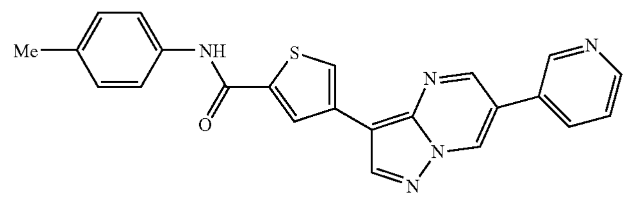 [SMILES: Cc1ccc(NC(=O)c2cc(-c3cnn4cc(-c5cccnc5)cnc34)cs2)cc1] | 412 |
| N-(4-methoxylphenyl)-4-(6-pyridin-3-ylpyrazolo[1,5-a]pyrimidin-3-yl)thiophene-2-carboxamide | 63 | 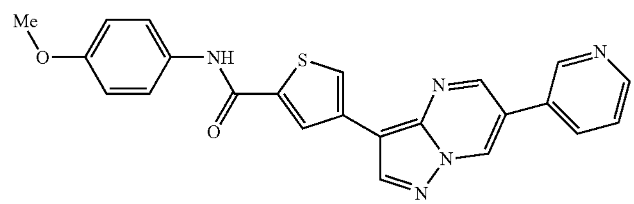 [SMILES: COc1ccc(NC(=O)c2cc(-c3cnn4cc(-c5cccnc5)cnc34)cs2)cc1] | 428 |
| 4-{6-[6-(4-methylpiperazin-1-yl)pyridin-3-yl]pyrazolo[1,5-a]pyrimidin-3-yl}-N-(2,2,2-trifluoroethyl)thiophene-2-carboxamide | 64 | 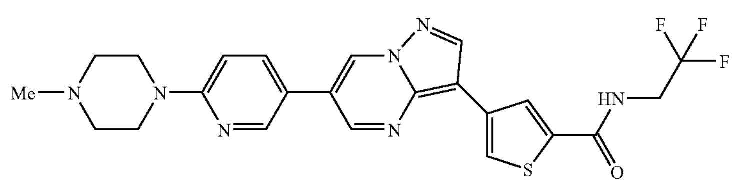 [SMILES: CN1CCN(c2ccc(-c3cnc4c(-c5csc(C(=O)NCC(F)(F)F)c5)cnn4c3)cn2)CC1] | 502 |
| N-(2-amino-2-methylpropyl)-4-[6-(1-methyl-1H-pyrazol-4-yl)pyrazolo[1,5-a]pyrimidin-3-yl]thiophene-2-carboxamide | 65 | 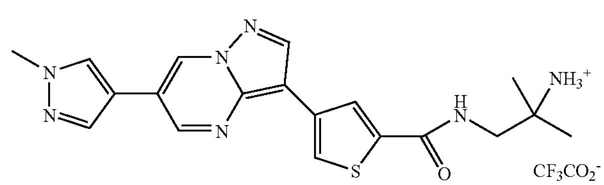 | 396 |
| N-(2-hydroxy-1-methylethyl)-4-[6-(1-methyl-1H-pyrazol-4-yl)pyrazolo[1,5-a]pyrimidin-3-yl]thiophene-2-carboxamide | 66 | 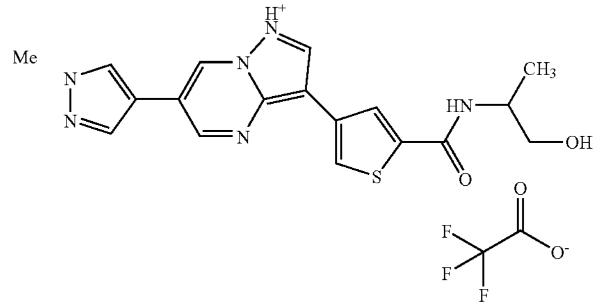 [SMILES: "Me" ; CC(CO)NC(=O)c1cc(-c2c[nH+]n3cc(-c4cn[nH]c4)cnc23)cs1 ; O=C([O-])C(F)(F)F] | 383 |

-continued

| Name | Example | Structure | LCMS M + H = |
|---|---|---|---|
| N-(1,2-dimethylpropyl)-4-[6-(1-methyl-1H-pyrazol-4-yl)pyrazolo[1,5-a]pyrimidin-3-yl]thiophene-2-carboxamide | 67 | 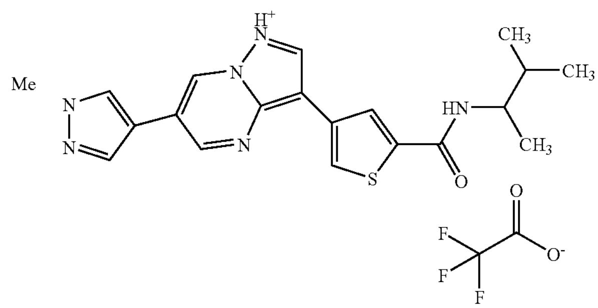 [SMILES: "Me" ; CC(C)C(C)NC(=O)c1cc(-c2c[nH+]n3cc(-c4cn[nH]c4)cnc23)cs1 ; O=C([O-])C(F)(F)F] | 395 |
| N-(1-ethylpropyl)-4-[6-(1-methyl-1H-pyrazol-4-yl)pyrazolo[1,5-a]pyrimidin-3-yl]thiophene-2-carboxamide | 68 | 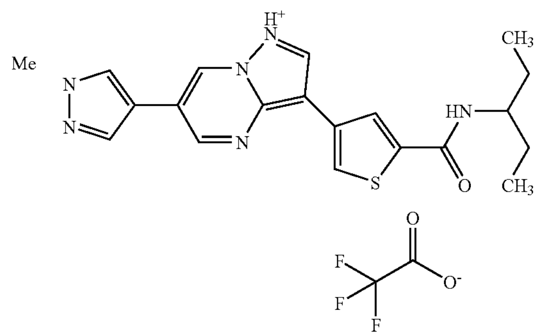 [SMILES: "Me" ; CCC(CC)NC(=O)c1cc(-c2c[nH+]n3cc(-c4cn[nH]c4)cnc23)cs1 ; O=C([O-])C(F)(F)F] | 395 |
| N-cyclopentyl-4-[6-(1-methyl-1H-pyrazol-4-yl)pyrazolo[1,5-a]pyrimidin-3-yl]thiophene-2-carboxamide | 69 | 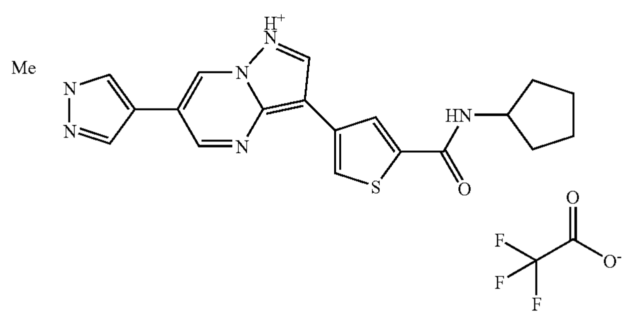 [SMILES: "Me" ; O=C(NC1CCCC1)c1cc(-c2c[nH+]n3cc(-c4cn[nH]c4)cnc23)cs1 ; O=C([O-])C(F)(F)F] | 393 |
| N-cyclopropyl-4-[6-(1-methyl-1H-pyrazol-4-yl)pyrazolo[1,5-a]pyrimidin-3-yl]thiophene-2-carboxamide | 70 | 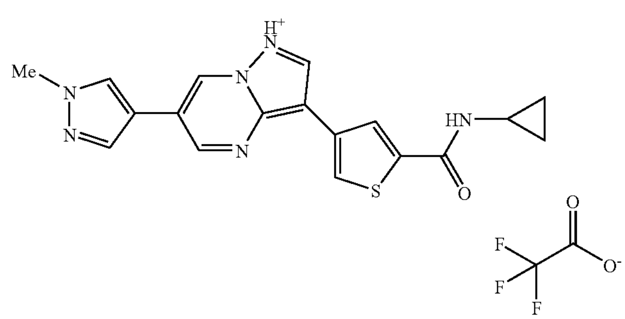 [SMILES: Cn1cc(-c2cnc3c(-c4csc(C(=O)NC5CC5)c4)c[nH+]n3c2)cn1 ; O=C([O-])C(F)(F)F] | 365 |
| N-cyclobutyl-4-[6-(1-methyl-1H-pyrazol-4-yl)pyrazolo[1,5-a]pyrimidin-3-yl]thiophene-2-carboxamide | 71 | 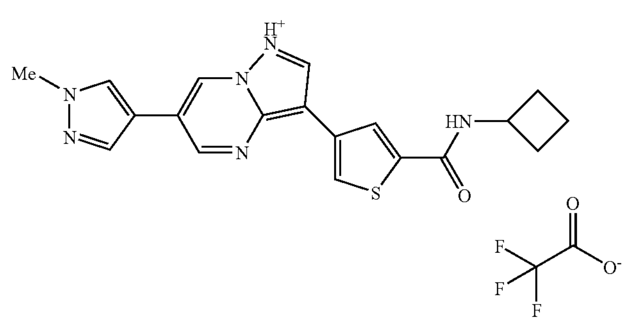 [SMILES: Cn1cc(-c2cnc3c(-c4csc(C(=O)NC5CCC5)c4)c[nH+]n3c2)cn1 ; O=C([O-])C(F)(F)F] | 379 |

-continued

| Name | Example | Structure | LCMS M + H = |
|---|---|---|---|
| N-(1-cyclopropylethyl)-4-[6-(1-methyl-1H-pyrazol-4-yl)pyrazolo[1,5-a]pyrimidin-3-yl]thiophene-2-carboxamide | 72 | 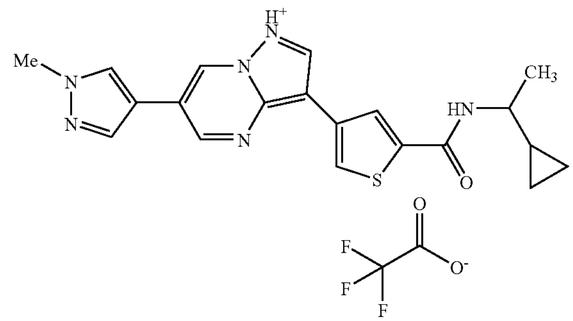 [SMILES: CC(NC(=O)c1cc(-c2c[nH+]n3cc(-c4cnn(C)c4)cnc23)cs1)C1CC1 ; O=C([O-])C(F)(F)F] | 393 |
| N-isobutyl-4-[6-(1-methyl-1H-pyrazol-4-yl)pyrazolo[1,5-a]pyrimidin-3-yl]thiophene-2-carboxamide | 73 | 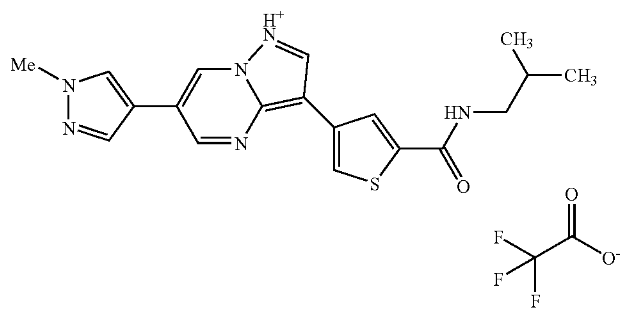 [SMILES: CC(C)CNC(=O)c1cc(-c2c[nH+]n3cc(-c4cnn(C)c4)cnc23)cs1 ; O=C([O-])C(F)(F)F] | 381 |
| 3-{5-[(3,3-difluoroazetidin-1-yl)carbonyl]-3-thienyl}-6-(1-methyl-1H-pyrazol-4-yl)pyrazolo[1,5-a]pyrimidine | 74 | 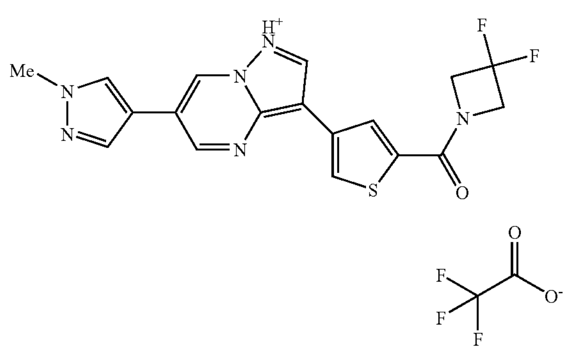 [SMILES: Cn1cc(-c2cnc3c(-c4csc(C(=O)N5CC(F)(F)C5)c4)c[nH+]n3c2)cn1 ; O=C([O-])C(F)(F)F] | 401 |
| N-isopropyl-4-[6-(1-methyl-1H-pyrazol-4-yl)pyrazolo[1,5-a]pyrimidin-3-yl]thiophene-2-carboxamide | 75 | 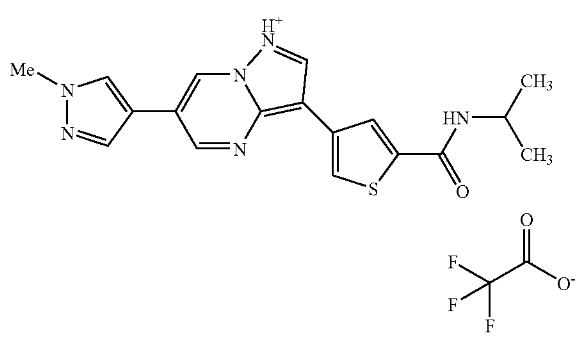 [SMILES: CC(C)NC(=O)c1cc(-c2c[nH+]n3cc(-c4cnn(C)c4)cnc23)cs1 ; O=C([O-])C(F)(F)F] | 367 |

| Name | Example | Structure | LCMS M + H = |
|---|---|---|---|
| N-ethyl-4-[6-(1-methyl-1H-pyrazol-4-yl)pyrazolo[1,5-a]pyrimidin-3-yl]thiophene-2-carboxamide | 76 | 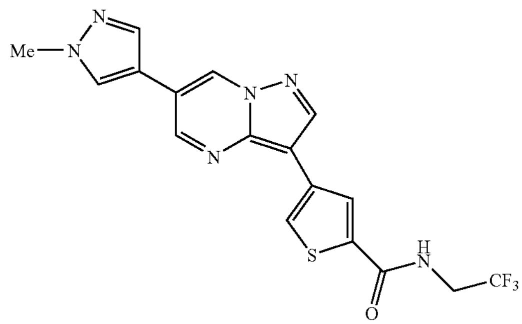 [SMILES: Cn1cc(-c2cnc3c(-c4csc(C(=O)NCC(F)(F)F)c4)cnn3c2)cn1] | 353 |
| N-[4-(cyanomethyl)phenyl]-4-(6-pyridin-3-ylpyrazolo[1,5-a]pyrimidin-3-yl)thiophene-2-carboxamide | 77 | 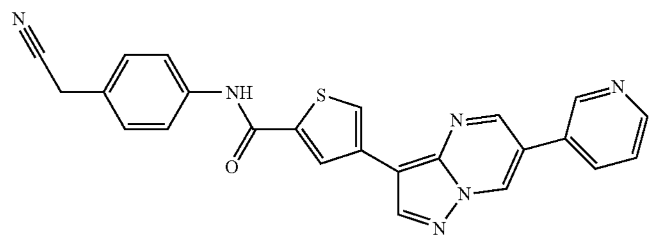 [SMILES: N#CCc1ccc(NC(=O)c2cc(-c3cnn4cc(-c5cccnc5)cnc34)cs2)cc1] | 437 |
| N-(2-methoxyethyl)-4-[6-(1-methyl-1H-pyrazol-4-yl)pyrazolo[1,5-a]pyrimidin-3-yl]thiophene-2-carboxamide | 78 | 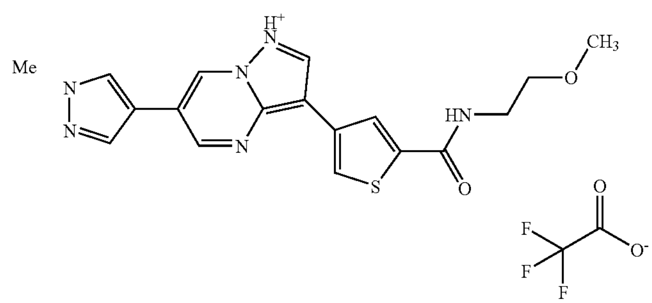 [SMILES: "Me" ; COCCNC(=O)c1cc(-c2c[nH+]n3cc(-c4cn[nH]c4)cnc23)cs1 ; O=C([O-])C(F)(F)F] | 383 |
| N-(2-hydroxyethyl)-4-[6-(1-methyl-1H-pyrazol-4-yl)pyrazolo[1,5-a]pyrimidin-3-yl]thiophene-2-carboxamide | 79 | 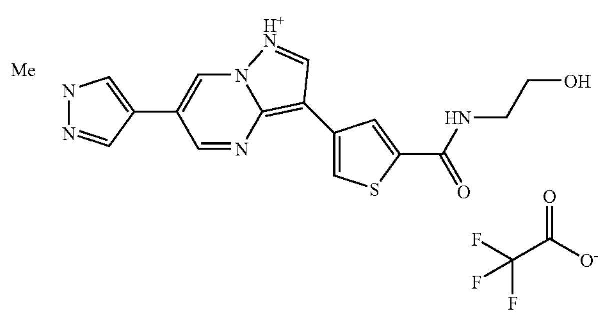 [SMILES: "Me" ; O=C(NCCO)c1cc(-c2c[nH+]n3cc(-c4cn[nH]c4)cnc23)cs1 ; O=C([O-])C(F)(F)F] | 369 |
| N-(2-hydroxycyclopentyl)-4-[6-(1-methyl-1H-pyrazol-4-yl)pyrazolo[1,5-a]pyrimidin-3-yl]thiophene-2-carboxamide | 80 | 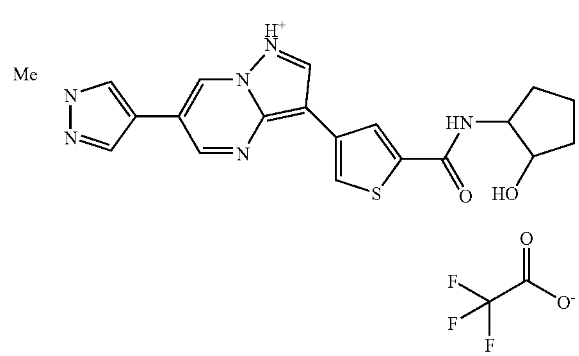 [SMILES: "Me" ; O=C(NC1CCCC1O)c1cc(-c2c[nH+]n3cc(-c4cn[nH]c4)cnc23)cs1 ; O=C([O-])C(F)(F)F] | 409 |

| Name | Example | Structure | LCMS M + H = |
|---|---|---|---|
| 4-[6-(1-methyl-1H-pyrazol-4-yl)pyrazolo[1,5-a]pyrimidin-3-yl]-N-(tetrahydrofuran-2-ylmethyl)thiophene-2-carboxamide | 81 | 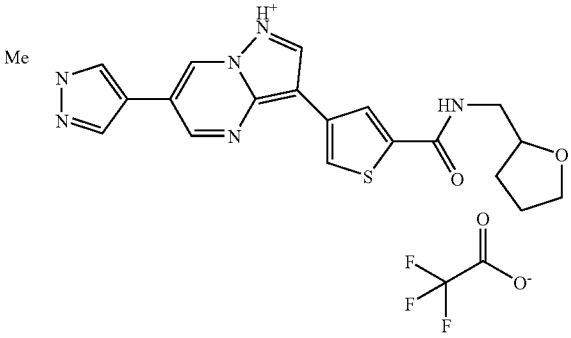 [SMILES: "Me" ; O=C(NCC1CCCO1)c1cc(-c2c[nH+]n3cc(-c4cn[nH]c4)cnc23)cs1 ; O=C([O-])C(F)(F)F] | 409 |
| N-(2-methoxy-1-methylethyl)-4-[6-(1-methyl-1H-pyrazol-4-yl)pyrazolo[1,5-a]pyrimidin-3-yl]thiophene-2-carboxamide | 82 | 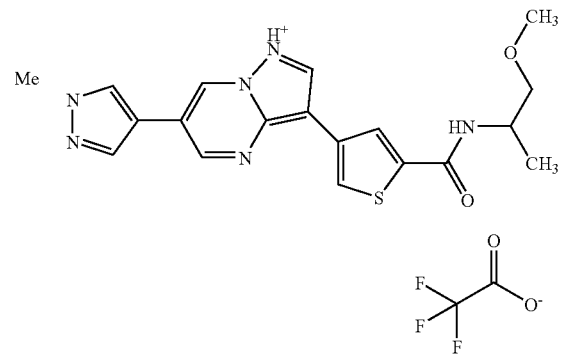 [SMILES: "Me" ; COCC(C)NC(=O)c1cc(-c2c[nH+]n3cc(-c4cn[nH]c4)cnc23)cs1 ; O=C([O-])C(F)(F)F] | 397 |
| 4-[6-(1-methyl-1H-pyrazol-4-yl)pyrazolo[1,5-a]pyrimidin-3-yl]thiophene-2-carboxamide | 83 | 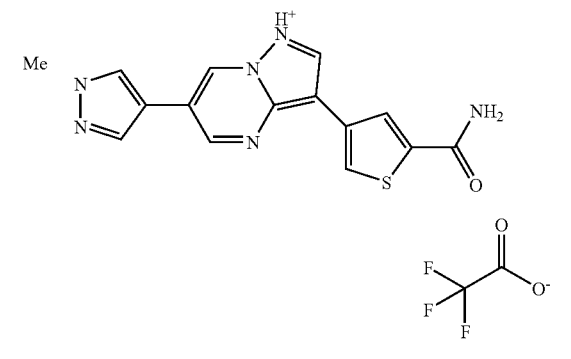 [SMILES: "Me" ; NC(=O)c1cc(-c2c[nH+]n3cc(-c4cn[nH]c4)cnc23)cs1 ; O=C([O-])C(F)(F)F] | 325 |
| N-(6-methoxypyridin-3-yl)-4-(6-pyridin-3-ylpyrazolo[1,5-a]pyrimidin-3-yl)thiophene-2-carboxamide | 84 | 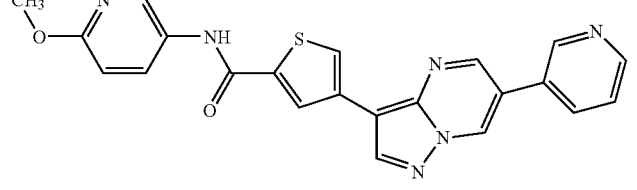 | 429 |
| 4-[6-(2,6-dimethoxypyridin-3-yl)pyrazolo[1,5-a]pyrimidin-3-yl]-N-(2,2,2-trifluoro-1-pyridin-2-ylethyl)thiophene-2-carboxamide | 85 | 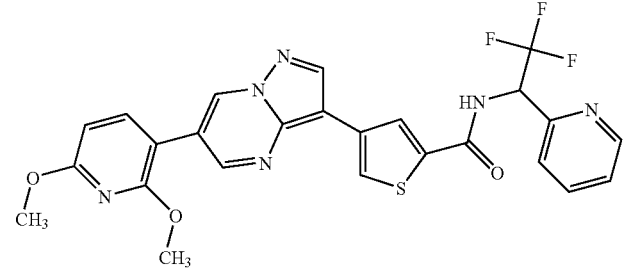 [SMILES: COc1ccc(-c2cnc3c(-c4csc(C(=O)NC(c5ccccn5)C(F)(F)F)c4)cnn3c2)c(OC)n1] | 541 |

-continued

| Name | Example | Structure | LCMS M + H = |
|---|---|---|---|
| N-(4-chloro-3-methylphenyl)-4-(6-pyridin-3-ylpyrazolo[1,5-a]pyrimidin-3-yl)thiophene-2-carboxamide | 86 | 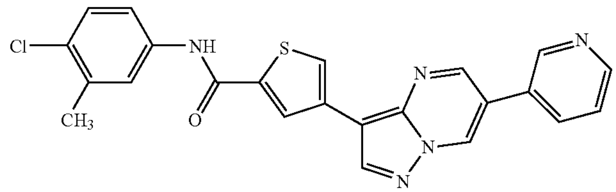 [SMILES: Cc1cc(NC(=O)c2cc(-c3cnn4cc(-c5cccnc5)cnc34)cs2)ccc1Cl] | 446 |
| N-(4-hydroxyphenyl)-4-(6-pyridin-3-ylpyrazolo[1,5-a]pyrimidin-3-yl)thiophene-2-carboxamide | 87 | 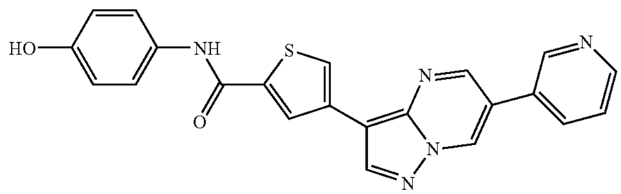 [SMILES: O=C(Nc1ccc(O)cc1)c1cc(-c2cnn3cc(-c4cccnc4)cnc23)cs1] | 414 |
| N-[5-(methylthio)-1H-1,2,4-triazol-3-yl]-4-(6-pyridin-3-ylpyrazolo[1,5-a]pyrimidin-3-yl)thiophene-2-carboxamide | 88 | 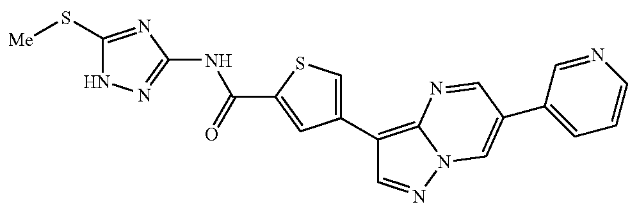 [SMILES: CSc1nc(NC(=O)c2cc(-c3cnn4cc(-c5cccnc5)cnc34)cs2)n[nH]1] | 435 |
| N-(4-bromo-2-fluorophenyl)-4-(6-pyridin-3-ylpyrazolo[1,5-a]pyrimidin-3-yl)thiophene-2-carboxamide | 89 | 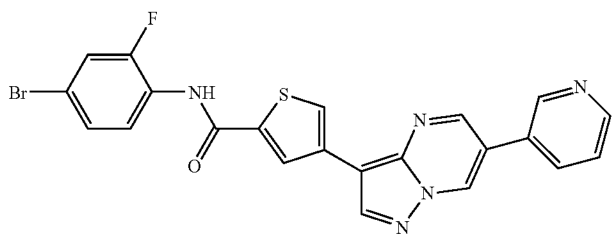 [SMILES: O=C(Nc1ccc(Br)cc1F)c1cc(-c2cnn3cc(-c4cccnc4)cnc23)cs1] | 494 |
| 4-(6-pyridin-3-ylpyrazolo[1,5-a]pyrimidin-3-yl)-N-1,3-thiazol-2-ylthiophene-2-carboxamide | 90 | 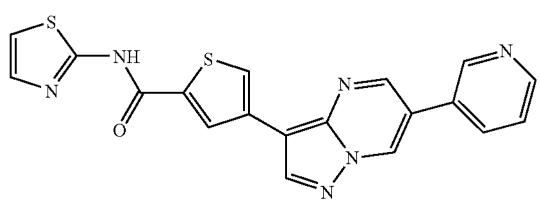 [SMILES: O=C(Nc1nccs1)c1cc(-c2cnn3cc(-c4cccnc4)cnc23)cs1] | 405 |
| N-(5-methyl-1,3-thiazol-2-yl)-4-(6-pyridin-3-ylpyrazolo[1,5-a]pyrimidin-3-yl)thiophene-2-carboxamide | 91 | 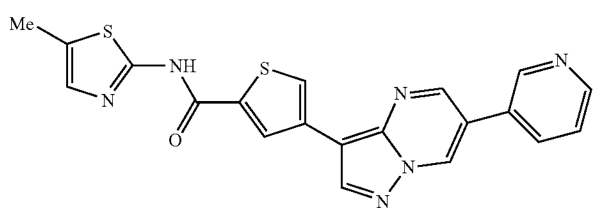 [SMILES: Cc1cnc(NC(=O)c2cc(-c3cnn4cc(-c5cccnc5)cnc34)cs2)s1] | 419 |
| N-[4-(dimethylamino)phenyl]-4-(6-pyridin-3-ylpyrazolo[1,5-a]pyrimidin-3-yl)thiophene-2-carboxamide | 92 | 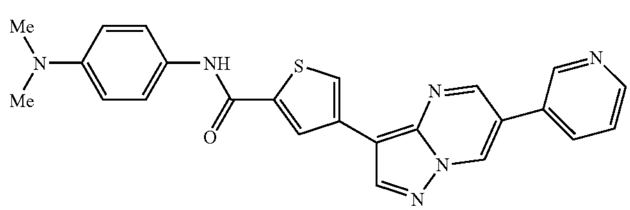 [SMILES: CN(C)c1ccc(NC(=O)c2cc(-c3cnn4cc(-c5cccnc5)cnc34)cs2)cc1] | 441 |

-continued

| Name | Example | Structure | LCMS M + H = |
|---|---|---|---|
| N-(6-methylpyridin-3-yl)-4-(6-pyridin-3-ylpyrazolo[1,5-a]pyrimidin-3-yl)thiophene-2-carboxamide | 93 | 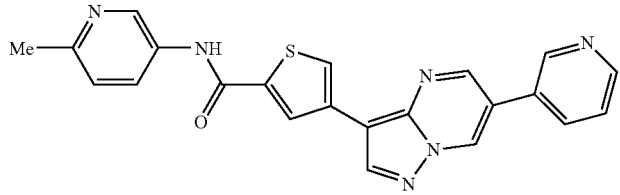 [SMILES: Cc1ccc(NC(=O)c2cc(-c3cnn4cc(-c5cccnc5)cnc34)cs2)cn1] | 413 |
| N-pyridin-3-yl-4-(6-pyridin-3-ylpyrazolo[1,5-a]pyrimidin-3-yl)thiophene-2-carboxamide | 94 | 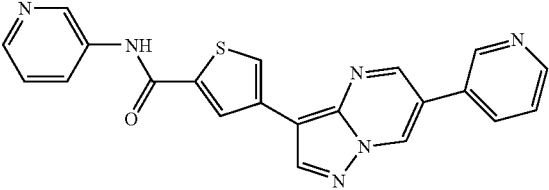 [SMILES: O=C(Nc1cccnc1)c1cc(-c2cnn3cc(-c4cccnc4)cnc23)cs1] | 399 |
| 4-(6-pyridin-3-ylpyrazolo[1,5-a]pyrimidin-3-yl)-N-[4-(trifluoromethyl)phenyl]thiophene-2-carboxamide | 95 | 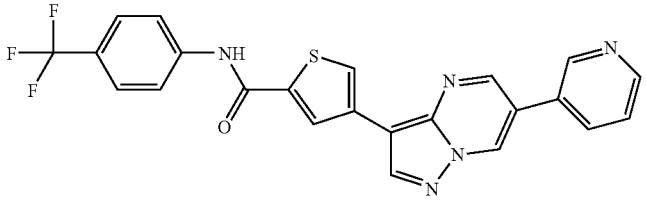 [SMILES: O=C(Nc1ccc(C(F)(F)F)cc1)c1cc(-c2cnn3cc(-c4cccnc4)cnc23)cs1] | 466 |
| N-1H-indazol-5-yl-4-(6-pyridin-3-ylpyrazolo[1,5-a]pyrimidin-3-yl)thiophene-2-carboxamide | 96 | 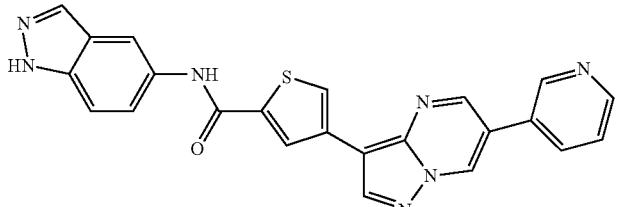 | 438 |
| N-(3-fluorophenyl)-4-(6-pyridin-3-ylpyrazolo[1,5-a]pyrimidin-3-yl)thiophene-2-carboxamide | 97 | 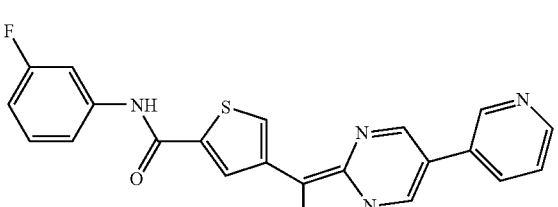 | 416 |
| N-(3-chloro-4-hydroxyphenyl)-4-(6-pyridin-3-ylpyrazolo[1,5-a]pyrimidin-3-yl)thiophene-2-carboxamide | 98 | 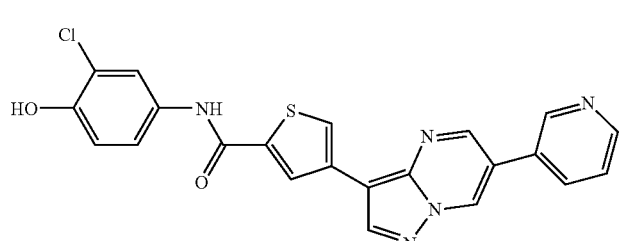 | 448 |
| N-(2-fluorophenyl)-4-(6-pyridin-3-ylpyrazolo[1,5-a]pyrimidin-3-yl)thiophene-2-carboxamide | 99 | 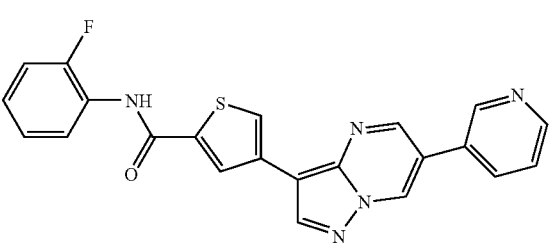 [SMILES: O=C(Nc1ccccc1F)c1cc(-c2cnn3cc(-c4cccnc4)cnc23)cs1] | 416 |

| Name | Example | Structure | LCMS M + H = |
|---|---|---|---|
| 4-[6-(1-methyl-1H-pyrazol-4-yl)pyrazolo[1,5-a]pyrimidin-3-yl]-N-(tetrahydrofuran-3-yl)thiophene-2-carboxamide | 100 | 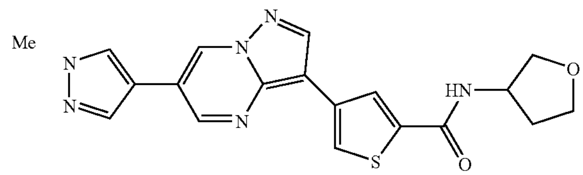 [SMILES: "Me" ; O=C(NC1CCOC1)c1cc(-c2cnn3cc(-c4cn[nH]c4)cnc23)cs1] | 395 |
| 4-[6-(1-methyl-1H-pyrazol-4-yl)pyrazolo[1,5-a]pyrimidin-3-yl]-N-(3,3,3-trifluoropropyl)thiophene-2-carboxamide | 101 | 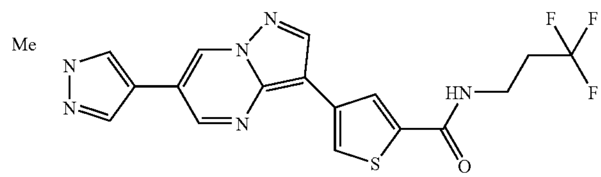 [SMILES: "Me" ; O=C(NCCC(F)(F)F)c1cc(-c2cnn3cc(-c4cn[nH]c4)cnc23)cs1] | 421 |
| 3-(5-{[(3S)-3-fluoropyrrolidin-1-yl]carbonyl}-3-thienyl)-6-(1-methyl-1H-pyrazol-4-yl)pyrazolo[1,5-a]pyrimidine | 102 | 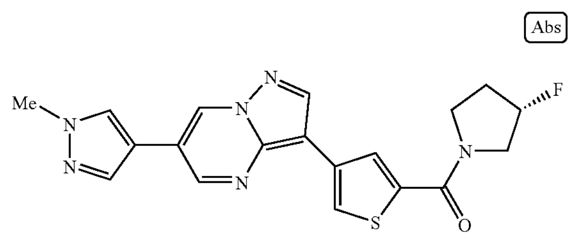 [SMILES: Cn1cc(-c2cnc3c(-c4csc(C(=O)N5CC[C@H](F)C5)c4)cnn3c2)cn1] | 397 |
| 3-{5-[(3,3-difluoropyrrolidin-1-yl)carbonyl]-3-thienyl}-6-(1-methyl-1H-pyrazol-4-yl)pyrazolo[1,5-a]pyrimidine | 103 | 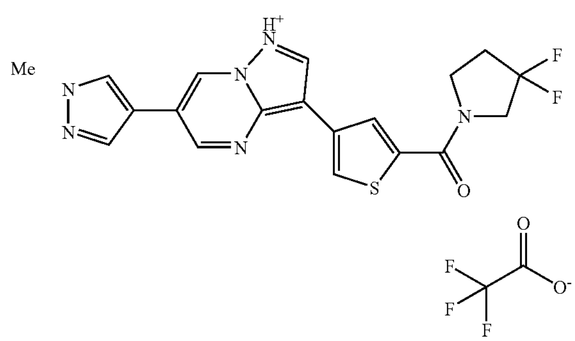 [SMILES: "Me" ; O=C(c1cc(-c2c[nH+]n3cc(-c4cn[nH]c4)cnc23)cs1)N1CCC(F)(F)C1 ; O=C([O-])C(F)(F)F] | 415 |
| N-cyclohexyl-4-[6-(1-methyl-1H-pyrazol-4-yl)pyrazolo[1,5-a]pyrimidin-3-yl]thiophene-2-carboxamide | 104 | 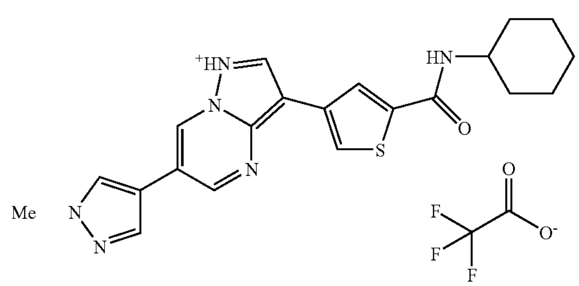 [SMILES: "Me" ; O=C(NC1CCCCC1)c1cc(-c2c[nH+]n3cc(-c4cn[nH]c4)cnc23)cs1 ; O=C([O-])C(F)(F)F] | 407 |
| 4-[6-(1-methyl-1H-pyrazol-4-yl)pyrazolo[1,5-a]pyrimidin-3-yl]-N-(3,3,3-trifluoro-2-hydroxypropyl)thiophene-2-carboxamide | 105 | 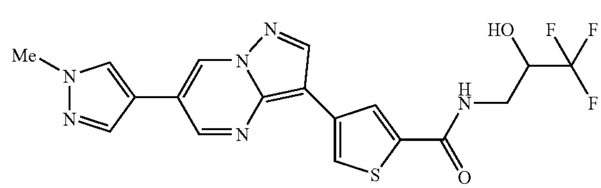 [SMILES: Cn1cc(-c2cnc3c(-c4csc(C(=O)NCC(O)C(F)(F)F)c4)cnn3c2)cn1] | 437 |

| Name | Example | Structure | LCMS M + H = |
|---|---|---|---|
| N-(3,3-difluorocyclopentyl)-4-[6-(1-methyl-1H-pyrazol-4-yl)pyrazolo[1,5-a]pyrimidin-3-yl]thiophene-2-carboxamide | 106 | 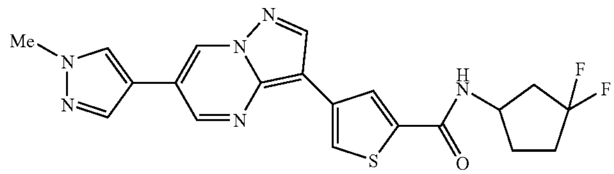 [SMILES: Cn1cc(-c2cnc3c(-c4csc(C(=O)NC5CCC(F)(F)C5)c4)cnn3c2)cn1] | 429 |
| 4-{6-[1-(3-hydroxy-3-methylbutyl)-1H-pyrazol-4-yl]pyrazolo[1,5-a]pyrimidin-3-yl}-N-(2,2,2-trifluoroethyl)thiophene-2-carboxamide | 107 | 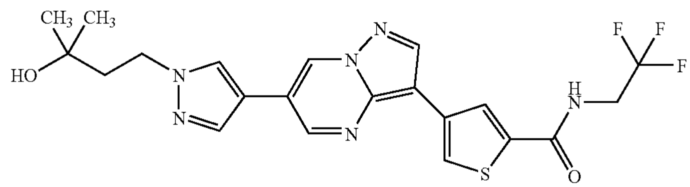 [SMILES: CC(C)(O)CCn1cc(-c2cnc3c(-c4csc(C(=O)NCC(F)(F)F)c4)cnn3c2)cn1] | 479 |
| 4-[6-(1-methyl-1H-pyrazol-4-yl)pyrazolo[1,5-a]pyrimidin-3-yl]-N-(tetrahydro-2H-pyran-4-yl)thiophene-2-carboxamide | 108 | 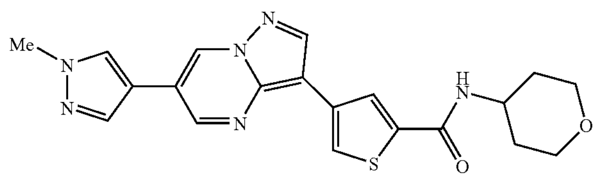 [SMILES: Cn1cc(-c2cnc3c(-c4csc(C(=O)NC5CCOCC5)c4)cnn3c2)cn1] | 409 |
| 4-[6-(1-methyl-1H-pyrazol-4-yl)pyrazolo[1,5-a]pyrimidin-3-yl]-N-(tetrahydro-2H-pyran-3-yl)thiophene-2-carboxamide | 109 | 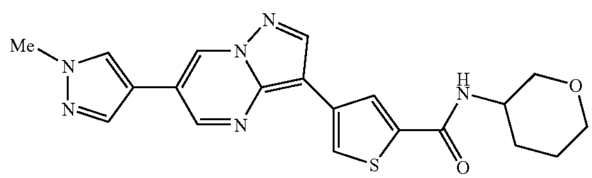 [SMILES: Cn1cc(-c2cnc3c(-c4csc(C(=O)NC5CCCOC5)c4)cnn3c2)cn1] | 409 |
| N-(1-methyl-2-oxopyrrolidin-3-yl)-4-[6-(1-methyl-1H-pyrazol-4-yl)pyrazolo[1,5-a]pyrimidin-3-yl]thiophene-2-carboxamide | 110 | 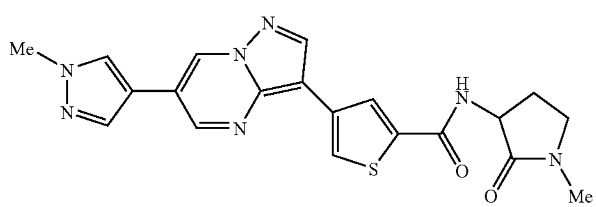 [SMILES: CN1CCC(NC(=O)c2cc(-c3cnn4cc(-c5cnn(C)c5)cnc34)cs2)C1=O] | 422 |
| 4-[6-(1-methyl-1H-pyrazol-4-yl)pyrazolo[1,5-a]pyrimidin-3-yl]-N-[(1R,2S)-2-morpholin-4-ylcyclopentyl]thiophene-2-carboxamide | 111 | 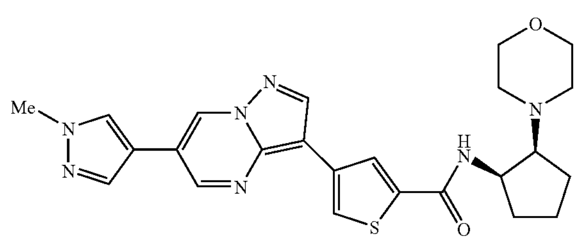 [SMILES: Cn1cc(-c2cnc3c(-c4csc(C(=O)N[C@@H]5CCC[C@@H]5N5CCOCC5)c4)cnn3c2)cn1] | 478 |
| 4-[6-(1-methyl-1H-pyrazol-4-yl)pyrazolo[1,5-a]pyrimidin-3-yl]-N-[(3R)-1-methylpyrrolidin-2-yl]thiophene-2-carboxamide | 112 | 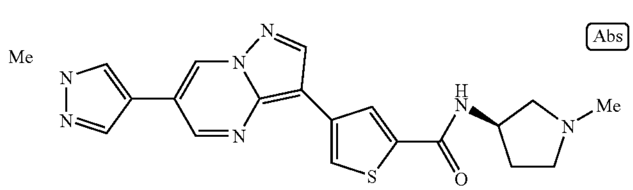 [SMILES: "Me" ; CN1CC[C@@H](NC(=O)c2cc(-c3cnn4cc(-c5cn[nH]c5)cnc34)cs2)C1] | 408 |

| Name | Example | Structure | LCMS M + H = |
|---|---|---|---|
| 4-[6-(1-methyl-1H-pyrazol-4-yl)pyrazolo[1,5-a]pyrimidin-3-yl]-N-[(3S)-1-methylpyrrolidin-3-yl]thiophene-2-carboxamide | 113 | 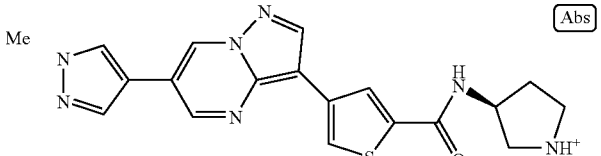 | 408 |
| N-(1-methylpiperidin-4-yl)-4-[6-(1-methyl-1H-pyrazol-4-yl)pyrazolo[1,5-a]pyrimidin-3-yl]thiophene-2-carboxamide | 114 | 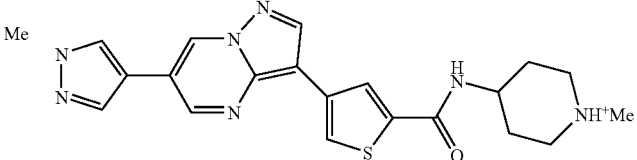 | 422 |
| 4-[6-(1-methyl-1H-pyrazol-4-yl)pyrazolo[1,5-a]pyrimidin-3-yl]-N-[(1-morpholin-4-ylcyclopentyl)methyl]thiophene-2-carboxamide | 115 | 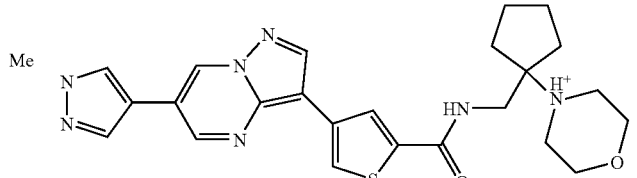 | 492 |
| N-[(3R)-1-azabicyclo[2.2.2]oct-3-yl]-4-[6-(1-methyl-1H-pyrazol-4-yl)pyrazolo[1,5-a]pyrimidin-3-yl]thiophene-2-carboxamide | 116 | 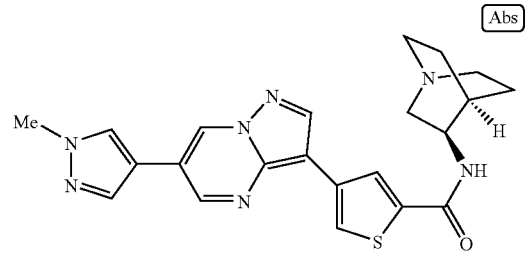 | 434 |
| 4-{6-[1-(2-morpholin-4-ylethyl)-1H-pyrazol-4-yl]pyrazolo[1,5-a]pyrimidin-3-yl}-N-(2,2,2-trifluoroethyl)thiophene-2-carboxamide | 117 | 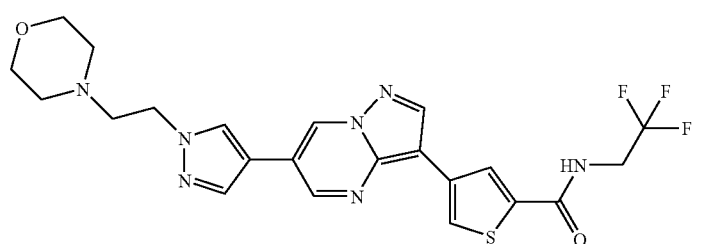 [SMILES: O=C(NCC(F)(F)F)c1cc(-c2cnn3cc(-c4cnn(CCN5CCOCC5)c4)cnc23)cs1] | 506 |

-continued

| Name | Example | Structure | LCMS M + H = |
|---|---|---|---|
| 4-[6-(1-methyl-1H-pyrazol-4-yl)pyrazolo[1,5-a]pyrimidin-3-yl]-N-[(3R)-piperidin-3-yl]thiophene-2-carboxamide | 118 | 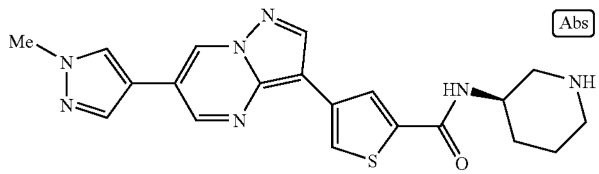 [SMILES: Cn1cc(-c2cnc3c(-c4csc(C(=O)N[C@@H]5CCCNC5)c4)cnn3c2)cn1] | 408 |
| 4-[6-(1-methyl-1H-pyrazol-4-yl)pyrazolo[1,5-a]pyrimidin-3-yl]-N-[(3S)-pyrrolidin-3-yl]thiophene-2-carboxamide | 119 | 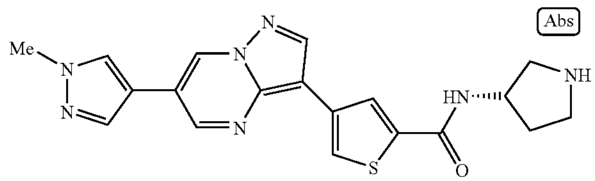 | 394 |
| N-[(3R)-1-isopropylpyrrolidin-3-yl]-4-[6-(1-methyl-1H-pyrazol-4-yl)pyrazolo[1,5-a]pyrimidin-3-yl]thiophene-2-carboxamide | 120 | 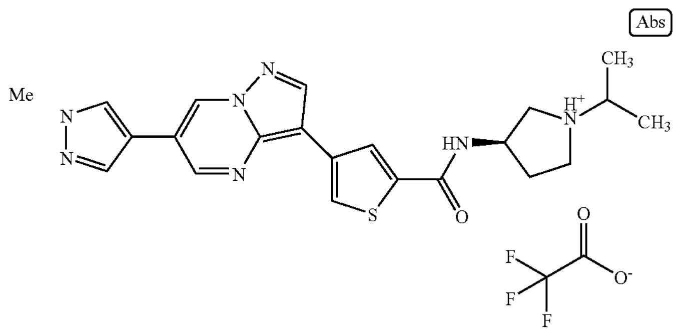 [SMILES: "Me" ; CC(C)[NH+]1CC[C@@H](NC(=O)c2cc(-c3cnn4cc(-c5cn[nH]c5)cnc34)cs2)C1 ; O=C([O-])C(F)(F)F] | 436 |
| 3-(5-{[(3S)-3-methoxypyrrolidin-1-yl]carbonyl}-3-thienyl)-6-(1-methyl-1H-pyrazol-4-yl)pyrazolo[1,5-a]pyrimidine | 121 | 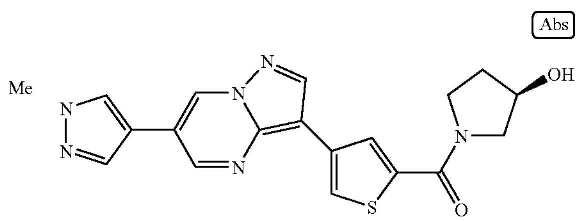 [SMILES: "Me" ; O=C(c1cc(-c2cnn3cc(-c4cn[nH]c4)cnc23)cs1)N1CC[C@@H](O)C1] | 409 |
| N-[2-hydroxy-2-methyl-1-(trifluoromethyl)propyl]-4-[6-(1-methyl-1H-pyrazol-4-yl)pyrazolo[1,5-a]pyrimidin-3-yl]thiophene-2-carboxamide | 122 | 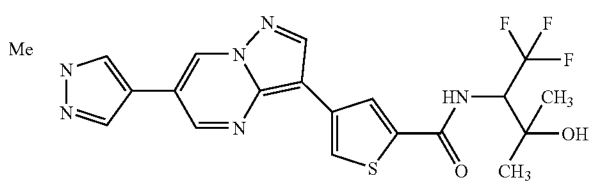 | 465 |
| N-methyl-4-[6-(1-methyl-1H-pyrazol-4-yl)pyrazolo[1,5-a]pyrimidin-3-yl]-N-(2,2,2-trifluoroethyl)thiophene-2-carboxamide | 123 | 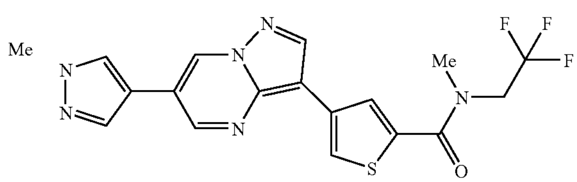 [SMILES: "Me" ; CN(CC(F)(F)F)C(=O)c1cc(-c2cnn3cc(-c4cn[nH]c4)cnc23)cs1] | 421 |
| N-[2-(dimethylamino)ethyl]-4-[6-(1-methyl-1H-pyrazol-4-yl)pyrazolo[1,5-a]pyrimidin-3-yl]-N-(2,2,2-trifluoroethyl)thiophene-2-carboxamide | 124 | 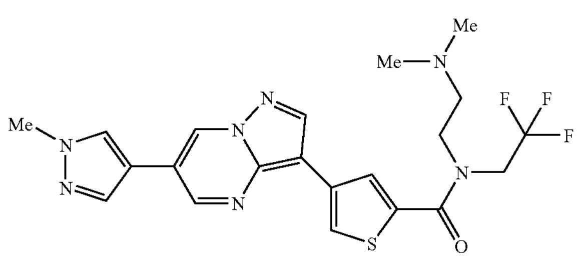 [SMILES: CN(C)CCN(CC(F)(F)F)C(=O)c1cc(-c2cnn3cc(-c4cnn(C)c4)cnc23)cs1] | 478 |

-continued

| Name | Example | Structure | LCMS M + H = |
|---|---|---|---|
| 3-(5-{[3-(fluoromethyl)pyrrolidin-1-yl]carbonyl}-3-thienyl)-6-(1-methyl-1H-pyrazol-4-yl)pyrazolo[1,5-a]pyrimidine | 125 | 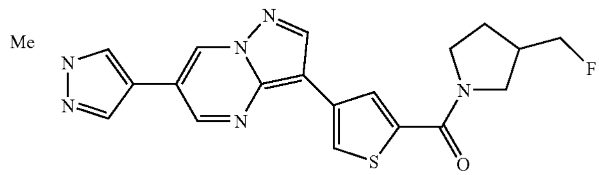 [SMILES: "Me" ; O=C(c1cc(-c2cnn3cc(-c4cn[nH]c4)cnc23)cs1)N1CCC(CF)C1] | 411 |
| 3-(5-{[(3S)-3-fluoropyrrolidin-1-yl]carbonyl}-3-thienyl)-6-(1H-pyrazol-4-yl)pyrazolo[1,5-a]pyrimidine | 126 | 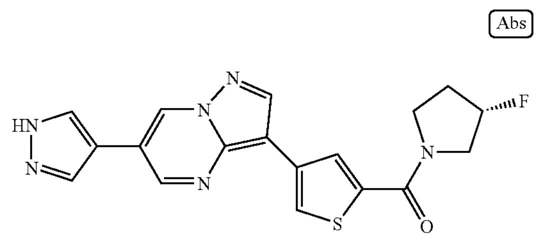 [SMILES: O=C(c1cc(-c2cnn3cc(-c4cn[nH]c4)cnc23)cs1)N1CC[C@H](F)C1] | 383 |
| 3-(5-{[(3R)-3-fluoropyrrolidin-1-yl]carbonyl}-3-thienyl)-6-(1-methyl-1H-pyrazol-4-yl)pyrazolo[1,5-a]pyrimidine | 127 | 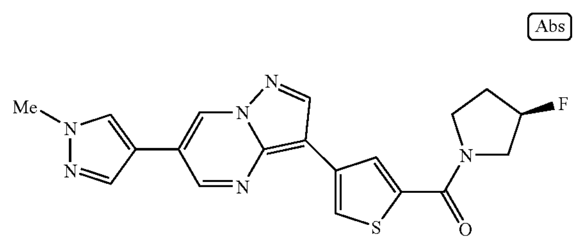 [SMILES: Cn1cc(-c2cnc3c(-c4csc(C(=O)N5CC[C@@H](F)C5)c4)cnn3c2)cn1] | 397 |
| N-(2-propoxyethyl)-4-(6-pyridin-3-ylpyrazolo[1,5-a]pyrimidin-3-yl)thiophene-2-carboxamide | 128 | 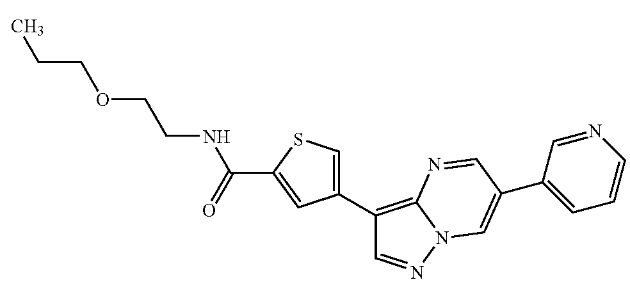 [SMILES: CCCOCCNC(=O)c1cc(-c2cnn3cc(-c4cccnc4)cnc23)cs1] | 408 |
| N-[(1S)-2-methoxy-1-methylethyl]-4-(6-pyridin-3-ylpyrazolo[1,5-a]pyrimidin-3-yl)thiophene-2-carboxamide | 129 | 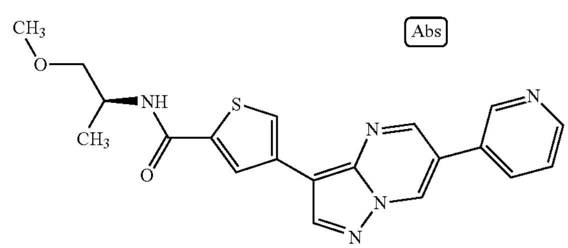 [SMILES: COC[C@H](C)NC(=O)c1cc(-c2cnn3cc(-c4cccnc4)cnc23)cs1] | 394 |
| 3-(5-{[(3S,4S)-3,4-difluoropyrrolidin-1-yl]carbonyl}-3-thienyl)-6-(1-methyl-1H-pyrazol-4-yl)pyrazolo[1,5-a]pyrimidine | 130 | 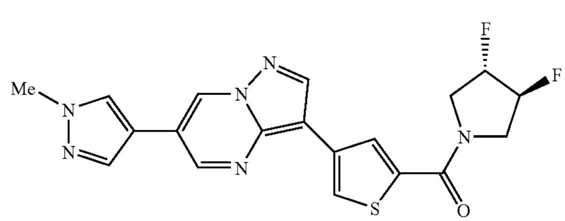 [SMILES: Cn1cc(-c2cnc3c(-c4csc(C(=O)N5C[C@H](F)[C@@H](F)C5)c4)cnn3c2)cn1] | 415 |

| Name | Example | Structure | LCMS M + H = |
|---|---|---|---|
| [3-({4-[6-(1-methyl-1H-pyrazol-4-yl)pyrazolo[1,5-a]pyrimidin-3-yl]-2-thienyl}carbonyl)-3-azabicyclo[3.1.0]hex-6-yl]methanol | 131 | | 421 |
| 4-[6-(1-methyl-1H-pyrazol-4-yl)pyrazolo[1,5-a]pyrimidin-3-yl]-N-(tetrahydro-3-thienyl)thiophene-2-carboxamide | 132 | 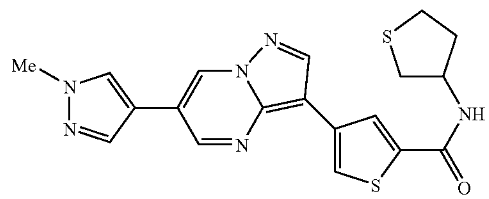 [SMILES: Cn1cc(-c2cnc3c(-c4csc(C(=O)NC5CCSC5)c4)cnn3c2)cn1] | 411 |
| 4-[6-(1-methyl-1H-pyrazol-4-yl)pyrazolo[1,5-a]pyrimidin-3-yl]-N-[(1-morpholin-4-ylcycloheptyl)methyl]thiophene-2-carboxamide | 133 | 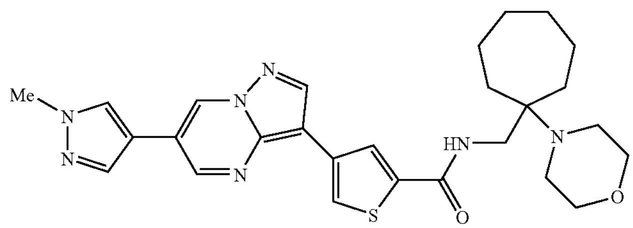 [SMILES: Cn1cc(-c2cnc3c(-c4csc(C(=O)NCC5(N6CCOCC6)CCCCCC5)c4)cnn3c2)cn1] | 520 |
| 4-[6-(1-methyl-1H-pyrazol-4-yl)pyrazolo[1,5-a]pyrimidin-3-yl]-N-(3-thienylmethyl)thiophene-2-carboxamide | 134 | 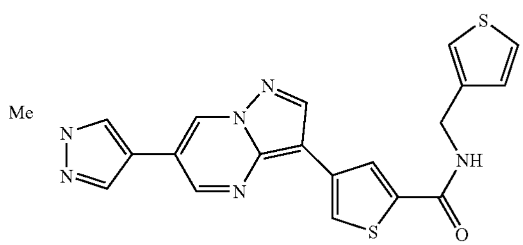 [SMILES: "Me" ; O=C(NCc1ccsc1)c1cc(-c2cnn3cc(-c4cn[nH]c4)cnc23)cs1] | 421 |
| N-(trans-4-hydroxycyclohexyl)-4-[6-(1-methyl-1H-pyrazol-4-yl)pyrazolo[1,5-a]pyrimidin-3-yl]thiophene-2-carboxamide | 135 | 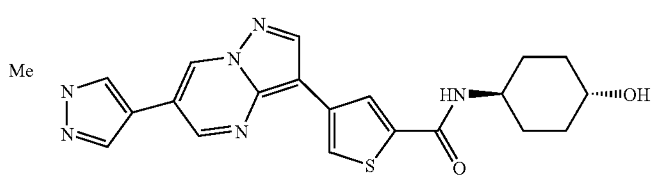 [SMILES: "Me" ; O=C(N[C@H]1CC[C@H](O)CC1)c1cc(-c2cnn3cc(-c4cn[nH]c4)cnc23)cs1] | 423 |
| 4-[6-(1-methyl-1H-pyrazol-4-yl)pyrazolo[1,5-a]pyrimidin-3-yl]-N-(octahydrocyclopenta[c]pyrrol-4-yl)thiophene-2-carboxamide | 136 | 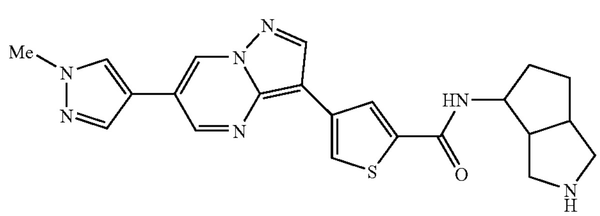 [SMILES: Cn1cc(-c2cnc3c(-c4csc(C(=O)NC5CCC6CNCC65)c4)cnn3c2)cn1] | 434 |
| 4-[6-(1-methyl-1H-pyrazol-4-yl)pyrazolo[1,5-a]pyrimidin-3-yl]-N-[(3aR,6aR)-octahydrocyclopenta[b]pyrrol-4-yl]thiophene-2-carboxamide | 137 | 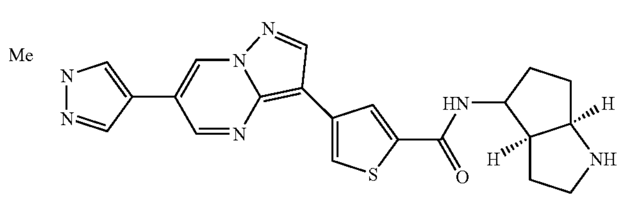 [SMILES: "Me" ; O=C(NC1CC[C@H]2NCC[C@@H]12)c1cc(-c2cnn3cc(-c4cn[nH]c4)cnc23)cs1] | 434 |

| Name | Example | Structure | LCMS M + H = |
|---|---|---|---|
| 4-[6-(5,6-dihydro-4H-pyrrolo[1,2-b]pyrazol-3-yl)pyrazolo[1,5-a]pyrimidin-3-yl]-N-(2,2,2-trifluoroethyl)thiophene-2-carboxamide | 138 | 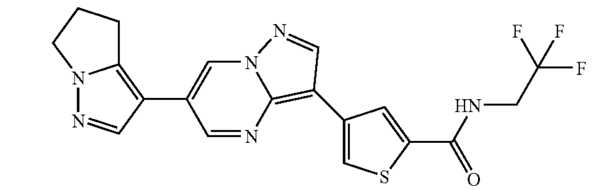 [SMILES: O=C(NCC(F)(F)F)c1cc(-c2cnn3cc(-c4cnn5c4CCC5)cnc23)cs1] | 433 |
| N-(1-methylazetidin-3-yl)-4-[6-(1-methyl-1H-pyrazol-4-yl)pyrazolo[1,5-a]pyrimidin-3-yl]thiophene-2-carboxamide | 139 | 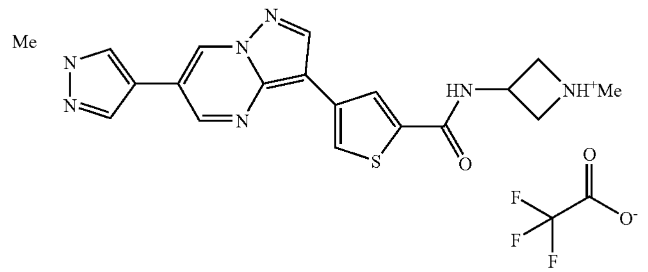 | 394 |
| N-[(1S)-2-hydroxy-2-methyl-1-(trifluoromethyl)propyl]-4-[6-(1-methyl-1H-pyrazol-4-yl)pyrazolo[1,5-a]pyrimidin-3-yl]thiophene-2-carboxamide | 140 | 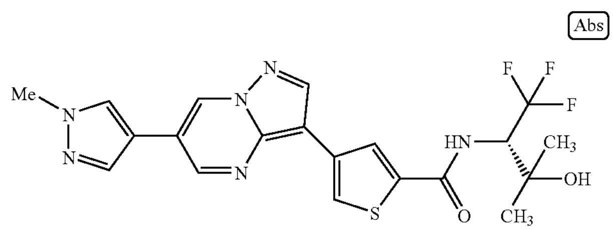 [SMILES: Cn1cc(-c2cnc3c(-c4csc(C(=O)N[C@@H](C(C)(C)O)C(F)(F)F)c4)cnn3c2)cn1] | 465 |
| N-[(1R)-2-hydroxy-2-methyl-1-(trifluoromethyl)propyl]-4-[6-(1-methyl-1H-pyrazol-4-yl)pyrazolo[1,5-a]pyrimidin-3-yl]thiophene-2-carboxamide | 141 | 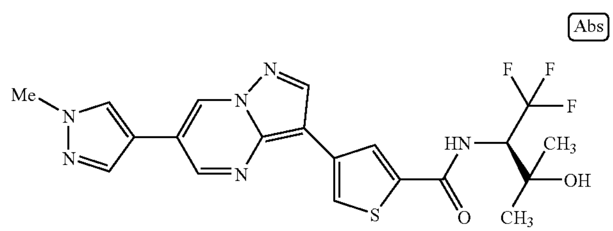 [SMILES: Cn1cc(-c2cnc3c(-c4csc(C(=O)N[C@H](C(C)(C)O)C(F)(F)F)c4)cnn3c2)cn1] | 465 |
| 3-{5-[(4-fluoropiperidin-1-yl)carbonyl]-3-thienyl}-6-(1-methyl-1H-pyrazol-4-yl)pyrazolo[1,5-a]pyrimidine | 142 | 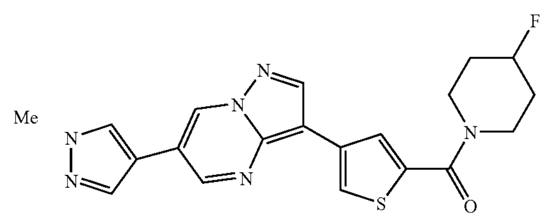 [SMILES: "Me" ; O=C(c1cc(-c2cnn3cc(-c4cn[nH]c4)cnc23)cs1)N1CCC(F)CC1] | 411 |
| 3-{5-[(4,4-difluoropiperidin-1-yl)carbonyl]-3-thienyl}-6-(1-methyl-1H-pyrazol-4-yl)pyrazolo[1,5-a]pyrimidine | 143 | 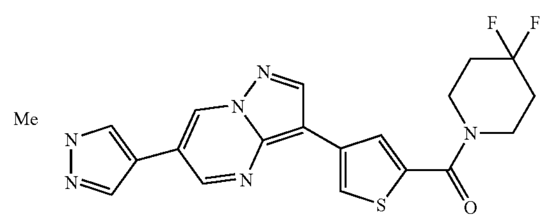 [SMILES: "Me" ; O=C(c1cc(-c2cnn3cc(-c4cn[nH]c4)cnc23)cs1)N1CCC(F)(F)CC1] | 429 |
| 3-{5-[(3-fluoropiperidin-1-yl)carbonyl]-3-thienyl}-6-(1-methyl-1H-pyrazol-4-yl)pyrazolo[1,5-a]pyrimidine | 144 | 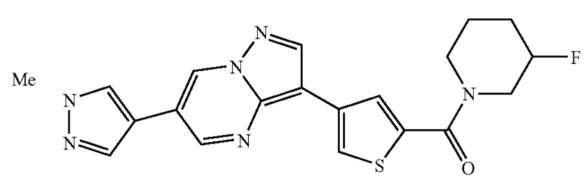 [SMILES: "Me" ; O=C(c1cc(-c2cnn3cc(-c4cn[nH]c4)cnc23)cs1)N1CCCC(F)C1] | 411 |

-continued

| Name | Example | Structure | LCMS M + H = |
|---|---|---|---|
| N-(2,3-dihydroxypropyl)-4-[6-(1-methyl-1H-pyrazol-4-yl)pyrazolo[1,5-a]pyrimidin-3-yl]thiophene-2-carboxamide | 145 | 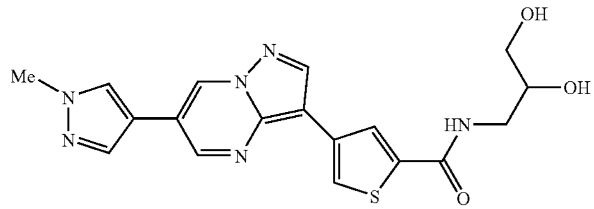 [SMILES: Cn1cc(-c2cnc3c(-c4csc(C(=O)NCC(O)CO)c4)cnn3c2)cn1] | 399 |
| N-(cis-4-hydroxycyclohexyl)-4-[6-(1-methyl-1H-pyrazol-4-yl)pyrazolo[1,5-a]pyrimidin-3-yl]thiophene-2-carboxamide | 146 | 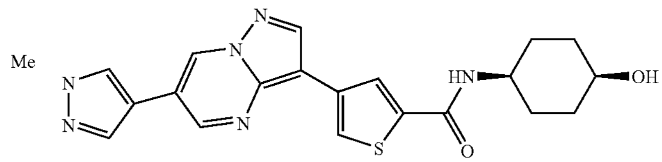 [SMILES: "Me" ; O=C(N[C@H]1CC[C@@H](O)CC1)c1cc(-c2cnn3cc(-c4cn[nH]c4)cnc23)cs1] | 423 |
| N-{[1-(dimethylamino)cyclohexyl]methyl}-4-[6-(1-methyl-1H-pyrazol-4-yl)pyrazolo[1,5-a]pyrimidin-3-yl]thiophene-2-carboxamide | 147 | 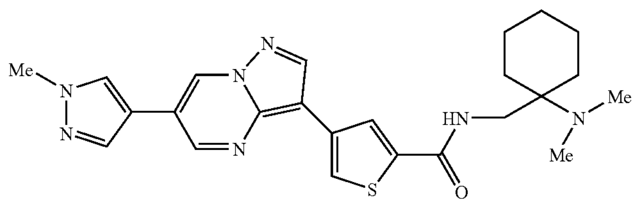 [SMILES: CN(C)C1(CNC(=O)c2cc(-c3cnn4cc(-c5cnn(C)c5)cnc34)cs2)CCCCC1] | 464 |
| 4-{6-[1-(3-morpholin-4-ylpropyl)-1H-pyrazol-4-yl]pyrazolo[1,5-a]pyrimidin-3-yl}-N-(2,2,2-trifluoroethyl)thiophene-2-carboxamide | 148 | 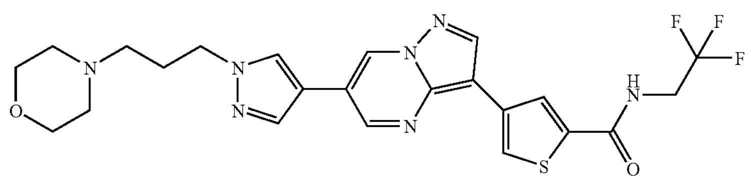 [SMILES: O=C(NCC(F)(F)F)c1cc(-c2cnn3cc(-c4cnn(CCCN5CCOCC5)c4)cnc23)cs1] | 520 |
| N-[(1R,2S)-2-hydroxycyclohexyl]-4-[6-(1-methyl-1H-pyrazol-4-yl)pyrazolo[1,5-a]pyrimidin-3-yl]thiophene-2-carboxamide | 149 | 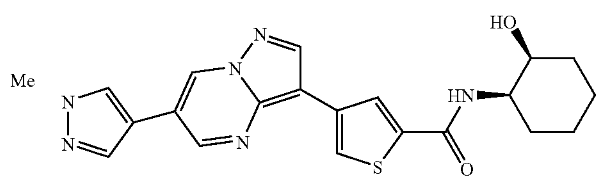 [SMILES: "Me" ; O=C(N[C@@H]1CCCC[C@@H]1O)c1cc(-c2cnn3cc(-c4cn[nH]c4)cnc23)cs1] | 423 |
| N-[(1R,2R)-2-hydroxycyclohexyl]-4-[6-(1-methyl-1H-pyrazol-4-yl)pyrazolo[1,5-a]pyrimidin-3-yl]thiophene-2-carboxamide | 150 | 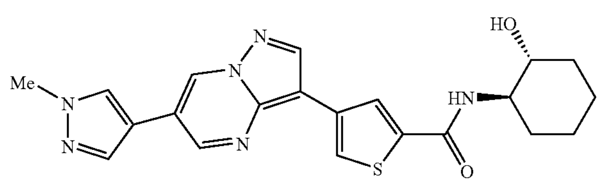 [SMILES: Cn1cc(-c2cnc3c(-c4csc(C(=O)N[C@@H]5CCCC[C@H]5O)c4)cnn3c2)cn1] | 423 |
| 4-(6-pyridin-3-ylpyrazolo[1,5-a]pyrimidin-3-yl)-N-(1,3-thiazol-2-ylmethyl)thiophene-2-carboxamide | 151 | 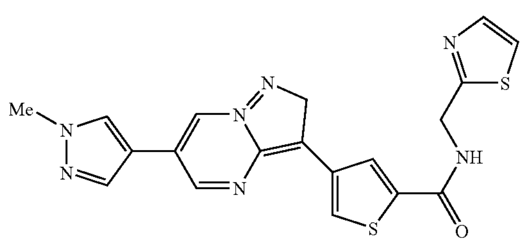 | 419 |

-continued

| Name | Example | Structure | LCMS M + H = |
|---|---|---|---|
| 4-[6-(1-methyl-1H-pyrazol-4-yl)pyrazolo[1,5-a]pyrirnidin-3-yl]-N-[(1-morpholin-4-ylcyclohexyl)methyl]thiophene-2-carboxamide | 152 | 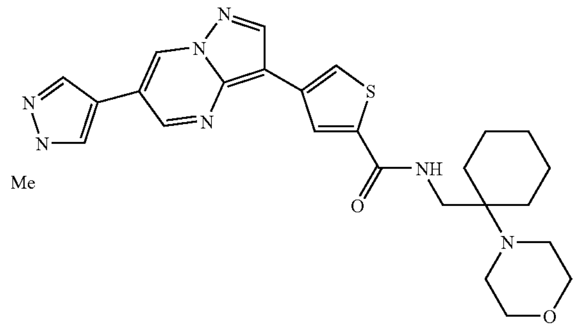 [SMILES: "Me" ; O=C(NCC1(N2CCOCC2)CCCCC1)c1cc(-c2cnn3cc(-c4cn[nH]c4)cnc23)cs1] | 506 |
| N-[(1S,2S)-2-aminocyclohexyl]-4-[6-(1-methyl-1H-pyrazol-4-yl)pyrazolo[1,5-a]pyrimidin-3-yl]thiophene-2-carboxamide | 153 | 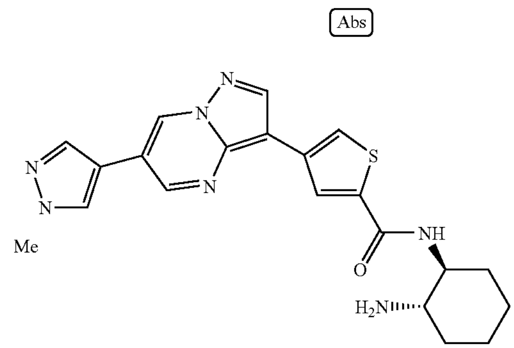 [SMILES: "Me" ; N[C@H]1CCCC[C@@H]1NC(=O)c1cc(-c2cnn3cc(-c4cn[nH]c4)cnc23)cs1] | 422 |
| 4-[6-(1-methyl-1H-pyrazol-4-yl)pyrazolo[1,5-a]pyrimidin-3-yl]-N-(4-methyl-1,3-thiazol-2-yl)thiophene-2-carboxamide | 154 | 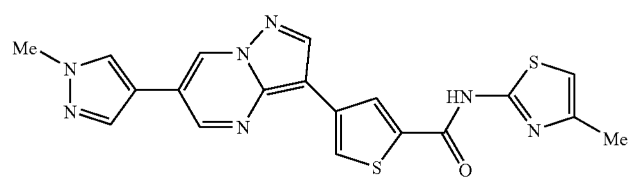 [SMILES: Cc1csc(NC(=O)c2cc(-c3cnn4cc(-c5cnn(C)c5)cnc34)cs2)n1] | 422 |
| N-(1,1-dioxidotetrahydro-3-thienyl)-4-[6-(1-methyl-1H-pyrazol-4-yl)pyrazolo[1,5-a]pyrimidin-3-yl]thiophene-2-carboxamide | 155 | 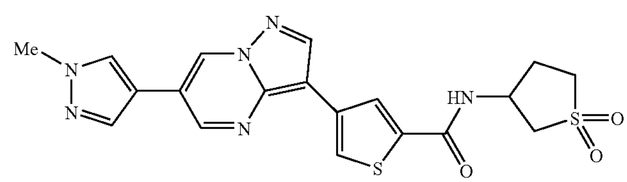 [SMILES: Cn1cc(-c2cnc3c(-c4csc(C(=O)NC5CCS(=O)(=O)C5)c4)cnn3c2)cn1] | |
| N-methyl-1-({4-[6-(1-methyl-1H-pyrazol-4-yl)pyrazolo[1,5-a]pyrimidin-3-yl]-2-thienyl}carbonyl)pyrrolidin-3-amine | 156 | 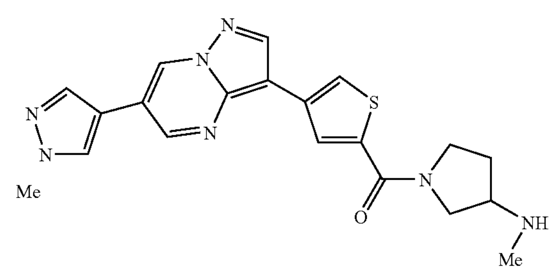 [SMILES: "Me" ; CNC1CCN(C(=O)c2cc(-c3cnn4cc(-c5cn[nH]c5)cnc34)cs2)C1] | 408 |
| 3-(5-{[2-(methoxymethyl)pyrrolidin-1-yl]carbonyl}-3-thienyl)-6-(1-methyl-1H-pyrazol-4-yl)pyrazolo[1,5-a]pyrimidine | 157 | 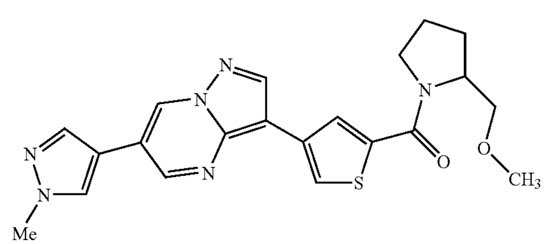 [SMILES: COCC1CCCN1C(=O)c1cc(-c2cnn3cc(-c4cnn(C)c4)cnc23)cs1] | 423 |

-continued

| Name | Example | Structure | LCMS M + H = |
|---|---|---|---|
| 4-[6-(1-methyl-1H-pyrazol-4-yl)pyrazolo[1,5-a]pyrimidin-3-yl]-N-[(1-piperidin-1-ylcyclopentyl)methyl]thiophene-2-carboxamide | 158 | 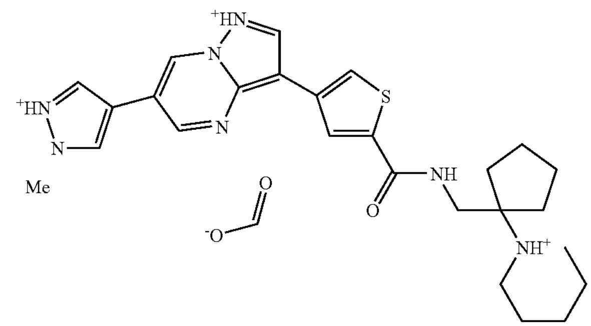 | 490 |
| N-[(1S,2S)-2-hydroxycyclopentyl]-4-[6-(1-methyl-1H-pyrazol-4-yl)pyrazolo[1,5-a]pyrimidin-3-yl]thiophene-2-carboxamide | 159 | 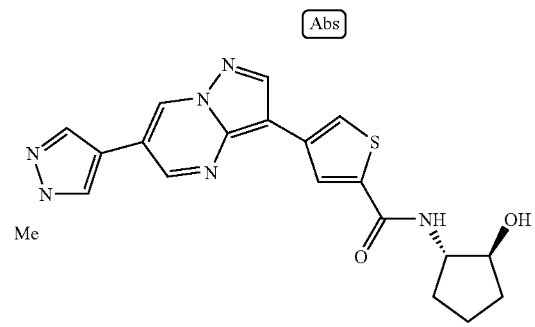 [SMILES: "Me" ; O=C(N[C@H]1CCC[C@@H]1O)c1cc(-c2cnn3cc(-c4cn[nH]c4)cnc23)cs1] | 409 |
| 4-[6-(1-methyl-1H-pyrazol-4-yl)pyrazolo[1,5-a]pyrimidin-3-yl]-N-[(1-piperidin-1-ylcyclohexyl)methyl]thiophene-2-carboxamide | 160 | 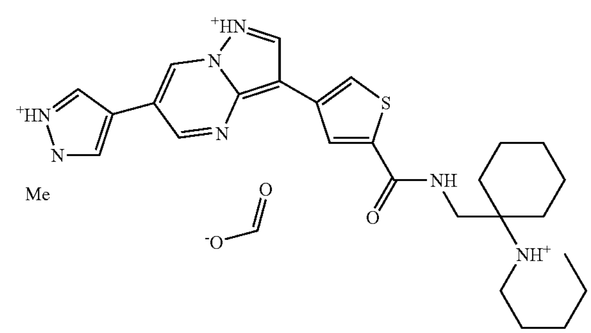 | 504 |
| 4-[6-(1-methyl-1H-pyrazol-4-yl)pyrazolo[1,5-a]pyrimidin-3-yl]-N-(octahydrocyclopenta[c]pyrrol-5-yl)thiophene-2-carboxamide | 161 | 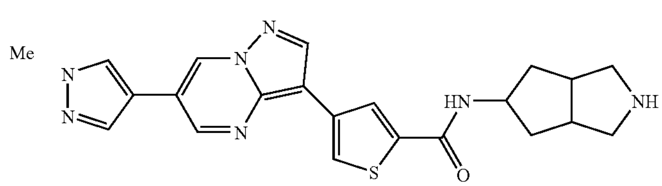 [SMILES: "Me" ; O=C(NC1CC2CNCC2C1)c1cc(-c2cnn3cc(-c4cn[nH]c4)cnc23)cs1] | 434 |
| 3-[5-(2,6-diazaspiro[3.3]hept-2-ylcarbonyl)-3-thienyl]-6-(1-methyl-1H-pyrazol-4-yl)pyrazolo[1,5-a]pyrimidine | 162 | 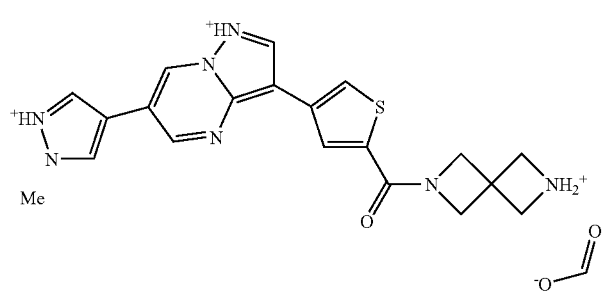 | 406 |

-continued

| Name | Example | Structure | LCMS M + H = |
|---|---|---|---|
| N-(1-methylpiperidin-3-yl)-4-[6-(1-methyl-1H-pyrazol-4-yl)pyrazolo[1,5-a]pyrimidin-3-yl]thiophene-2-carboxamide | 163 | 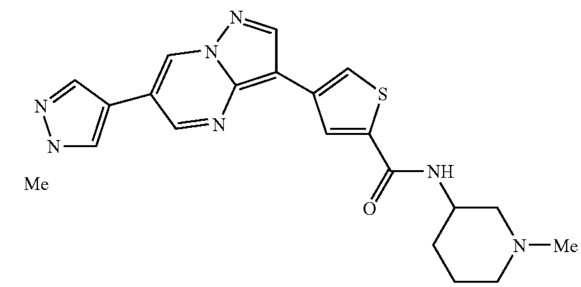 [SMILES: "Me" ; CN1CCCC(NC(=O)c2cc(-c3cnn4cc(-c5cn[nH]c5)cnc34)cs2)C1] | 422 |
| (3R)-N,N-dimethyl-1-({4-[6-(1-methyl-1H-pyrazol-4-yl)pyrazolo[1,5-a]pyrimidin-3-yl]-2-thienyl}carbonyl)pyrrolidin-3-amine | 164 | 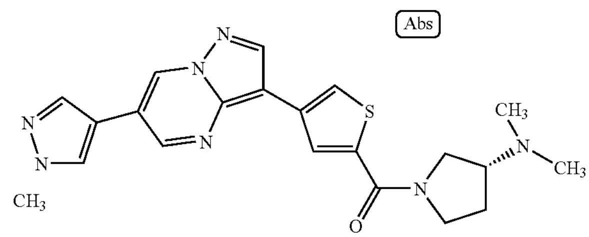 | 422 |
| N-(1,1-dioxidotetrahydro-3-thienyl)-N-methyl-4-[6-(1-methyl-1H-pyrazol-4-yl)pyrazolo[1,5-a]pyrimidin-3-yl]thiophene-2-carboxamide | 165 | 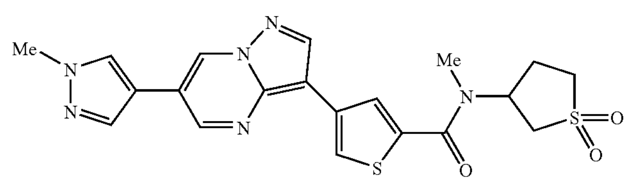 [SMILES: CN(C(=O)c1cc(-c2cnn3cc(-c4cnn(C)c4)cnc23)cs1)C1CCS(=O)(=O)C1] | 457 |
| 6-(1-methyl-1H-pyrazol-4-yl)-3-{5-[(1-methyl-2,4,6,6a-tetrahydropyrrolo[3,4-b]pyrrol-5(1H)-yl)carbonyl]-3-thienyl}pyrazolo[1,5-a]pyrimidine | 166 | 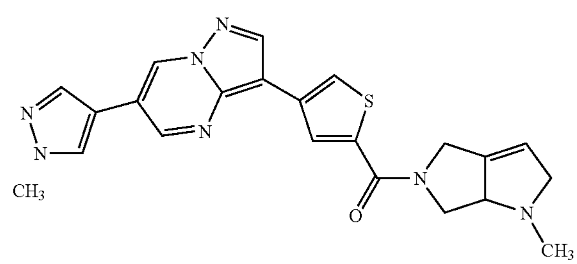 | 432 |
| 3-[5-(hexahydropyrrolo[3,4-b]pyrrol-5(1H)-ylcarbonyl)-thienyl]-6-(1-methyl-1H-pyrazol-4-yl)pyrazolo[1,5-a]pyrimidine | 167 | | 420 |
| N-{[(1R,2R)-2-hydroxy-2-methylcyclohexyl]methyl}-4-[6-(1-methyl-1H-pyrazol-4-yl)pyrazolo[1,5-a]pyrimidin-3-yl]thiophene-2-carboxamide | 168 | 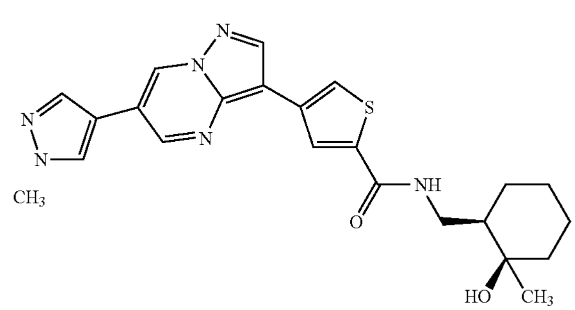 | 451 |

| Name | Example | Structure | LCMS M + H = |
|---|---|---|---|
| N-[(3S,4S)-4-hydroxy-1,1-dioxidotetrahydro-3-thienyl]-4-[6-(1-methyl-1H-pyrazol-4-yl)pyrazolo[1,5-a]pyrimidin-3-yl]thiophene-2-carboxamide | 169 | 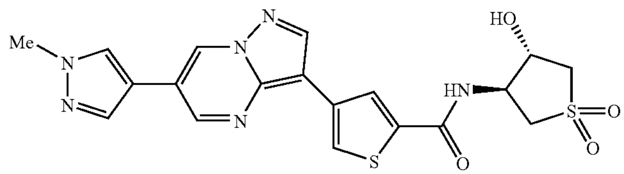 [SMILES: Cn1cc(-c2cnc3c(-c4csc(C(=O)N[C@@H]5CS(=O)(=O)C[C@H]5O)c4)cnn3c2)cn1] | 459 |
| N-[(1-hydroxycyclohexyl)methyl]-4-[6-(1-methyl-1H-pyrazol-4-yl)pyrazolo[1,5-a]pyrimidin-3-yl]thiophene-2-carboxamide | 170 | 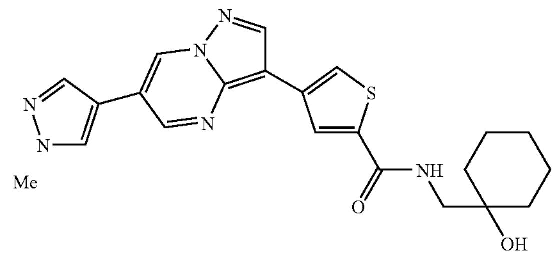 [SMILES: "Me" ; O=C(NCC1(O)CCCCC1)c1cc(-c2cnn3cc(-c4cn[nH]c4)cnc23)cs1] | 437 |
| [(2S)-1-({4-[6-(1-methyl-1H-pyrazol-4-yl)pyrazolo[1,5-a]pyrimidin-3-yl]-2-thienyl}carbonyl)pyrrolidin-2-yl]methanol | 171 | 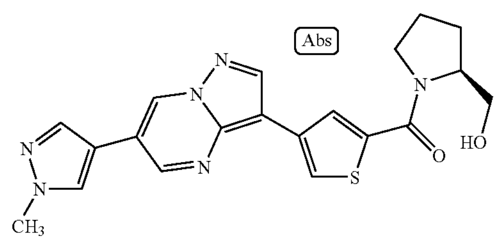 [SMILES: Cn1cc(-c2cnc3c(-c4csc(C(=O)N5CCC[C@H]5CO)c4)cnn3c2)cn1] | 409 |
| N-[(1R,2S)-2-hydroxycyclopentyl]-4-[6-(1-methyl-1H-pyrazol-4-yl)pyrazolo[1,5-a]pyrimidin-3-yl]thiophene-2-carboxamide | 172 | 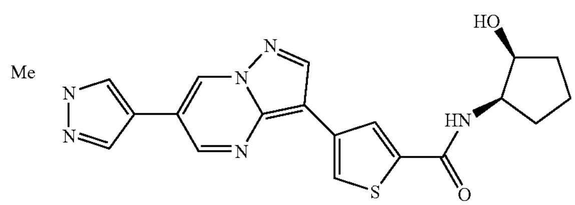 [SMILES: "Me" ; O=C(N[C@@H]1CCC[C@@H]1O)c1cc(-c2cnn3cc(-c4cn[nH]c4)cnc23)cs1] | 409 |
| 1-({4-[6-(1-methyl-1H-pyrazol-4-yl)pyrazolo[1,5-a]pyrimidin-3-yl]-2-thienyl}carbonyl)azetidin-3-amine | 173 | 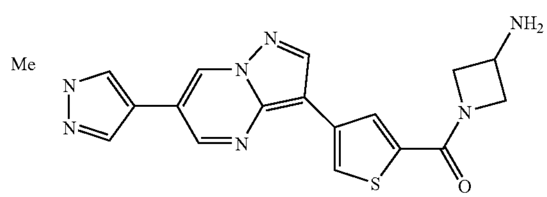 [SMILES: "Me" ; NC1CN(C(=O)c2cc(-c3cnn4cc(-c5cn[nH]c5)cnc34)cs2)C1] | 380 |
| 4-[6-(1-methyl-1H-pyrazol-4-yl)pyrazolo[1,5-a]pyrimidin-3-yl]-N-{(1S,2S)-2-[(methylsulfonyl)amino]cyclohexyl}thiophene-2-carboxamide | 174 | 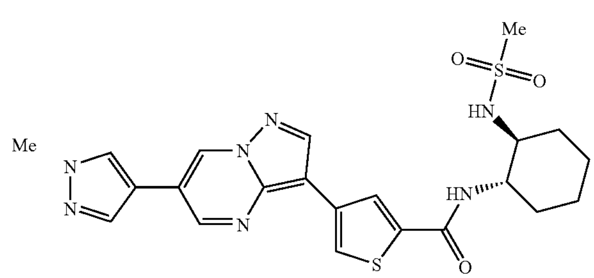 [SMILES: "Me" ; CS(=O)(=O)N[C@H]1CCCC[C@@H]1NC(=O)c1cc(-c2cnn3cc(-c4cn[nH]c4)cnc23)cs1] | 500 |
| N-[(1S,2S)-2-aminocyclohexyl]-4-[6-(1-methyl-1H-pyrazol-4-yl)pyrazolo[1,5-a]pyrimidin-3-yl]thiophene-2-carboxamide | 175 | 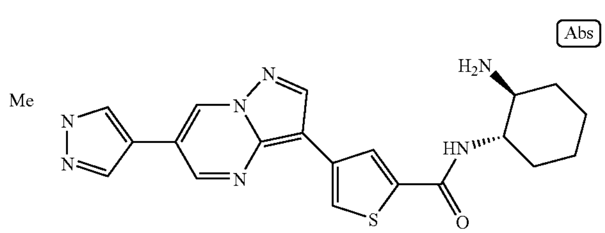 [SMILES: "Me" ; N[C@H]1CCCC[C@@H]1NC(=O)c1cc(-c2cnn3cc(-c4cn[nH]c4)cnc23)cs1] | 422 |

| Name | Example | Structure | LCMS M + H = |
|---|---|---|---|
| N-methyl-N-[(2R)-2-(methylamino)cyclohexyl]-4-[6-(1-methyl-1H-pyrazol-4-yl)pyrazolo[1,5-a]pyrimidin-3-yl]thiophene-2-carboxamide | 176 | 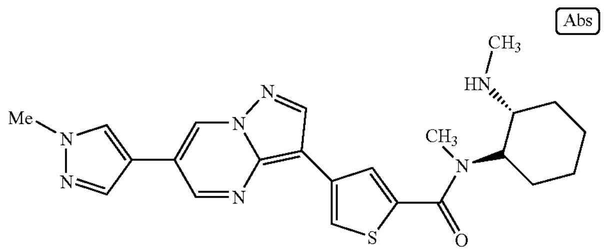 | 450 |
| N-[(1R,2S)-2-aminocyclohexyl]-4-[6-(1-methyl-1H-pyrazol-4-yl)pyrazolo[1,5-a]pyrimidin-3-yl]thiophene-2-carboxamide | 177 | 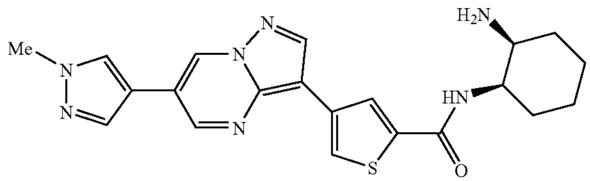 [SMILES: Cn1cc(-c2cnc3c(-c4csc(C(=O)N[C@@H]5CCCC[C@@H]5N)c4)cnn3c2)cn1] | 422 |
| N-[(1R,2R)-2-aminocyclohexyl]-4-[6-(1-methyl-1H-pyrazol-4-yl)pyrazolo[1,5-a]pyrimidin-3-yl]thiophene-2-carboxamide | 178 | 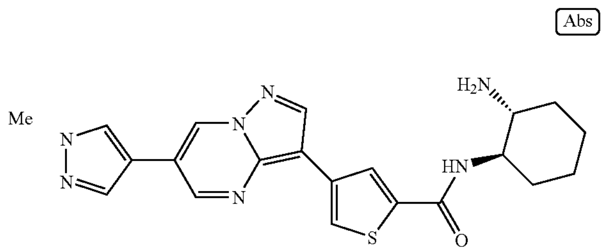 [SMILES: "Me" ; N[C@@H]1CCCC[C@H]1NC(=O)c1cc(-c2cnn3cc(-c4cn[nH]c4)cnc23)cs1] | 422 |
| N-[2-(2-furyl)ethyl]-4-(6-pyridin-3-ylpyrazolo[1,5-a]pyrimidin-3-yl)thiophene-2-carboxamide | 179 | 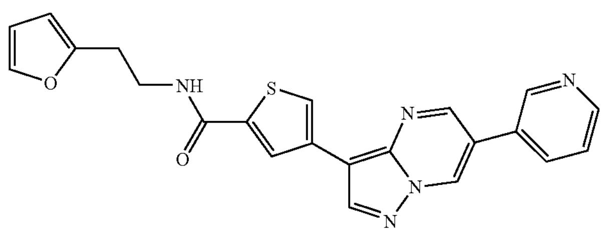 [SMILES: O=C(NCCc1ccco1)c1cc(-c2cnn3cc(-c4cccnc4)cnc23)cs1] | 416 |
| 4-(6-pyridin-3-ylpyrazolo[1,5-a]pyrimidin-3-yl)-N-[(2S)-tetrahydrofuran-2-ylmethyl]thiophene-2-carboxamide | 180 | 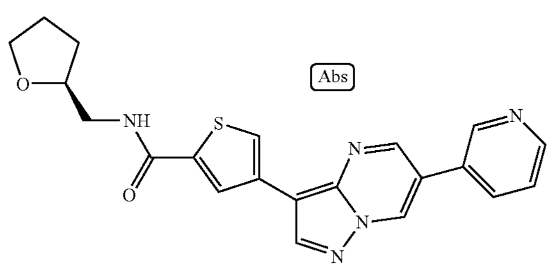 [SMILES: O=C(NC[C@@H]1CCCO1)c1cc(-c2cnn3cc(-c4cccnc4)cnc23)cs1] | 406 |
| 4-(6-pyridin-3-ylpyrazolo[1,5-a]pyrimidin-3-yl)-N-(3-thienylmethyl)thiophene-2-carboxamide | 181 | 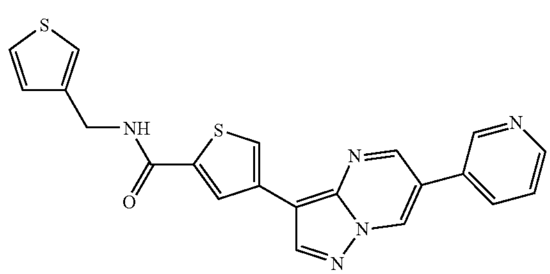 [SMILES: O=C(NCc1ccsc1)c1cc(-c2cnn3cc(-c4cccnc4)cnc23)cs1] | 418 |

-continued

| Name | Example | Structure | LCMS M + H = |
|---|---|---|---|
| N-(2,5-difluorobenzyl)-4-(6-pyridin-3-ylpyrazolo[1,5-a]pyrimidin-3-yl)thiophene-2-carboxamide | 182 | 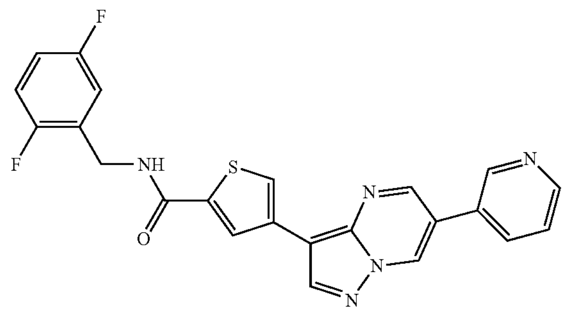 [SMILES: O=C(NCc1cc(F)ccc1F)c1cc(-c2cnn3cc(-c4cccnc4)cnc23)cs1] | 448 |
| N-(1-ethylpropyl)-4-(6-pyridin-3-ylpyrazolo[1,5-a]pyrimidin-3-yl)thiophene-2-carboxamide | 183 | 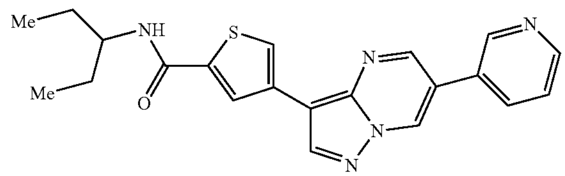 [SMILES: CCC(CC)NC(=O)c1cc(-c2cnn3cc(-c4cccnc4)cnc23)cs1] | 392 |
| 4-(6-pyridin-3-ylpyrazolo[1,5-a]pyrimidin-3-yl)-N-(1,3-thiazol-2-ylmethyl)thiophene-2-carboxamide | 184 | 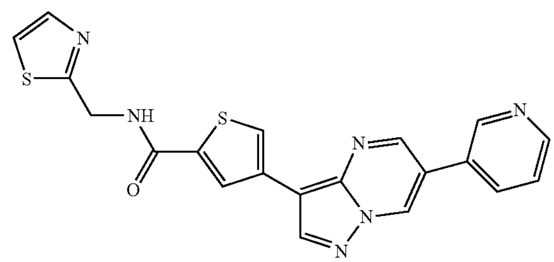 [SMILES: O=C(NCc1nccs1)c1cc(-c2cnn3cc(-c4cccnc4)cnc23)cs1] | 419 |
| N-[(1R,2S)-2-aminocyclohexyl]-4-[6-(5,6-dihydro-4H-pyrrolo[1,2-b]pyrazol-3-yl)pyrazolo[1,5-a]pyrimidin-3-yl]thiophene-2-carboxamide | 185 | 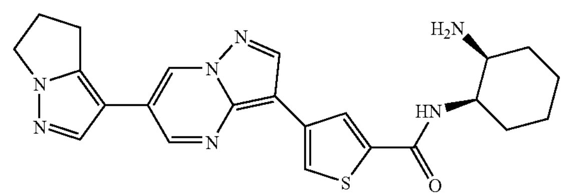 [SMILES: N[C@H]1CCCC[C@H]1NC(=O)c1cc(-c2cnn3cc(-c4cnn5c4CCC5)cnc23)cs1] | 448 |
| N-[(1,1-dioxidotetrahydro-3-thienyl)methyl]-4-[6-(1-methyl-1H-pyrazol-4-yl)pyrazolo[1,5-a]pyrimidin-3-yl]thiophene-2-carboxamide | 186 | 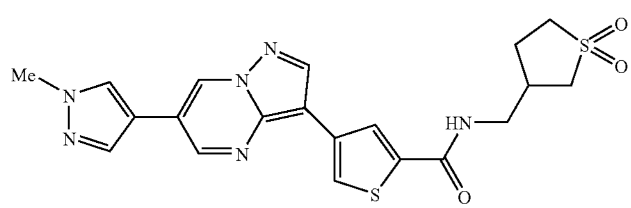 [SMILES: Cn1cc(-c2cnc3c(-c4csc(C(=O)NCC5CCS(=O)(=O)C5)c4)cnn3c2)cn1] | 457 |
| N-(3-aminopyridin-2-yl)-4-[6-(1-methyl-1H-pyrazol-4-yl)pyrazolo[1,5-a]pyrimidin-3-yl]thiophene-2-carboxamide | 187 | 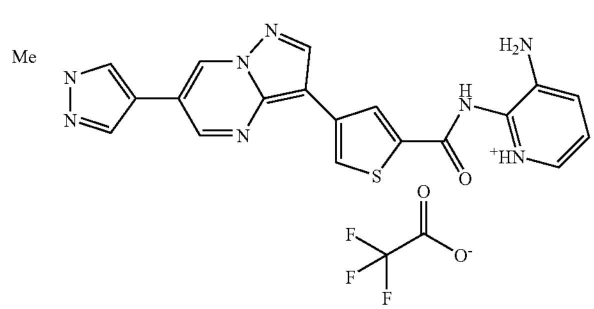 [SMILES: "Me" ; Nc1ccc[nH+]c1NC(=O)c1cc(-c2cnn3cc(-c4cn[nH]c4)cnc23)cs1 ; O=C([O-])C(F)(F)F] | 417 |

-continued

| Name | Example | Structure | LCMS M + H = |
|---|---|---|---|
| N-(4-amino-1-phenyl-1H-pyrazol-3-yl)-4-[6-(1-methyl-1H-pyrazol-4-yl)pyrazolo[1,5-a]pyrimidin-3-yl]thiophene-2-carboxamide | 188 | 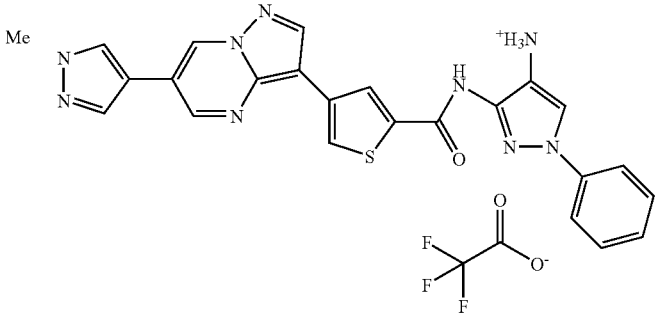 [SMILES: "Me" ; [NH3+]c1cn(-c2ccccc2)nc1NC(=O)c1cc(-c2cnn3cc(-c4cn[nH]c4)cnc23)cs1 ; O=C([O-])C(F)(F)F] | 482 |
| N-[(1R,2S)-2-aminocyclohexyl]-4-[6-(1-methyl-1H-pyrazol-4-yl)pyrazolo[1,5-a]pyrimidin-3-yl]thiophene-2-carboxamide | 189 | 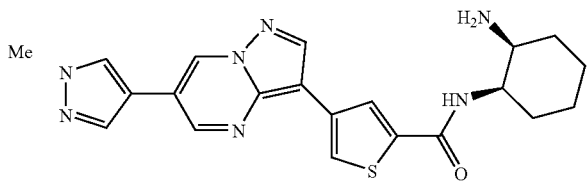 | 422 |
| N-[(1S,2R)-2-aminocyclohexyl]-4-[6-(1-methyl-1H-pyrazol-4-yl)pyrazolo[1,5-a]pyrimidin-3-yl]thiophene-2-carboxamide | 190 | 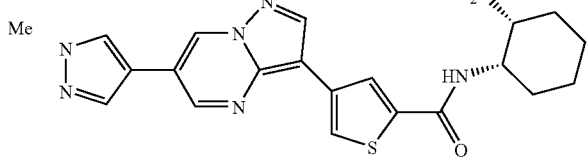 | 422 |
| N-[(3R,4R)-4-amino-1,1-dioxidotetrahydro-2H-thiopyran-3-yl]-4-[6-(1-methyl-1H-pyrazol-4-yl)pyrazolo[1,5-a]pyrimidin-3-yl]thiophene-2-carboxamide | 191 | 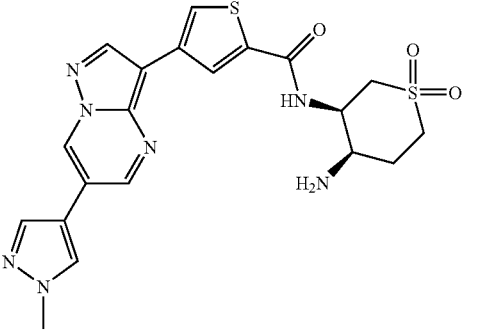 [SMILES: Cn1cc(-c2cnc3c(-c4csc(C(=O)N[C@H]5CS(=O)(=O)CC[C@H]5N)c4)cnn3c2)cn1] | 472 |
| N-[(3S,4S)-3-amino-1,1-dioxidotetrahydro-2H-thiopyran-4-yl]-4-[6-(1-methyl-1H-pyrazol-4-yl)pyrazolo[1,5-a]pyrimidin-3-yl]thiophene-2-carboxamide | 192 | 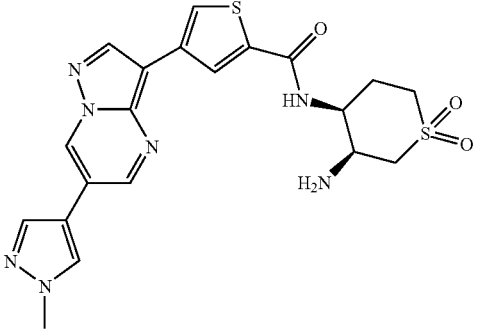 [SMILES: Cn1cc(-c2cnc3c(-c4csc(C(=O)N[C@H]5CCS(=O)(=O)C[C@H]5N)c4)cnn3c2)cn1] | 472 |

-continued

| Name | Example | Structure | LCMS M + H = |
|---|---|---|---|
| N-[(3R,4S)-4-amino-1,1-dioxidotetrahydro-2H-thiopyran-3-yl]-4-[6-(1-methyl-1H-pyrazol-4-yl)pyrazolo[1,5-a]pyrimidin-3-yl]thiophene-2-carboxamide | 193 | 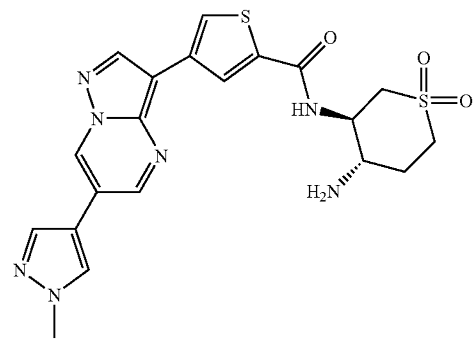 [SMILES: Cn1cc(-c2cnc3c(-c4csc(C(=O)N[C@H]5CS(=O)(=O)CC[C@@H]5N)c4)cnn3c2)cn1] | 472 |
| N-[(3R,4S)-3-amino-1,1-dioxidotetrahydro-2H-thiopyran-4-yl]-4-[6-(1-methyl-1H-pyrazol-4-yl)pyrazolo[1,5-a]pyrimidin-3-yl]thiophene-2-carboxamide | 194 | 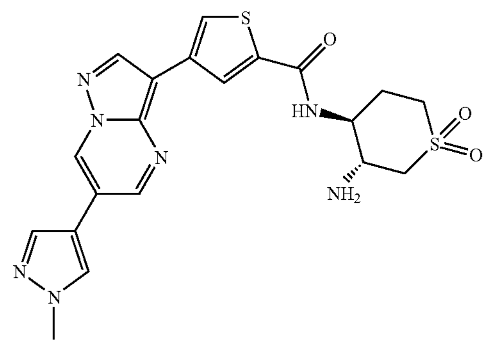 [SMILES: Cn1cc(-c2cnc3c(-c4csc(C(=O)N[C@H]5CCS(=O)(=O)C[C@@H]5N)c4)cnn3c2)cn1] | 472 |
| N-(1R,2R)-2-amino-3,3,3-trifluoro-1-phenylpropyl)-4-[6-(1-methyl-1H-pyrazol-4-yl)pyrazolo[1,5-a]pyrimidin-3-yl]thiophene-2-carboxamide | 195 | 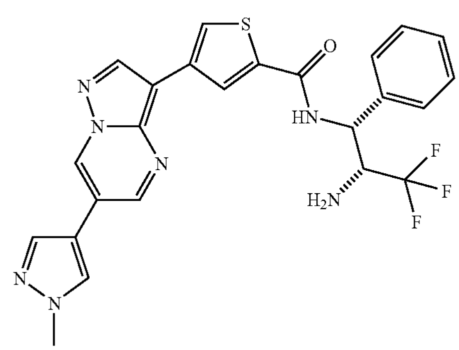 [SMILES: Cn1cc(-c2cnc3c(-c4csc(C(=O)N[C@H](c5ccccc5)[C@@H](N)C(F)(F)F)c4)cnn3c2)cn1] | 512 |
| N-(1S,2S)-2-amino-3,3,3-trifluoro-1-phenylpropyl)-4-[6-(1-methyl-1H-pyrazol-4-yl)pyrazolo[1,5-a]pyrimidin-3-yl]thiophene-2-carboxamide | 196 | 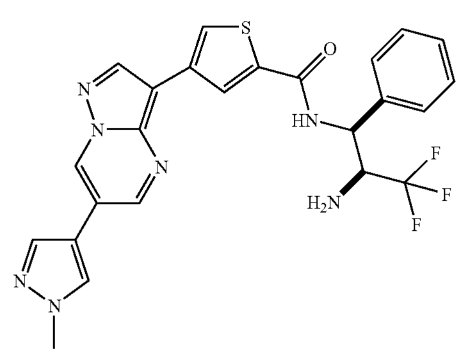 [SMILES: Cn1cc(-c2cnc3c(-c4csc(C(=O)N[C@@H](c5ccccc5)[C@H](N)C(F)(F)F)c4)cnn3c2)cn1] | 512 |

| Name | Example | Structure | LCMS M + H = |
|---|---|---|---|
| N-(1S,2R)-2-amino-3,3,3-trifluoro-1-phenylpropyl)-4-[6-(1-methyl-1H-pyrazol-4-yl)pyrazolo[1,5-a]pyrimidin-3-yl]thiophene-2-carboxamide | 197 | 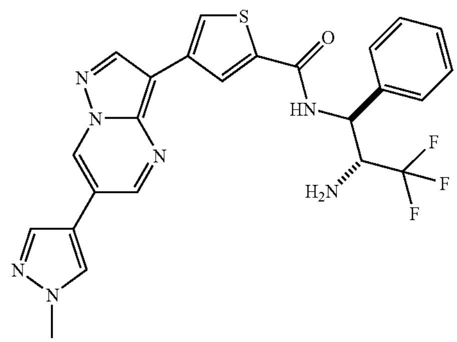 [SMILES: Cn1cc(-c2cnc3c(-c4csc(C(=O)N[C@@H](c5ccccc5)[C@@H](N)C(F)(F)F)c4)cnn3c2)cn1] | 512 |
| N-(1R,2S)-2-amino-3,3,3-trifluoro-1-phenylpropyl)-4-[6-(1-methyl-1H-pyrazol-4-yl)pyrazolo[1,5-a]pyrimidin-3-yl]thiophene-2-carboxamide | 198 | 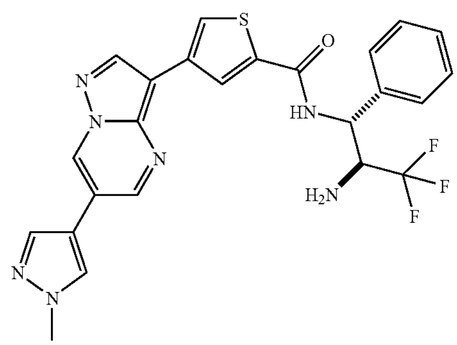 [SMILES: Cn1cc(-c2cnc3c(-c4csc(C(=O)N[C@H](c5ccccc5)[C@H](N)C(F)(F)F)c4)cnn3c2)cn1] | 512 |
| (3S)-1-({4-[6-(1-methyl-1H-pyrazol-4-yl)pyrazolo[1,5-a]pyrimidin-3-yl]-2-thienyl}carbonyl)piperidin-3-amine | 199 | 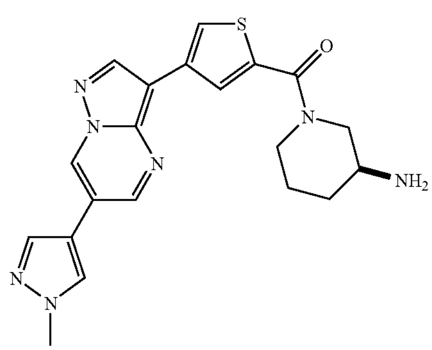 [SMILES: Cn1cc(-c2cnc3c(-c4csc(C(=O)N5CCC[C@H](N)C5)c4)cnn3c2)cn1] | 408 |
| (3R)-1-({4-[6-(1-methyl-1H-pyrazol-4-yl)pyrazolo[1,5-a]pyrimidin-3-yl]-2-thienyl}carbonyl)piperidin-3-amine | 200 | 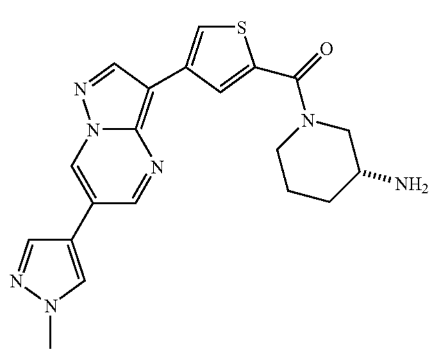 [SMILES: Cn1cc(-c2cnc3c(-c4csc(C(=O)N5CCC[C@@H](N)C5)c4)cnn3c2)cn1] | 408 |

-continued

| Name | Example | Structure | LCMS M + H = |
|---|---|---|---|
| N-[(1R,2S)-2-amino-3,3-difluorocyclohexyl]-4-[6-(1-methyl-1H-pyrazol-4-yl)pyrazolo[1,5-a]pyrimidin-3-yl]thiophene-2-carboxamide | 201 | 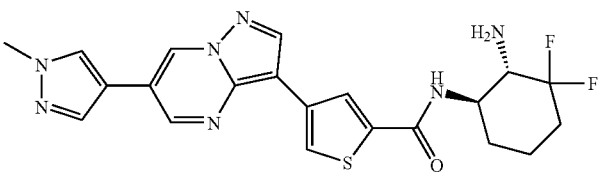 | 458.2 |
| N-[(1R,6R)-6-amino-2,2-difluorocyclohexyl]-5-methyl-4-[6-(1-methyl-1H-pyrazol-4-yl)pyrazolo[1,5-a]pyrimidin-3-yl]thiophene-2- | 202 | 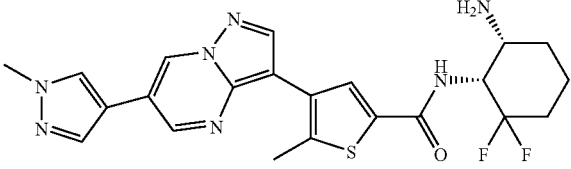 | 472.1 |
| N-[(1R,2R:1S,2S)-2-hydroxycyclohexyl]-4-[6-(1-methyl-1H-pyrazol-4-yl)pyrazolo[1,5-a]pyrimidin-3-yl]thiophene-2-carboxamide | 203 | 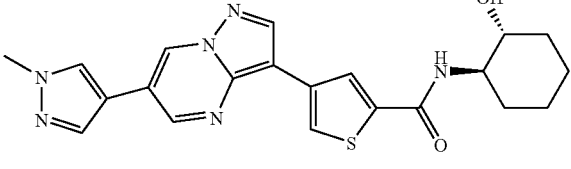 | 423.1 |
| (1S,2R)-2-[({5-methyl-4-[6-(1-methyl-1H-pyrazol-4-yl)pyrazolo[1,5-a]pyrimidin-3-yl]-2-thienyl}carbonyl)amino]cyclohexanaminium trifluoroacetate | 204 | 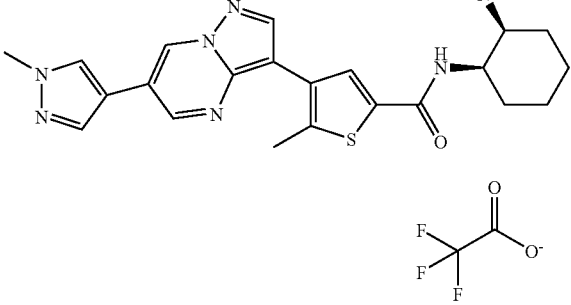 | 436.2 |
| 5-chloro-4-[6-(1-methyl-1H-pyrazol-4-yl)pyrazolo[1,5-a]pyrimidin-3-yl]-N-(2,2,2-trifluoroethyl)-1,3-thiazole-2-carboxamide | 205 | 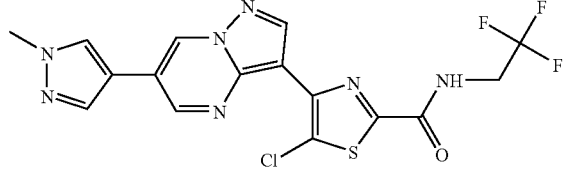 [SMILES: Cn1cc(-c2cnc3c(-c4nc(C(=O)NCC(F)(F)F)sc4Cl)cnn3c2)cn1] | 442 |
| N-[(1S,2S)-2-hydroxycyclohexyl]-4-[6-(1-methyl-1H-pyrazol-4-yl)pyrazolo[1,5-a]pyrimidin-3-yl]thiophene-2-carboxamide | 206 | 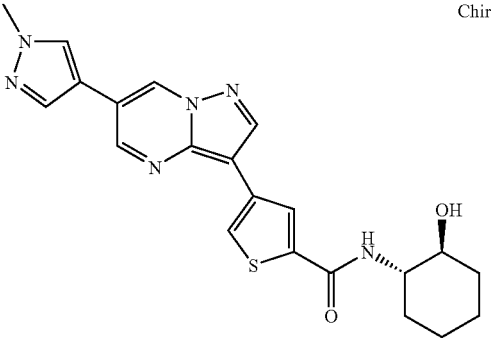 | 423.1 |

| Name | Example | Structure | LCMS M + H = |
|---|---|---|---|
| N-[(1R,6R)-6-amino-2,2-difluorocyclohexyl]-5-chloro-4-[6-(1-methyl-1H-pyrazol-4-yl)pyrazolo[1,5-a]pyridin-3-yl]-2-thiophenecarboxamide | 207 | 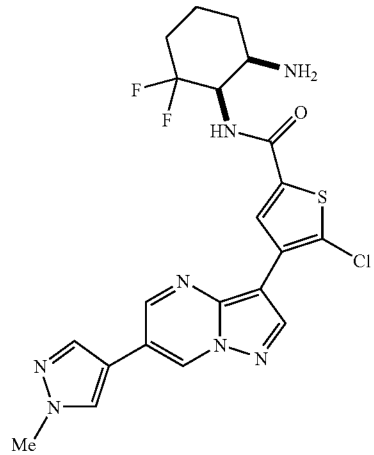 | 493 |
| N-[(1R,6S)-2,2-difluoro-6-hydroxycyclohexyl]-4-[6-(1-methyl-1H-pyrazol-4-yl)pyrazolo[1,5-a]pyrimidin-3-yl]thiophene-2-carboxamide | 208 | Chiral | 459 |

Example 209

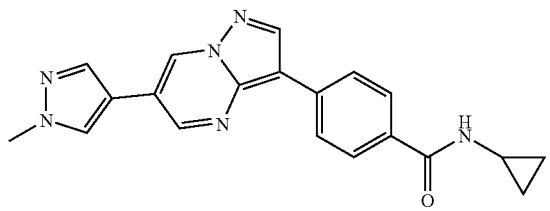 [SMILES: Cn1cc(-c2cnc3c(-c4ccc(C(=O)NC5CC5)cc4)cnn3c2)cn1]

N-cyclopropyl-4-[6-(1-methyl-1H-pyrazol-4-yl)pyrazolo[1,5-a]pyrimidin-3-yl]benzamide (Variation of Scheme 6)

Step A: Suzuki Coupling 3,6-Dibromopyrazolo[1,5-a]pyrimidine (2.0 g, 7.22 mmol) was mixed with 1-methyl-4-(4,4,5,5-tetramethyl-1,3,2-dioxaborolan-2-yl)-1H-pyrazole (1.51 g, 7.22 mmol). Dioxane (36 mL) and 1M Na₂CO₃ (10.8 mL) were added. The mixture was evacuated and flushed with nitrogen under stirring, then Pd(Ph₃P)₄ (0.42 g, 0.36 mmol) was added in a counter flow of nitrogen. The reaction mixture was heated to 85° C. under stirring for 16 h, cooled, and poured into a 5-fold excess of water. The product was extracted thrice with CH₂Cl₂. The organic layer was washed with brine, dried with MgSO₄, filtered, and evaporated. The residue was purified by column chromatography (1-5% methanol/DCM) to give 3-bromo-6-(1-methyl-1H-pyrazol-4-yl)pyrazolo[1,5-a]pyrimidine as a yellow solid: LC/MS [M+H]=277.9.

Step B: Suzuki Coupling

[4-(Methoxycarbonyl)phenyl]boronic acid (0.5 g, 2.77 mmol) was added to 3-bromo-6-(1-methyl-1H-pyrazol-4-yl)pyrazolo[1,5-a]pyrimidine (0.7 g, 2.52 mmol). DMF (12.5 mL) and 1M Na₂CO₃ (3.8 mL) were added. The mixture was evacuated and flushed with nitrogen under stirring, then Pd(Ph₃P)₄ (0.15 g, 0.13 mmol) was added in a counter flow of nitrogen. The reaction mixture was heated to 85° C. for 16 h, cooled, and poured into a 5-fold excess of water. The solids were filtered and dried to give crude methyl 4-[6-(1-methyl-1H-pyrazol-4-yl)pyrazolo[1,5-a]pyrimidin-3-yl]benzoate: LC/MS [M+H]=334.0.

Step C: Hydrolysis

A solution of methyl 4-[6-(1-methyl-1H-pyrazol-4-yl)pyrazolo[1,5-a]pyrimidin-3-yl]benzoate (0.5 g, 1.5 mmol) in methanol (7.0 mL) was treated with 1M potassium hydroxide in methanol (6.0 mmol, 6.0 mL) and the resulting solution was heated to 60° C. for 48 hours. The reaction was cooled to room temperature and treated with conc. HCl and evaporated to dryness. The solids were washed with water, filtered and dried in vacuo to give 4-[6-(1-methyl-1H-pyrazol-4-yl)pyrazolo[1,5-a]pyrimidin-3-yl]benzoic acid as a yellow solid: LC/MS [M+H]=320.0

Step D: Coupling

4-[6-(1-Methyl-1H-pyrazol-4-yl)pyrazolo[1,5-a]pyrimidin-3-yl]benzoic acid (50 mg, 0.16 mmol) was dissolved in DMF (2 mL). Resin bound CDI (288 mg, 0.4 mmol), HOBT (26 mg, 0.17 mmol), and cyclopropylamine (20 mg, 0.32 mmol) was added. The reaction was sealed and heated in the microwave at 120° C. for 20 minutes. The reaction was cooled to ambient temperature, filtered and purified by reverse phase chromatography to give N-cyclopropyl-4-[6-(1-methyl-1H-pyrazol-4-yl)pyrazolo[1,5-a]pyrimidin-3-yl]benzamide as a yellow solid: LC/MS [M+H]=359.0.

The following examples were prepared in an analogous manner to that described in Example 209 using the appropriate boronic acid in Step B and the appropriate amine in Step D:

| Name | Example | Structure | LCMS M + H = |
|---|---|---|---|
| 4-[6-(1-methyl-1H-pyrazol-4-yl)pyrazolo[1,5-a]pyrimidin-3-yl]benzamide | 210 | 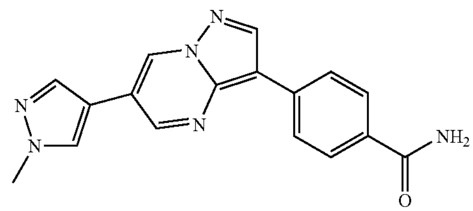 [SMILES: Cn1cc(-c2cnc3c(-c4ccc(C(N)=O)cc4)cnn3c2)cn1] | 319.0 |
| N-cyclobutyl-4-[6-(1-methyl-1H-pyrazol-4-yl)pyrazolo[1,5-a]pyrimidin-3-yl]benzamide | 211 | 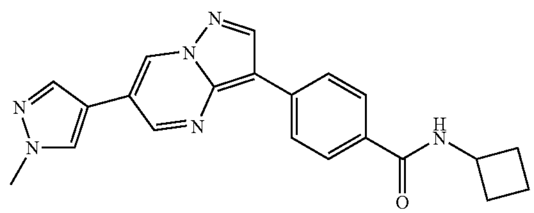 [SMILES: Cn1cc(-c2cnc3c(-c4ccc(C(=O)NC5CCC5)cc4)cnn3c2)cn1] | 373.0 |
| N-cyclopentyl-4-[6-(1-methyl-1H-pyrazol-4-yl)pyrazolo[1,5-a]pyrimidin-3-yl]benzamide | 212 | 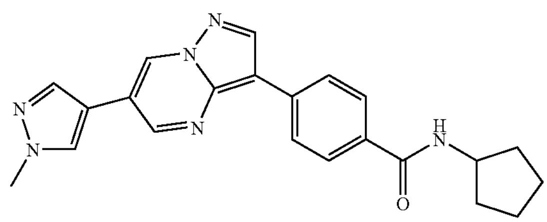 [SMILES: Cn1cc(-c2cnc3c(-c4ccc(C(=O)NC5CCCC5)cc4)cnn3c2)cn1] | 387.0 |
| N-(2-hydroxycyclopentyl)-4-[6-(1-methyl-1H-pyrazol-4-yl)pyrazolo[1,5-a]pyrimidin-3-yl]benzamide | 213 | 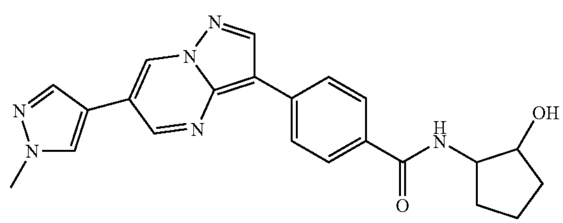 [SMILES: Cn1cc(-c2cnc3c(-c4ccc(C(=O)NC5CCCC5O)cc4)cnn3c2)cn1] | 403.0 |
| N-isobutyl-4-[6-(1-methyl-1H-pyrazol-4-yl)pyrazolo[1,5-a]pyrimidin-3-yl]benzamide | 214 | 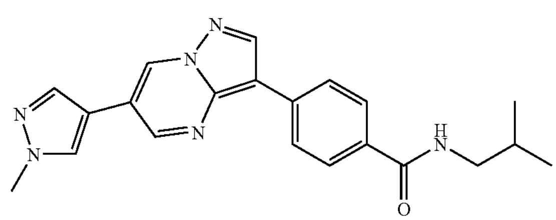 [SMILES: CC(C)CNC(=O)c1ccc(-c2cnn3cc(-c4cnn(C)c4)cnc23)cc1] | 375.0 |
| 4-[6-(1-methyl-1H-pyrazol-4-yl)pyrazolo[1,5-a]pyrimidin-3-yl]-N-(tetrahydrofuran-2-ylmethyl)benzamide | 215 | 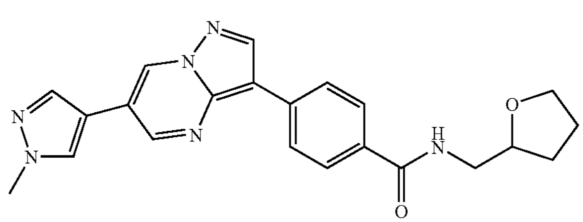 [SMILES: Cn1cc(-c2cnc3c(-c4ccc(C(=O)NCC5CCCO5)cc4)cnn3c2)cn1] | 403.0 |

| Name | Example | Structure | LCMS M + H = |
|---|---|---|---|
| 3-(4-{[(3S)-3-fluoropyrrolidin-1-yl]carbonyl}phenyl)-6-(1-methyl-1H-pyrazol-4-yl)pyrazolo[1,5-a]pyrimidine | 216 | 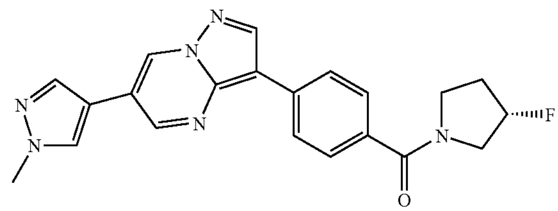 [SMILES: Cn1cc(-c2cnc3c(-c4ccc(C(=O)N5CC[C@H](F)C5)cc4)cnn3c2)cn1] | 391.0 |
| N-(3,3-difluorocyclopentyl)-4-[6-(1-methyl-1H-pyrazol-4-yl)pyrazolo[1,5-a]pyrimidin-3-yl]benzamide | 217 | 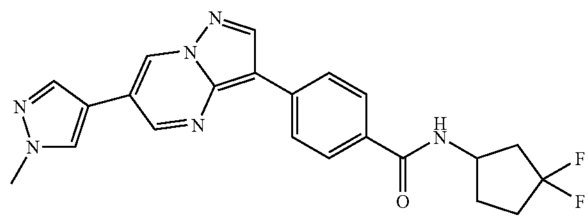 [SMILES: Cn1cc(-c2cnc3c(-c4ccc(C(=O)NC5CCC(F)(F)C5)cc4)cnn3c2)cn1] | 423.0 |
| N-isopropyl-4-[6-(1-methyl-1H-pyrazol-4-yl)pyrazolo[1,5-a]pyrimidin-3-yl]benzamide | 218 | 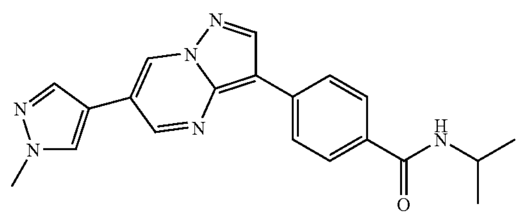 [SMILES: CC(C)NC(=O)c1ccc(-c2cnn3cc(-c4cnn(C)c4)cnc23)cc1] | 361.0 |
| N-[2-aminocyclohexyl]-4-[6-(1-methyl-1H-pyrazol-4-yl)pyrazolo[1,5-a]pyrimidin-3-yl]benzamide | 219 | 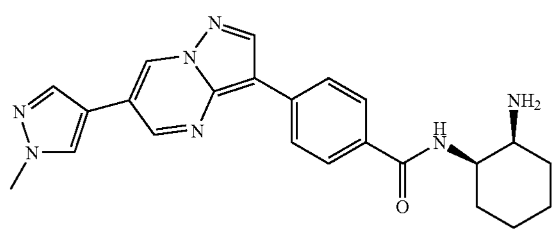 [SMILES: Cn1cc(-c2cnc3c(-c4ccc(C(=O)N[C@@H]5CCCC[C@@H]5N)cc4)cnn3c2)cn1] | 416.2 |
| N-cyclopentyl-3-[6-(1-methyl-1H-pyrazol-4-yl)pyrazolo[1,5-a]pyrimidin-3-yl]benzamide | 220 | 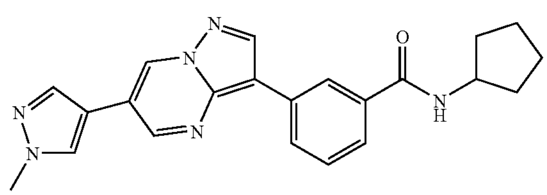 [SMILES: Cn1cc(-c2cnc3c(-c4cccc(C(=O)NC5CCCC5)c4)cnn3c2)cn1] | 387.1 |
| N-[(1S,2S)-2-hydroxycyclopentyl]-3-[6-(1-methyl-1H-pyrazol-4-yl)pyrazolo[1,5-a]pyrimidin-3-yl]benzamide | 221 | 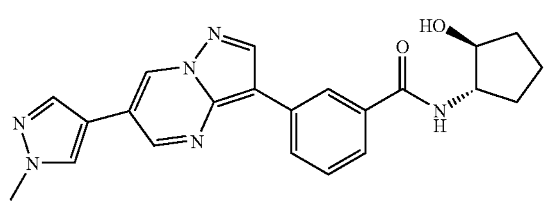 [SMILES: Cn1cc(-c2cnc3c(-c4cccc(C(=O)N[C@H]5CCC[C@@H]5O)c4)cnn3c2)cn1] | 403.2 |
| N-(1-cyclopropylethyl)-3-[6-(1-methyl-1H-pyrazol-4-yl)pyrazolo[1,5-a]pyrimidin-3-yl]benzamide | 222 | 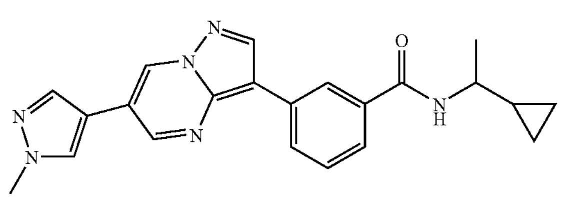 [SMILES: CC(NC(=O)c1cccc(-c2cnn3cc(-c4cnn(C)c4)cnc23)c1)C1CC1] | 387.0 |

-continued

| Name | Example | Structure | LCMS M + H = |
|---|---|---|---|
| N-cyclobutyl-3-[6-(1-methyl-1H-pyrazol-4-yl)pyrazolo[1,5-a]pyrimidin-3-yl]benzamide | 223 | 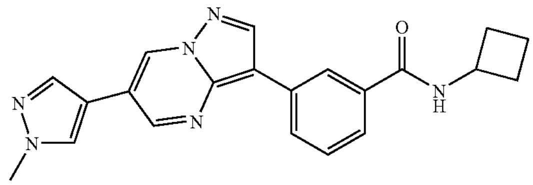 [SMILES: Cn1cc(-c2cnc3c(-c4cccc(C(=O)NC5CCC5)c4)cnn3c2)cn1] | 373.1 |
| 6-(1-methyl-1H-pyrazol-4-yl)-3-(3-{[3-(trifluoromethyl)piperidin-1-yl]carbonyl}phenyl)pyrazolo[1,5-a]pyrimidine | 224 | 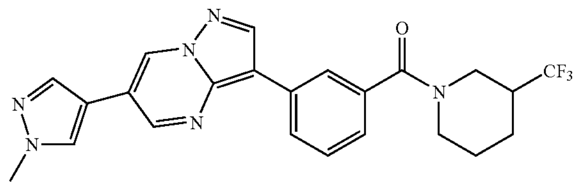 [SMILES: Cn1cc(-c2cnc3c(-c4cccc(C(=O)N5CCCC(C(F)(F)F)C5)c4)cnn3c2)cn1] | 455.1 |
| N-(2-hydroxycyclopentyl)-3-[6-(1-methyl-1H-pyrazol-4-yl)pyrazolo[1,5-a]pyrimidin-3-yl]benzamide | 225 | 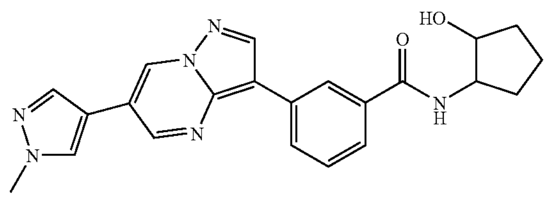 [SMILES: Cn1cc(-c2cnc3c(-c4cccc(C(=O)NC5CCCC5O)c4)cnn3c2)cn1] | 403.1 |
| N-(3,3-difluorocyclopentyl)-3-[6-(1-methyl-1H-pyrazol-4-yl)pyrazolo[1,5-a]pyrimidin-3-yl]benzamide | 226 | 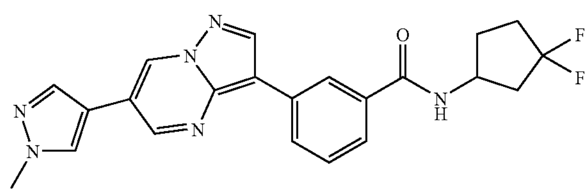 [SMILES: Cn1cc(-c2cnc3c(-c4cccc(C(=O)NC5CCC(F)(F)C5)c4)cnn3c2)cn1] | 423.1 |
| N-isopropyl-3-[6-(1-methyl-1H-pyrazol-4-yl)pyrazolo[1,5-a]pyrimidin-3-yl]benzamide | 227 | 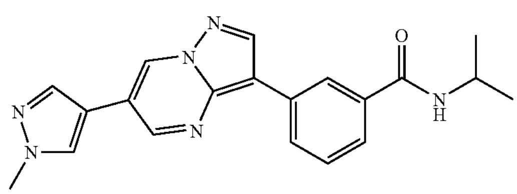 [SMILES: CC(C)NC(=O)c1cccc(-c2cnn3cc(-c4cnn(C)c4)cnc23)c1] | 361.2 |
| N-(2-methoxy-1-methylethyl)-3-[6-(1-methyl-1H-pyrazol-4-yl)pyrazolo[1,5-a]pyrimidin-3-yl]benzamide | 228 | 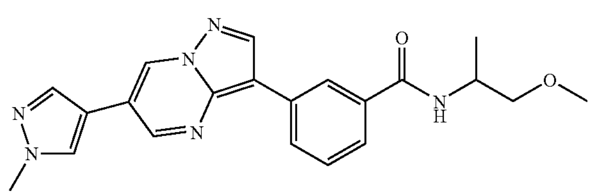 | 391.1 |
| N-isobutyl-3-[6-(1-methyl-1H-pyrazol-4-yl)pyrazolo[1,5-a]pyrimidin-3-yl]benzamide | 229 | 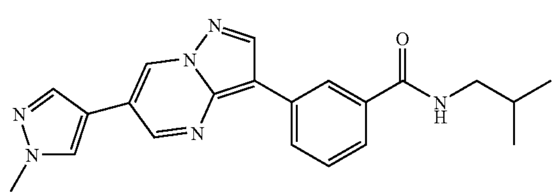 [SMILES: CC(C)CNC(=O)c1cccc(-c2cnn3cc(-c4cnn(C)c4)cnc23)c1] | 375.2 |

Example 230

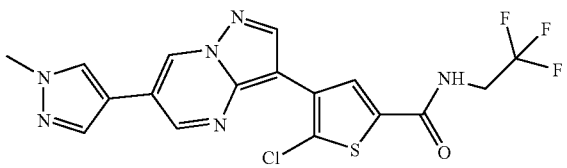 [SMILES: Cn1cc(-c2cnc3c(-c4cc(C(=O)NCC(F)(F)F)sc4Cl)cnn3c2)cn1]

5-chloro-4-[6-(1-methyl-1H-pyrazol-4-yl)pyrazolo
[1,5-a]pyrimidin-3-yl]-N-(2,2,2-trifluoroethyl)
thiophene-2-carboxamide Step A: Chlorination 4-[6-(1-methyl-1H-pyrazol-4-yl)pyrazolo[1,5-a]pyrimidin-3-yl]-N-(2,2,2-trifluoroethyl)thiophene-2-carboxamide (107 mg, 0.263 mmol) was taken up in thionyl chloride (2 ml, 27.4 mmol) and heated at 80° C. overnight. Evaporated solvent under vacuum and took up in 3 ml DMF, purified reverse-phase 30-100% ACN/H₂O w/0.1% TFA. Evaporated solvent under vacuum to yield 60 mgs pale yellow solid (51.7%). LRMS [M+H]=441.0

Intermediates

Certain intermediates used in the synthesis of examples described above were prepared as follows.

Intermediate I

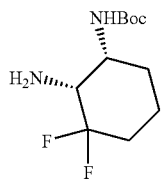

tert-butyl
[(1R,6R)-2-amino-3,3-difluorocyclohexyl]carbamate
(Scheme 9)

Step A: Difluorination

To a solution of 7-oxabicyclo[4.1.0]heptan-2-one (55.8 g, 0.5 mol) in dichloromethane (200 mL) cooled to 0° C. was added 1,1,1-trifluoro-N,N-bis(2-methoxyethyl)silanamine (Deoxofluor, 202 mL, 1.1 mol) and the resulting reaction was warmed to ambient temperature and stirred for 16 hours. The reaction was cooled to −20° C. and carefully quenched with water (10 mL, slow addition). The reaction was then partitioned between water/dichloromethane and the organics were passed through a plug of silica gel. This crude organic solution of 30 was carried into the next reaction.

Step B: Epoxide Opening

A solution of (1R)-1-phenylethanamine (30, 72 mL, 0.57 mol) in dichloromethane (200 mL) was cooled to 0° C. and treated with trimethylaluminum (260 mL, 0.52 mol) and the resulting solution was stirred for 1 hour at 0° C. To this solution was added a solution of 2,2-difluoro-7-oxabicyclo[4.1.0]heptane (66 g, 0.49 mol) in dichloromethane (200 mL) and the resulting mixture stirred at 0° C. for 3 hours. The reaction was then warmed to ambient temperature for 16 hours. The reaction was cooled to 0° C., treated with 103 g of sodium fluoride and then quenched with water (90 mL, slow addition). The reaction was warmed to ambient temperature, the solids filtered and the solution evaporated in vacuo. Purification by flash chromatography (50-100% ethyl acetate in hexanes) gave 36.3 g (29%) of (1S,6R)-2,2-difluoro-6-{[(1R)-1-phenylethyl]amino}cyclohexanol 31 (plus 32 g of 1R,6S diastereomer) as a white solid: ¹H NMR (500 MHz, CDCl₃) δ 7.32 (5H, s), 3.90 (1H, q, J=6.6 Hz,), 3.39 (1H, ddd, J=19.8, 9.8, 4.2 Hz), 2.70 (1H, m), 2.11 (1H, m), 1.80 (1H, m), 1.62 (2H, m), 1.43 (1H, m), 1.36 (3H, d, J=6.6 Hz), 0.96 (1H, m).

Step C: Hydrogenation

A solution of (1S,6R)-2,2-difluoro-6-{[(1R)-1-phenylethyl]amino}cyclohexanol 31 (2 g, 7.83 mmol) in methanol (100 mL) was degassed with nitrogen, treated with Pd(OH)₂/C (0.55 g) and then placed under an atmosphere of hydrogen and stirred vigorously for 16 hours. The reaction was filtered, washing with methanol, and evaporated in vacuo to give 1.0 g (84%) of (1S,6R)-6-amino-2,2-difluorocyclohexanol 32 as a white solid: ¹H NMR (500 MHz, CD₃OD) δ 3.34 (1H, m), 2.74 (1H, m), 2.07 (1H, m), 1.89 (1H, m), 1.73 (2H, m), 1.50 (1H, m), 1.27 (1H, m).

Step D: Amine Protection

A solution of (1S,6R)-6-amino-2,2-difluorocyclohexanol 32 (2 g, 7.54 mmol) in dichloromethane (60 mL) was treated with triethylamine (5.26 mL, 37.7 mmol) and Boc anhydride (1.81 g, 8.30 mmol) and the resulting solution was stirred at ambient temperature for 16 hours. The reaction was evaporated in vacuo and purified by flash column chromatography (10-30% ethyl acetate in hexanes) to give 0.6 g (32%) of tert-butyl [(1R,2S)-3,3-difluoro-2-hydroxycyclohexyl]carbamate 33 as a white solid: ¹H NMR (500 MHz, CDCl₃) δ 4.67 (1H, bs), 3.67 (1H, bm), 3.50 (1H, bm), 3.21 (1H, bs), 2.15 (1H, m), 2.03 (1H, m), 1.62 (3H, m), 1.45 (9H, s), 1.34 (1H, m).

Step E: Triflate Formation

A solution of tert-butyl [(1R,6S)-3,3-difluoro-2-hydroxycyclohexyl]carbamate 33 (1.78 g, 7.08 mmol) in dichloromethane (50 mL) was treated with pyridine (12.5 mL) and cooled to 0° C. Triflic anhydride (4.43 mL, 26.2 mmol) was added dropwise and the reaction was stirred at 0° C. for 2 hours and quenched with water. The reaction was partitioned between water and ether, the organics were dried over sodium sulfate, filtered and evaporated in vacuo. Purification by flash chromatography (0-15% ethyl acetate in hexanes) gave 2.33 (86%) of (1S,6R)-6-[(tert-butoxycarbonyl)amino]-2,2-difluorocyclohexyl trifluoromethanesulfonate 34 as a white solid: ¹H NMR (500 MHz, CDCl₃) δ 4.77 (bm, 1H), 4.69 (bd, 1H), 3.92 (bm, 1H), 2.28 (m, 1H), 2.08 (m, 1H), 1.79 (m, 2H), 1.64 (m, 2H), 1.45 (s, 9H).

Step F: Azide Displacement

A solution of (1S,6R)-6-[(tert-butoxycarbonyl)amino]-2,2-difluorocyclohexyl trifluoromethanesulfonate 34 (2.32 g, 6.05 mmol) and sodium azide (2.36 g, 36.3 mmol) in DMF was sealed and heated to 100° C. for 3 hours in a microwave reactor. The reaction was partitioned between water and ethyl acetate. The organics were washed with water, dried over magnesium sulfate, filtered and evaporated in vacuo. Purification by flash chromatography (0-15% ethyl acetate in hexanes) gave 0.94 g (56%) of tert-butyl [(1R,2R)-2-azido-3,3-difluorocyclohexyl]carbamate 36 as a white solid: NMR (500 MHz, CDCl₃) δ 4.75 (1H, m), 3.98 (1H, bs), 3.88 (1H, bm), 1.96 (2H, m), 1.70 (2H, m), 1.46 (9H, s), 1.37 (2H, m).

The diastereomer 35 was also obtained from this procedure: $^1$H NMR (500 MHz, CDCl$_3$) δ 4.82-4.80 (1H, br d, J=9.4 Hz), 3.93-3.89 (1H, dt, J=11.1, 10.5, 12.6, 8.1 Hz), 3.31-3.27 (1H, m), 2.24-2.19 (1H, m), 2.13-2.10 (1H, m), 1.86-1.67 (2H, m), 1.55-1.52 (2H, m), 1.48-1.41 (11H, m); $^{19}$F NMR (CDCl$_3$, 564 MHz) δ −102.2−−102.7 (1F, d, J=244 Hz), −113.9−−114.5 (IF, m).

Step G: Azide Reduction

A solution of tert-butyl [(1R,6R)-2-azido-3,3-difluorocyclohexyl]carbamate 36 (0.94 g, 3.40 mmol) in methanol (20 mL) was degassed with nitrogen and treated with 10% PdJC (72 mg). The resulting heterogenous solution was exposed to a hydrogen atmosphere and stirred vigorously for 16 hours. The reaction was filtered, washing with methanol, and evaporated in vacuo to give 0.78 g (91%) of tert-butyl [(1R,2R)-2-amino-3,3-difluorocyclohexyl]carbamate 37 as a white solid: $^1$H NMR (500 MHz, DMSO-d$_6$) δ 6.67 (1H, d, J=8.3 Hz), 3.55 (1H, bs), 3.07 (1H, bs), 2.03 (1H, m), 1.62 (3H, m), 1.45 (1H, m), 1.36 (12H, m).

Intermediate II

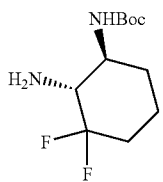

tert-butyl [(1R,6S)-2-amino-3,3-difluorocyclohexyl]carbamate (Scheme 10)

Step A: Reduction of Azide

To a clean dry 1 L RBF charged with tert-butyl [(1R,2S)-2-azido-3,3-difluorocyclohexyl]carbamate 35 (18.84 g, 68.2 mmol) was added 400 mL methanol. The system was degassed and purged (3× with N$_2$) before the addition of Pd/C (1.45 g). The reaction was stirred for 2 d under 1 atm of hydrogen. Upon reaction completion, the reaction was filtered through a plug of celite and concentrated to dryness to yield tert-butyl [(1R,2S)-2-amino-3,3-difluorocyclohexyl] carbamate 38 (16.47 g, 97% yield) as a pure white solid. $^1$H NMR (CDCl$_3$, 500 MHz) δ 4.76-4.74 (1H, d, J=10 Hz), 3.61-3.56 (1H, m), 2.63-2.59 (1H, dd J=9.5 Hz), 2.2-2.0 (2H, m), 1.8-1.68, (2H, m), 1.53-1.42 (11H, m), 1.29-1.21 (m, 2H); $^{19}$F NMR (CDCl$_3$, 564 MHz) δ −101.7−−102.1 (1F, J=241 Hz), −114.3−−114.9 (1F, m)

Step B: BOC-Deprotection

To a clean dry 100 ml RBF was added 38 (5 g, 19.98 mmol), dichloromethane (50 mL) and TFA (6.16 mL, 80 mmol). The reaction was stirred overnight. Upon reaction completion, the solvent was removed under reduced pressure and 7.5 g (99%) pure bis-TFA salt 39 was isolated as a brown oil. $^{19}$F NMR (CDCl$_3$, 564 MHz) δ −81.07 (6F, s), −99.7−−100.1 (1F, d, J=241.6 Hz), −111.1−−111.5 (1F, br d, J=242.1 Hz).

Step C: Monoprotection of Diamine

To a clean dry 250 ml RBF charged with 39 (7.5 g, 19.8 mmol) was added dichloromethane (100 mL), triethylamine (11.1 mL, 79.0 mmol) followed by BOC$_2$O (5.52 mL, 23.8 mmol). The reaction was stirred for 10 hr at ambient temperature. Upon completion, the solvent was removed under reduced pressure and the resultant residue was purified by column chromatography (silica gel, 10-50% ethyl acetate in hexanes with 1% NH$_4$OH, linear gradient) to yield tert-butyl [(1R,2S)-2-amino-3,3-difluorocyclohexyl]carbamate 40 (1.8 g, 38% yield) of pure material isolated, along with 2.2 g mixed Boc-products. $^1$H NMR (CDCl$_3$, 500 MHz) δ 4.76 (1H, br s), 3.39 (br m, 1H), 2.71-2.64 (1H, m), 2.2-2.1 (2H, m), 1.7-1.59 (2H, m), 1.56-1.51 (2H, m), 1.45 (9H, s), 1.29-1.21 (2H, m); $^{19}$F NMR (CDCl$_3$, 564 MHz) δ −100.4−−100.9 (1F, d, J=236 Hz), −114.35−−114.87 (1F, br d, J=232 Hz)

Intermediate III

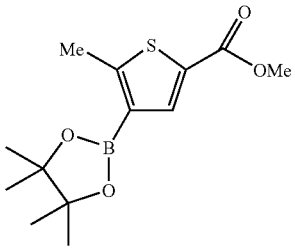 [SMILES: COC(=O)c1cc(B2OC(C)(C)C(C)(C)O2)c(C)s1]

methyl 5-methyl-4-(4,4,5,5-tetramethyl-1,3,2-dioxaborolan-2-yl)-2-thiophenecarboxylate (Scheme 11)

Step A: Esterification

In a 5 mL microwave vial was added 4-bromo-5-methyl-2-thiophenecarboxylic acid (41) (1.03 g, 4.66 mmol) and trimethyl orthoacetate (1.53 ml, 13.98 mmol), neat. The system was heated at 40 min at 100° C. The reaction was then partitioned between water and DCM. The organic was dried over sodium sulfate and concentrated. The crude material 42 was used directly in the next step. MS APCI: [M+H]$^+$ m/z 236.1.

Step B: Boronic Ester Synthesis

To ester 42 (213 mg, 0.963 mmol) in DMSO (4.8 mL) was added potassium acetate (284 mg, 2.89 mmol) and pinacolato diboron (269 mg, 1.060 mmol). This heterogeneous solution was sparged for 15 minutes with Ar$_{(g)}$. PdCl$_2$(dppf) (211 mg, 0.289 mmol) was added and the system was purged Ar$_{(g)}$ and before heating at 80° C. for 4 hr. The reaction was diluted with water (10 mL) and extracted with dichloromethane (2×15 mL). The combined organics were dried over sodium sulfate and then concentrated under reduced pressure. The resultant residue was purified by column chromatography (0-20% acetone in hexanes, linear gradient). give 0.139 g (51% yield) of methyl 5-methyl-4-(4,4,5,5-tetramethyl-1,3,2-dioxaborolan-2-yl)-2-thiophenecarboxylate, 43: $^1$H NMR (500 MHz, CDCl$_3$) δ 7.92 (1H, s), 3.83 (3H, s), 2.68 (3H, s), 1.31 (6H, s), 1.25 (6H, s).

Intermediate IV

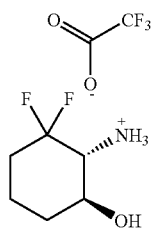

(1R,6S)-2,2-difluoro-6-hydroxycyclohexanaminium trifluoroacetate (Scheme 12)

Step A: Mesylate Formation

Triethylamine (0.273 mL, 1.958 mmol) was added to a solution of 31 (500 mg, 1.958 mmol) in THF (10 ml). After 5 minutes, added methanesulfonyl chloride (0.183 mL, 2.350 mmol). The reaction was allowed to stir at 35° C. overnight. After cooling to room temperature, the reaction mixture was filtered and the filtrate concentrated under pressure to yield crude desired product. The crude product was purified by NP FC (20-60% Ethyl Acetate/Hexanes) to yield 44 (470 mg, 1.410 mmol, 72.0% yield). $^1$H NMR (CDCl$_3$, 500 MHz) δ 7.38-7.30 (4H, m), 7.27-7.22 (1H, m), 4.64-4.52 (1H, m), 4.08-4.0 (1H, q J=6.5 Hz), 3.19 (3H, s), 2.84-2.76, (1H, m), 2.22-2.08 (1H, m), 1.86-1.78 (1H, m), 1.66-1.58 (1H, m), 1.4-1.3 (4H, m), 1.28-1.16 (1H, m); $^{19}$F NMR (CDCl3, 470 MHz) δ −99.56--100.3 (1F, J=245 Hz), −113.5--115.0 (1F, m).

Step B: Aziridine Formation

Triethylamine (393 µl, 2.82 mmol) was added to a solution of 44 (470 mg, 1.410 mmol) in THF (7049 µl) in a sealed microwave vial. The reaction was run in an oil bath at 100° C. overnight. After cooling to room temperature, the reaction mixture was concentrated under pressure, taking care not to let the water bath temperature go above 35° C. The crude concentrated reaction mixture was loaded onto silica column and purified (0-70% Ether/Hexanes) to yield 45. $^1$H NMR (CDCl$_3$, 500 MHz) δ 7.46-7.42 (2H, m), 7.41-7.36 (2H, m), 7.34-7.28 (1H, m), 2.67-2.61 (1H, q J=6.4 Hz), 2.1-1.94, (2H, m), 1.85-1.50 (5H, m), 1.50-1.4 (3H, d J=6.6 Hz); $^{19}$F NMR (CDCl3, 470 MHz) δ −92.42--93.08 (1F, J=248 Hz), −96.86--97.54 (1F, m).

Step C: Aziridine Opening

Assuming theoretical yield from previous step, refluxed 45 in 9M sulfuric acid (5000 µl, 45.0 mmol) for 2 hours. After cooling to room temperature, the reaction mixture was quenched with 1N NaOH. The mixture was then diluted with water and extracted three times with dichloromethane. The organic layer was combined and dried under pressure. Crude product purified by RP FC at 215 nm to yield 46 (283 mg, 0.766 mmol, 54.3% yield). $^1$H NMR (CD3OD, 500 MHz) δ 7.57-7.52 (2H, m), 7.48-7.40 (3H, m), 4.80-4.73 (1H, q J=6.9 Hz), 3.89-3.81 (1H, m), 3.45-3.33, (1H, m), 2.26-2.14 (1H, m), 2.12-2.0 (1H, m), 2.0-1.82 (1H, m), 1.75-1.70 (3H, d J=7.1 Hz), 1.54-1.41 (1H, m); $^{19}$F NMR (CD3OD, 470 MHz) δ −96.06--96.2 (1F, J=246 Hz), −111.42--111.68 (1F, m).

Step D: Hydrogenation

Palladium on carbon (163 mg, 0.153 mmol) added to a solution of 46 (283 mg, 0.766 mmol) in methanol (5108 µl). Reaction flask connected to a hydrogen balloon and the reaction allowed to stir under a hydrogen atmosphere over the weekend. Reaction mixture then filtered through a bed of celite and washed three times with ~30 mL of methanol. Filtrate evaporated under pressure to yield 47 (190 mg, 0.717 mmol, 94% yield). $^1$H NMR (CD$_3$OD, 500 MHz) δ 3.7-3.62 (1H, m), 3.39-3.28 (1H, m), 2.26-2.14 (1H, m), 2.21-2.0 (1H, m), 2.0-1.76, (2H, m), 1.58-1.40 (2H, m); $^{19}$F NMR (CD3OD, 470 MHz) δ −99.66--100.3 (1F, J=243 Hz), −115.16--115.92 (1F, m).

Intermediate V

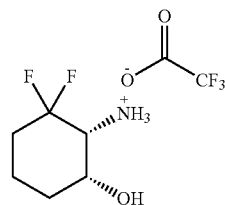

(1R,6R)-2,2-difluoro-6-hydroxycyclohexanaminium trifluoroacetate (Scheme 13)

Step A: Boc Protection

DIPEA (125 µl, 0.717 mmol) added to solution of 47 (190 mg, 0.717 mmol) in DCM (3583 µl). After 5 minutes added Boc Anhydride (183 µl, 0.788 mmol); the reaction mixture was stirred at RT overnight. Dichloromethane removed under pressure and the remaining residue purified by NP FC (100% hexanes to elute Boc byproducts then 0-50% Ethyl Acetate/Hexanes to elute product) to yield 48 (173 mg, 0.689 mmol, 96% yield). $^1$H NMR (CDCl$_3$, 500 MHz) δ 5.35-5.0 (1H, m), 3.82-3.66 (1H, m), 3.52-3.49 (1H, m), 3.49-3.4 (1H, br s), 2.18-2.0, (2H, m), 1.8-1.6 (2H, m), 1.5-1.3 (11H, m); $^{19}$F NMR (CDCl$_3$, 470 MHz) δ −99.32--99.98 (1F, J=243 Hz), −113.4-114.36 (1F, m).

Step B: Carbamate Formation

A solution of 48 (173 mg, 0.689 mmol) in DCM (2754 µl) and Pyridine (689 µl) was cooled to −20 C. Triflic Anhydride (116 µl, 0.689 mmol) was slowly added and the reaction allowed to stir at −20° C. until completion. After warming to RT, the reaction mixture was diluted with water and extracted three times with dichloromethane. The combined organic layers were evaporated to dryness. The remaining residue was purified by silica plug (100% Hexanes then 0-50% Ethyl Acetate/Hexanes to elute product) to yield 49 (104 mg, 0.587 mmol, 85% yield). $^{19}$F NMR (CDCl$_3$, 470 MHz) δ −93.08--93.78 (1F, m), −100.6--101.32 (1F, m).

Step C: Carbamate Opening

Lithium hydroxide (60.4 mg, 1.411 mmol) in THF (1086 µl), Methanol (109 µl), and Water (217 µl) added to a flask containing 49 (50 mg, 0.282 mmol). The reaction was stirred at 50° C. over the weekend. After cooling to RT, the reaction mixture was filtered. TFA (500 µl, 6.49 mmol) was added to filtrate and the mixture stirred vigorously for one minute. The mixture was then concentrated under pressure to yield 50. $^1$H NMR (CD3OD, 500 MHz) δ 4.23-4.17 (1H, m), 3.68-3.60

(1H, m), 2.22-2.12 (1H, m), 2.0-1.8 (3H, m), 1.72-1.58, (2H, m); $^{19}$F NMR (CD3OD, 470 MHz) δ −96.6−−97.7 (1F, J=245 Hz), −108.0−−109.5 (1F, m)

| Glossary | |
|---|---|
| DMF | dimethylformamide |
| DMSO | dimethylsulfoxide |
| p-TSA | p-toluenesulfonic acid |
| BOP | benzotriazol-1-yloxytris(dimethylamino)phosphonium hexafluorophosphate |
| DIPEA/DIEA | diisopropylethylamine |
| dppf | 1,1'-bis(diphenylphosphino)ferrocene |
| CDI | 1,1'-carbonyldiimidazole |
| TBAT | tetrabutylammonium triphenyldifluorosilicate |
| HOBT | 1-hydroxybenzotriazole |
| ACN | acetonitrile |
| CAN | ceric ammonium nitrate |
| Tf | triflyl (trifluoromethanesulfonyl) |

The invention claimed is:

1. A compound of formula I:

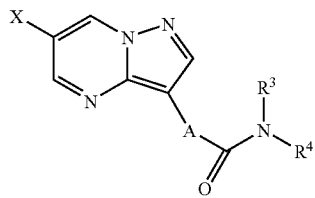

or a pharmaceutically acceptable salt thereof; wherein:
A represents a phenyl, thienyl or thiazolyl ring, which bears 0-3 substituents independently selected from halogen, CN, $C_{1-4}$alkyl, $CF_3$ and $C_{1-4}$alkoxy;
X represents a monocyclic ring system comprising 5-6 ring atoms, of which 1-3 are selected from N, O and S and the remainder are C, said ring system bearing 0-3 substituents independently selected from halogen, CN, $R^1$-L, $R^1$O-L, $R^1R^2$N-L and $R^1$CONR$^2$;
L represents a bond or a linking group selected from CO, $(CO)_m(CH_2)_n$, $(CO)_m(CH_2)_nO$, $(CO)_m(CH_2)_nNR^2$ and $(CO)_m(CH_2)_nS$;
m is 0 or 1;
n is 0, 1, 2, 3 or 4;
$R^1$ is selected from:
H;
$C_{1-6}$alkyl which is optionally substituted with up to 3 halogen atoms or with OH, CN, $C_{3-6}$cycloalkyl, $C_{1-4}$alkoxy, $C_{1-4}$alkoxycarbonyl, amino, $C_{1-4}$alkylamino or di($C_{1-4}$alkyl)amino; and
phenyl or $C_{3-6}$cycloalkyl, either of which is optionally substituted with up to 3 halogen atoms or with OH, CN, $CF_3$, $C_{1-4}$alkyl, $C_{1-4}$alkoxy, $C_{1-4}$alkoxycarbonyl, amino, $C_{1-4}$alkylamino or di($C_{1-4}$alkyl)amino;
$R^2$ represents H or $C_{1-4}$alkyl;
or $R^1$ and $R^2$ attached to the same nitrogen atom may complete a heterocycle of up to 7 ring atoms which is optionally substituted with up to 3 halogen atoms or with OH, CN, $CF_3$, $C_{1-4}$alkyl, $C_{1-4}$alkoxy, $C_{1-4}$alkoxycarbonyl, amino, $C_{1-4}$alkylamino or di($C_{1-4}$alkyl)amino;
$R^3$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^4$ is selected from:
(i) H;
(ii) $C_{1-8}$alkyl or $C_{2-8}$alkenyl, either of which optionally bears up to 3 substituents independently selected from halogen, OH, CN, $CF_3$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$; and
(iii) $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^7$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms;
or $R^3$ and $R^4$ together may complete a mono- or bicyclic heterocyclic system of up to 10 ring atoms which optionally bears up to 3 substituents independently selected from halogen, OH, oxo, CN, $CF_3$, $R^7$, $OR^6$, $SR^7$, $SO_2R^7$, $SO_2N(R^6)_2$, $COR^6$, $CO_2R^6$, $CON(R^6)_2$, $N(R^6)_2$, $NR^6COR^7$ and $NR^6SO_2R^7$;
$R^6$ represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^6$ represents phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;
or two $R^6$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino; and
$R^7$ has the same definition as $R^6$ except that $R^7$ is not H.

2. A compound according to claim 1 or a pharmaceutically acceptable salt thereof, wherein X represents 2-oxo-1,2-dihydropyridin-4-yl which bears a substituent $R^1R^2N(CH_2)_p$ on the 1-position, where p is 2 or 3.

3. A compound according to claim 1 or a pharmaceutically acceptable salt thereof, wherein X represents 3-pyridine which is unsubstituted or substituted in the 6-position.

4. A compound according to claim 3 or a pharmaceutically acceptable salt thereof, wherein the substituent is selected from $NH_2$, dimethylamino, piperazin-1-yl, 4-methylpiperazin-1-yl, 2-(morpholin-1-yl)ethylamino, cyclopropylmethoxy, acetylamino, 3-(dimethylamino)propoxy, methoxy, 2-hydroxy-2-methylpropylamino, morpholin-1-yl and 2-methoxyethylamino.

5. A compound according to claim 1 or a pharmaceutically acceptable salt thereof, wherein X represents optionally-substituted 5-membered heteroaryl.

6. A compound according to claim 5 or a pharmaceutically acceptable salt thereof, wherein X represents 1-methyl-1H-pyrazol-5-yl, 1-methyl-1H-pyrazol-4-yl, 1-methyl-1H-imidazol-4-yl, 1-benzyl-1H-pyrazol-4-yl, 1H-pyrrol-2-yl, 1H-pyrazol-3-yl, 3-thienyl, 3-furyl, 2-furyl, 5-acetyl-2-thienyl or 1H-pyrazol-4-yl.

7. A compound according to claim 1 or a pharmaceutically acceptable salt thereof, which is a compound of formula II:

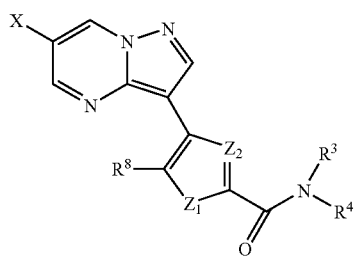

(II)

or a pharmaceutically acceptable salt thereof; wherein:
$Z_1$ represents S;
$Z_2$ represents N or $CR^9$; and
$R^8$ and $R^9$ are independently selected from H, halogen, CN, $C_{1-4}$-alkyl, $CF_3$ and $C_{1-4}$alkoxy.

8. A compound according to claim 7 or a pharmaceutically acceptable salt thereof, wherein $Z_2$ is $CR^9$ and $R^8$ is H, methyl or Cl; or $Z_2$ is N and $R^8$ is H, methyl or Cl.

9. A compound of claim 7 or a pharmaceutically acceptable salt thereof, wherein X represents 1-methylpyrazol-4-yl.

10. A compound according to claim 7 or a pharmaceutically acceptable salt thereof, wherein $R^3$ is H and $R^4$ represents:

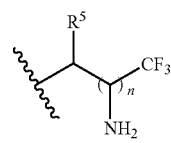

(i)

where n is 0 or 1 and $R^5$ represents H, $C_{1-6}$alkyl, phenyl or pyridyl, said phenyl or pyridyl optionally bearing a substituent selected from halogen, $CF_3$, $C_{1-4}$-alkyl and $C_{1-4}$-alkoxy; or $R^4$ represents:

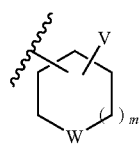

(ii)

where m is 0 or 1, V represents H, OH or $NH_2$ and W represents $CH_2$, $CF_2$ or $SO_2$.

11. A compound according to claim 7 or a pharmaceutically acceptable salt thereof, wherein $R^4$ is of formula (i)

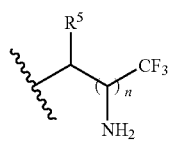

(i)

where n is 0 or 1 and $R^5$ represents H, isopropyl, phenyl, 2-pyridyl, 5-fluoro-2-pyridyl or 6-methyl-2-pyridyl; or wherein $R^4$ is of formula (ii)

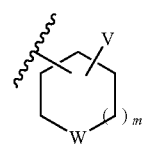

(ii)

and m is 1, V is $NH_2$ and W is $CF_2$.

12. A compound of claim 1 or a pharmaceutically acceptable salt thereof, wherein X represents 1-methylpyrazol-4-yl.

13. A compound according to claim 1 or a pharmaceutically acceptable salt thereof, wherein $R^3$ is H and $R^4$ represents:

(i)

where n is 0 or 1 and $R^5$ represents H, $C_{1-6}$alkyl, phenyl or pyridyl, said phenyl or pyridyl optionally bearing a substituent selected from halogen, $CF_3$, $C_{1-4}$-alkyl and $C_{1-4}$-alkoxy; or $R^4$ represents:

(ii)

where m is 0 or 1, V represents H, OH or $NH_2$ and W represents $CH_2$, $CF_2$ or $SO_2$.

14. A pharmaceutical composition comprising a compound of formula I as defined in claim 1 or a pharmaceutically acceptable salt thereof, and a pharmaceutically acceptable carrier.

* * * * *